United States Patent
Ikeda et al.

(10) Patent No.: US 12,247,244 B2
(45) Date of Patent: Mar. 11, 2025

(54) MEMBRANE PROTEIN ACTIVITY MEASUREMENT METHOD

(71) Applicant: THE UNIVERSITY OF TOKYO, Tokyo (JP)

(72) Inventors: Yuichi Ikeda, Tokyo (JP); Hidetoshi Kumagai, Tokyo (JP)

(73) Assignee: THE UNIVERSITY OF TOKYO, Tokyo (JP)

(*) Notice: Subject to any disclaimer, the term of this patent is extended or adjusted under 35 U.S.C. 154(b) by 939 days.

(21) Appl. No.: 17/263,410

(22) PCT Filed: Jul. 26, 2019

(86) PCT No.: PCT/JP2019/029424
§ 371 (c)(1),
(2) Date: May 3, 2021

(87) PCT Pub. No.: WO2020/026979
PCT Pub. Date: Feb. 6, 2020

(65) Prior Publication Data
US 2021/0310039 A1    Oct. 7, 2021

(30) Foreign Application Priority Data
Jul. 31, 2018    (JP) .................. 2018-144171

(51) Int. Cl.
*C12Q 1/06* (2006.01)
*C12N 15/10* (2006.01)
(Continued)

(52) U.S. Cl.
CPC .......... *C12Q 1/06* (2013.01); *C12N 15/1086* (2013.01); *C12N 15/62* (2013.01); *C12N 15/85* (2013.01); *C12Q 1/66* (2013.01)

(58) Field of Classification Search
CPC ........ C12Q 1/06; C12Q 1/66; C12N 15/1086; C12N 15/62; C12N 15/85; C12N 2830/002; G01N 2500/04; C40B 30/04
See application file for complete search history.

(56) References Cited

U.S. PATENT DOCUMENTS

| 6,555,325 B1 | 4/2003 | Oehlen |
| 2003/0091978 A1 | 5/2003 | Farrow et al. |

(Continued)

FOREIGN PATENT DOCUMENTS

| CA | 2281898 C | * | 3/2007 | .......... C07K 14/705 |
| CN | 104812901 A | * | 7/2015 | .......... C07K 14/005 |

(Continued)

OTHER PUBLICATIONS

English translation of CN104812901A (Year: 2015).*

(Continued)

*Primary Examiner* — M Franco G Salvoza
*Assistant Examiner* — Naghmeh Nina Moazzami
(74) *Attorney, Agent, or Firm* — Birch, Stewart, Kolasch & Birch, LLP

(57) ABSTRACT

The present invention provides a comprehensive assay capable of comprehensively measuring interactive factors for a variety of different types of proteins. In the present invention, provided is a system for detecting activation of a protein by integrating, with mediation of a plurality of factors, changes in the transcriptional regulatory region of a gene whose expression is changed by activation of the protein. The stimulation response ratio of transcription activity before and after stimulation by ligands possessed by individual transcriptional regulatory regions is synergistically integrated, so that a highly sensitive reporter assay system can be constructed.

5 Claims, 18 Drawing Sheets
Specification includes a Sequence Listing.

Reporter assay system constituted by multiple factors introduced exogenously

(51) Int. Cl.
  *C12N 15/62* (2006.01)
  *C12N 15/85* (2006.01)
  *C12Q 1/66* (2006.01)

(56) References Cited

U.S. PATENT DOCUMENTS

| | | |
|---|---|---|
| 2004/0235157 A1 | 11/2004 | Tovey et al. |
| 2005/0202403 A1 | 9/2005 | Fowlkes et al. |
| 2013/0198901 A1 | 8/2013 | Armstrong et al. |

FOREIGN PATENT DOCUMENTS

| | | | |
|---|---|---|---|
| EP | 2110666 B1 * | 12/2012 | ......... C12N 15/1055 |
| JP | 2006-507817 A | 3/2006 | |
| JP | 2016-149942 A | 8/2016 | |
| WO | WO 97/40170 A2 | 10/1997 | |
| WO | WO 01/55726 A1 | 8/2001 | |
| WO | WO 2005/007822 A2 | 1/2005 | |
| WO | WO 2007/092938 A2 | 8/2007 | |
| WO | WO 2015/128894 A1 | 9/2015 | |

OTHER PUBLICATIONS

Extended European Search Report for European Application No. 19844222.0, dated Jul. 11, 2022.
Galinski, "Multiplexed cell-based assays to profile GPCR activities and cellular signalling," Dissertation for Georg-August-University Göttingen, Feb. 25, 2016, pp. 1-129, URL: https://d-nb.info/1126724637/34.
Kotarsky et al., "Improved Reporter Gene Assays Used to Identify Ligands Acting on Orphan Seven-Transmembrane Receptors," Pharmacology & Toxicology, vol. 93, 2003, pp. 249-258.
Paguio et al., "Using luciferase reporter assays to screen for GPCR modulators," Cell Notes, Issue 16, 2006, pp. 22-25, URL: https://www.promega.de/-/media/files/resources/cell-notes/cn016/using-luciferase-reporter-assays-to-screen-for-gpcr-modulators.pdf?la=en.
Partial Supplementary European Search Report for European Application No. 19844222.0, dated Apr. 8, 2022.
Office Action issued Feb. 14, 2023, in Japanese Patent Application No. 2019-565957.
International Search Report issued Oct. 21, 2019, in PCT/JP2019/029424.

* cited by examiner

Fig.1 Reporter assay system constituted by multiple factors introduced exogenously

MEMBRANE PROTEIN ACTIVITY MEASUREMENT METHOD

TECHNICAL FIELD

The present invention relates to the searching or screening of substances that affect intracellular signal transduction. In some aspects, the present invention relates to a method for detecting receptor activation by a substance, and nucleic acids, systems, cells, proteins, compositions and the like, which are used in the aforementioned method.

BACKGROUND ART

To date, a large number of compounds have been placed on the market as products (e.g., pharmaceutical products), but a majority of these products target and act on some molecule (e.g., a receptor, a channel, a transporter, an enzyme, etc.) in living bodies. For example, a compound that has been found to act on a given target molecule in the development of pharmaceutical products is studied as a drug candidate in drug discovery. Researches in drug development require enormous costs, but on the other hand, the rate at which drug candidates can be actually used as pharmaceutical products is said to be 1/30,000, which is an extremely low rate.

The failure of the development of pharmaceutical products may be caused by unplanned effects of the compound acting on a molecule other than the intended molecule, and early exclusion of compounds having a potential development risk may have economic significance. For the early exclusion of such risky compounds, it is necessary to comprehensively verify the action of the compound to be developed on non-target molecules.

SUMMARY OF INVENTION

Solution to Problem

The present invention provides a comprehensive assay capable of comprehensively measuring interactive factors for a variety of different types of proteins (e.g., membrane proteins such as ion channels, G protein-coupled receptors (GPCRs), enzyme-linked receptors, ion channel-linked receptors, etc.).

More specifically, in the present invention, there is provided a system for detecting the activation of a protein by integrating changes in the transcriptional regulatory regions of genes whose expression is changed by activation of the protein (for example, by stimulation with a ligand or an ion) with mediation of a plurality of factors. The "stimulation response ratio of transcriptional activity before and after ligand stimulation" possessed by each transcriptional regulatory region is synergistically integrated, and a highly sensitive reporter assay system can be constructed.

In a certain aspect, the present invention provides a gene construct comprising first to Nth nucleotide sequences encoding first to Nth factors operably linked to the transcriptional regulatory regions of first to Nth genes whose expression is induced by activation of a protein responsible for signal transduction, wherein N is an integer of 2 or more. In one embodiment, this gene construct can be combined with a gene construct comprising a nucleotide sequence encoding a label that is configured so that its expression is triggered by at least one of the first to Nth factors. Each factor may improve the activity of at least one factor among the above-described first to Nth factors that are different from the concerned factor, and for example, each factor may increase the expression levels of other factors, or may be a substrate of a reaction catalyzed by other factors, or may catalyze a reaction generating the substrate.

In one embodiment, a cell membrane-bound transcription factor can be used as one of the factors. In addition, a protease can be used as one of the factors. The protease may be configured to cleave the cell membrane-bound transcription factor, thereby allowing the transcription factors to detach from the membrane and to translocate into the nucleus. Furthermore, a label whose expression is triggered by the above-described transcription factor can be used. As the label, a label used in the present technical field can be used without limitation, and an example may be luciferase. These constructs may be provided in the form of a kit.

In another aspect, the present invention provides a cell comprising the construct described in the present description. The cell can be used for investigating signal transduction into the cell due to the interaction between a test compound and a protein responsible for the signal transduction. In such a cell, the protein responsible for signal transduction may be overexpressed. As cells used herein, various types of cells can be used, as necessary. Since a membrane protein of interest is exogenously transfected, all types of cells can be used, in principle.

The cells of the present invention may be provided in a kit including a plurality of cells each expressing proteins responsible for different signal transductions. Such a kit is useful for comprehensively analyzing the interaction of a test compound with a plurality of proteins responsible for different signal transductions.

In some embodiments, as such proteins responsible for signal transduction, membrane proteins, such as, for example, receptors or channels, can be used. Preferably, the protein responsible for signal transduction is a GPCR. GPCRs are characterized in that they recognize a variety of ligands including low molecular substances, and it is said that approximately 40% of the target molecules of current pharmaceutical products are GPCRs. Investigation of the interaction of a compound with a GPCR and signal transduction from the GPCR via the G protein is extremely important for application of compounds.

In another aspect, the present invention also provides a chimeric G protein, a nucleic acid encoding the same, a cell expressing the same, and a method using the same. In the present description, a G protein α subunit that becomes a chimera and a chimeric G protein containing the same are provided. Since the coupling of the G protein with a receptor is determined by the amino acid sequence at the C-terminus of the Gα subunit, using a chimeric G protein, it becomes possible to detect activation of a GPCR coupled with a certain G protein by using an intracellular signal generated by activation of a different G protein. The present invention provides a chimeric G protein α subunit, in which the C-terminal amino acid sequence of a certain G12/13 α subunit is replaced with the amino acid sequence of a different G protein α subunit.

The chimeric G protein provided by the present invention can be used in a method for investigating the interaction between a test compound and a protein responsible for signal transduction described in the present description. The construct described herein can be used in combination with a chimeric G protein (or a construct encoding the same). For example, a chimeric G protein can be further expressed in a cell containing the above-described construct, and a signal from a GPCR coupled with a G protein other than G12/13

(e.g., Gs) can be detected in the same detection system as that for a signal from G12/13.

In another aspect, the present description discloses a method for identifying a gene whose expression is induced by activation of a protein responsible for signal transduction in a certain cell. The present method can be used for investigating the interaction between a protein responsible for signal transduction and a test compound. This method may comprise a step of obtaining the expression levels of a gene, when a cell expressing a protein is allowed to come into contact with an activator of the protein, a step of obtaining the expression levels of the gene, when the cell is not allowed to come into contact with the activator, and a step of selecting, as a candidate gene, a gene whose expression increases in the case of contacting with the activator compared with in the case of not contacting with the activator.

In one embodiment, in order to identify a gene whose expression is induced, a comparison among four groups can be performed based on the presence or absence of the expression of a protein and the presence or absence of an activator. A gene whose expression increases when a cell expressing a protein is allowed to come into contact with an activator can be selected as a candidate gene.

For example, in the present invention, the inventions specified in the following items are provided:

(Item 1) A construct or a combination of constructs for investigating the action of a test compound on a protein responsible for signal transduction, wherein the construct or the combination of constructs comprises:
first to Nth nucleotide sequences encoding first to Nth factors, respectively, which are operably linked to the transcriptional regulatory regions of first to Nth genes whose expression is induced by activation of the protein, wherein N is an integer of 2 or more.

(Item 2) A construct or a combination of constructs, comprising:
the construct or the combination of constructs according to the above item, and
a construct comprising a nucleotide sequence encoding a label that is configured so that its expression is triggered by at least one of the first to Nth factors.

(Item 3) A combination of constructs for investigating the action of a test compound on a protein responsible for signal transduction, comprising:
(1) a first construct in which the transcriptional regulatory region of a first gene is linked to a nucleotide sequence encoding a substrate (S) for an enzyme reaction;
(2) a second construct in which the transcriptional regulatory region of a second gene is linked to a nucleotide sequence encoding an enzyme (E1) for an enzyme reaction, wherein a product P1 is generated as a result of the enzyme reaction between S and E1;
with regard to each n that is a natural number of 3 to N, provided that N is 3 or more,
(n) an nth construct in which the transcriptional regulatory region of an nth gene is linked to a gene encoding an enzyme (E (n−1)) that produces a product (P (n−1)) using P (n−2) as a substrate; and
(N+1) a reporter gene construct that is configured so that a reporter gene is activated by a product P (N−1) of an enzyme reaction, wherein
the expression of each of an N number of first to Nth genes is induced by stimulation of the protein by the test compound, wherein N is a natural number of 2 or more and n is a natural number of 3 to N.

(Item 4) The construct or the combination of constructs according to any one of the above items, further comprising a construct encoding a chimeric G protein α subunit having an amino acid sequence, in which the amino acid sequence of the C-terminus in the amino acid sequence of a first Gα subunit belonging to Gα12/13 is replaced with the amino acid sequence of a Gα subunit different from the first Gα subunit.

(Item 5) A kit for investigating the action of a test compound on a protein responsible for signal transduction, including the construct or the combination of constructs according to any one of the above items.

(Item 6) The kit according to any one of the above items, further comprising a drug for introducing the construct into a cell.

(Item 7) A method for producing the construct, the combination of constructs, or the kit according to any one of the above items, comprising specifying the first to the Nth genes whose expression is induced by activation of the protein.

(Item 8) A cell comprising the construct or the combination of constructs according to any one of the above items.

(Item 9) A cell expressing a protein responsible for signal transduction, comprising:
first to Nth nucleotide sequences encoding first to Nth factors, respectively, which are operably linked to the transcriptional regulatory regions of first to Nth genes whose expression is induced by activation of the protein, and
a nucleotide sequence encoding a label that is configured so that its expression is triggered by at least one of the first to Nth factors, wherein N is an integer of 2 or more.

(Item 10) A cell expressing a protein responsible for signal transduction, comprising:
(1) a first construct in which the transcriptional regulatory region of a first gene is linked to a nucleotide sequence encoding a substrate (S) for an enzyme reaction;
(2) a second construct in which the transcriptional regulatory region of a second gene is linked to a nucleotide sequence encoding an enzyme (E1) for an enzyme reaction, wherein a product P1 is generated as a result of the enzyme reaction between S and E1;
with regard to each n that is a natural number of 3 to N, provided that N is 3 or more,
(n) an nth construct in which the transcriptional regulatory region of an nth gene is linked to a gene encoding an enzyme (E (n−1)) that produces a product (P (n−1)) using P (n−2) as a substrate; and
(N+1) a reporter gene construct that is configured so that a reporter gene is activated by a product P (N−1) of an enzyme reaction, wherein
the expression of each of an N number of first to Nth genes is induced by activation of the protein, wherein N is a natural number of 2 or more and n is a natural number of 3 to N.

(Item 11) A cell expressing a membrane protein, comprising:
a first nucleotide sequence encoding a first factor operably linked to the transcriptional regulatory region of a first gene whose expression is induced by activation of the membrane protein,
a second nucleotide sequence encoding a second factor operably linked to the transcriptional regulatory region of a second gene whose expression is induced by activation of the membrane protein, and a nucleotide sequence encoding a label that is configured so that its expression is triggered by the first factor, wherein the second factor is configured to trigger or promote the activity of the first factor to trigger the expression of the label.

(Item 11-1) The cell according to any one of the above items, wherein the first factor is a transcription factor.

(Item 11-2) The cell according to any one of the above items, wherein the transcription factor is configured to be expressed in an inactivated state.

(Item 11-3) The cell according to any one of the above items, wherein the transcription factor is a cell membrane-bound transcription factor.

(Item 11-4) The cell according to any one of the above items, wherein the second factor has the activity of dissociating the transcription factor from the cell membrane.

(Item 11-5) The cell according to any one of the above items, wherein the second factor is a protease.

(Item 11-6) The cell according to any one of the above items, wherein the cell membrane-bound transcription factor comprises a cleavable linker cleaved with the second factor between a cell membrane-bound portion and a transcription factor portion.

(Item 11-7) The cell according to any one of the above items, wherein the second factor is a cell membrane-type factor.

(Item 11-8) The cell according to any one of the above items, wherein the membrane protein is a G protein-coupled receptor, an enzyme-linked receptor, an ion channel-linked receptor, a channel, a transporter, or a cell adhesion molecule.

(Item 12) The cell according to any one of the above items, which comprises at least one selected from a HeLa cell, a HEK293 cell, a CHO cell, a COS-1/7 cell, an HL60 cell, a K562 cell, a Jurkat cell, a HepG2 cell, a Saos-2 cell, an F9 cell, a C2C12 cell, a PC12 cell, an NIH/3T3 cell, a U2OS cell, a Vero cell, an MDCK cell, an MEF cell, a U937 cell, a 6 cell, a Neuro2A cell, an SK-N-MC cell, an SK-N-SH cell, a HUVEC cell, a THP-1 cell, a BW5147 cell, a Ba/F3 cell, a Y-1 cell, an H295R cell, a MIN6 cell, a NIT-1 cell, and an MDA-MB435S cell.

(Item 12A) The cell according to any one of the above items, which is a HeLa cell or a HEK293T cell.

(Item 13) The cell according to any one of the above items, wherein the gene is selected from the group consisting of ARC, CCL20, CTGF, DUSP5, EGR1, EGR2, EGR3, FOSB, NR4A1, NR4A3, CYR61, and FOS.

(Item 13A) The cell according to any one of the above items, wherein the first gene is NR4A1.

(Item 13B) The cell according to any one of the above items, wherein the second gene is CTGF.

(Item 13C) The cell according to any one of the above items, wherein the first gene is FOS.

(Item 13D) The cell according to any one of the above items, wherein the second gene is FOSB.

(Item 14) A HeLa cell or a HEK293T cell that expresses a membrane protein, the cell comprising:

a first nucleotide sequence operably linked to the transcriptional regulatory region of a first gene whose expression is induced by activation of the membrane protein, the first nucleotide sequence encoding a cell membrane-bound transcription factor, a second nucleotide sequence operably linked to the transcriptional regulatory region of a second gene whose expression is induced by activation of the membrane protein, the second nucleotide sequence encoding a protease, and a nucleotide sequence encoding luciferase that is configured so that its expression is triggered by the transcription factor, wherein the membrane protein is a G protein-coupled receptor (GPCR), an enzyme-linked receptor, an ion channel-linked receptor, or a channel, the cell membrane-bound transcription factor comprises a cleavable linker cleaved with the protease between a cell membrane-bound portion and a transcription factor portion, and when the cell is a HeLa cell, the first gene is NR4A1 and the second gene is CTGF, and when the cell is a HEK293T cell, the first gene is FOS and the second gene is FOSB.

(Item 15) The cell according to any one of the above items, which comprises a chimeric G protein α subunit having an amino acid sequence, in which the amino acid sequence of the C-terminus in the amino acid sequence of a first Gα subunit belonging to Gα12/13 is replaced with the amino acid sequence of a Gα subunit different from the first Gα subunit.

(Item 16) A kit including a plurality of cells each expressing a different membrane protein, wherein each of the plurality of cells is the cell according to any one of the above items.

(Item 17) The kit according to any one of the above items, for comprehensively analyzing the action of a test compound on a membrane protein.

(Item 18) A method for analyzing the action of a test compound on a membrane protein, which is characterized in that it uses the cell according to any one of the above items or the kit according to any one of the above items.

(Item 19) A method for producing the cell according to any one of the above items, comprising:

a step of transfecting a cell with the membrane protein or GPCR, and a step of introducing the first to Nth nucleotides into the gene loci of the first to Nth genes, so that they are operably linked to the transcriptional regulatory regions of individual genes.

(Item 20) A chimeric G protein α subunit having an amino acid sequence, in which the amino acid sequence of the C-terminus in the amino acid sequence of a first Gα subunit belonging to Gα12/13t is replaced with the amino acid sequence of a Gα subunit different from the first Gα subunit.

(Item 21) The chimeric G protein α subunit according to the above item, wherein the different Gα is Gαs.

(Item 22) The chimeric G protein α subunit according to any one of the above items, wherein, in the amino acid sequence of the first Gα subunit, approximately 6 amino acids at the C-terminus are replaced with the amino acid sequence of the different Gα subunit.

(Item 23) A chimeric G protein comprising the chimeric G protein α subunit according to any one of the above items.

(Item 24) A conjugate comprising the chimeric G protein according to any one of the above items and a G protein-coupled receptor (GPCR) coupled with the chimeric G protein.

(Item 25) A cell comprising the conjugate according to any one of the above items.

(Item 26) The cell according to any one of the above items, further comprising the construct according to any one of the above items.

(Item 27) A composition comprising the cell according to any one of the above items, which is for use in the functional analysis of a GPCR.

(Item 28) A construct for use in the functional analysis of the GPCR of a cell, wherein the construct is configured to express a chimeric G protein α subunit comprising a nucleotide sequence encoding at least a portion of a G protein subunit α12 and a nucleotide sequence encoding at least a portion of a G protein α subunit that is different from the Gα12 to be replaced, and having an amino acid sequence that is replaced with the amino acid sequence of a G protein α subunit different from Gα12, in which the amino acid sequence at the C terminus in the amino acid sequence of the Gα12 is to be replaced.

(Item 29) A method for identifying a gene whose expression in a certain cell is induced by activation of a protein responsible for signal transduction, so as to investigate the action of a test compound on the protein, comprising:
  a step of obtaining the expression level of the gene, when the cell expressing the protein is allowed to come into contact with an activator of the protein,
  a step of obtaining the expression level of the gene, when the cell is not allowed to come into contact with the activator, and
  a step of selecting, as a candidate gene, a gene whose expression increases in the case of contacting with the activator compared with in the case of not contacting with the activator.

(Item 30) A method for identifying a gene whose expression in a certain cell is induced by activation of a protein responsible for signal transduction, comprising:
  a step of obtaining the expression level of the gene, when the cell expressing the protein is allowed to come into contact with an activator of the protein,
  a step of obtaining the expression level of the gene, when the cell expressing the protein is not allowed to come into contact with the activator,
  a step of obtaining the expression level of the gene, when the cell not expressing the protein is allowed to come into contact with the activator,
  a step of obtaining the expression level of the gene, when the cell not expressing the protein is not allowed to come into contact with the activator, and
  a step of selecting, as a candidate gene, a gene whose expression increases in the case where the cell expressing the protein is allowed to come into contact with the activator of the protein, compared with other cases.

(Item 31) The method according to any one of the above items, wherein the protein is GPCR that is specifically coupled with the G protein G12/13.

(Item 32) The method according to any one of the above items for producing the cell according to any one of the items 9 to 15, further comprising a step of introducing a nucleotide sequence into the cell, so that the nucleotide sequence is operably linked to the transcriptional regulatory region of the candidate gene.

Advantageous Effects of Invention

The present invention enables a comprehensive assay of a target protein, which has not been conventionally realized. In particular, when the target protein is a GPCR, even if the GPCR is any of the following types, namely, a "Gs-coupled GPCR," a "Gq-coupled GPCR," a "Gi-coupled GPCR," and a "G12/13-coupled GPCR," it has become possible to comprehensively assay regulators such as the ligands, agonists or antagonists thereof. In the screening of the ligand activity of a compound, the present invention can provide an assay system that is more excellent than the existing cell-based assays, in terms of sensitivity, S/N ratio, comprehensiveness, and/or costs. In particular, regarding GPCRs, the present invention can monitor all of the GPCRs under a single assay format.

DESCRIPTION OF EMBODIMENTS

Figure 1:
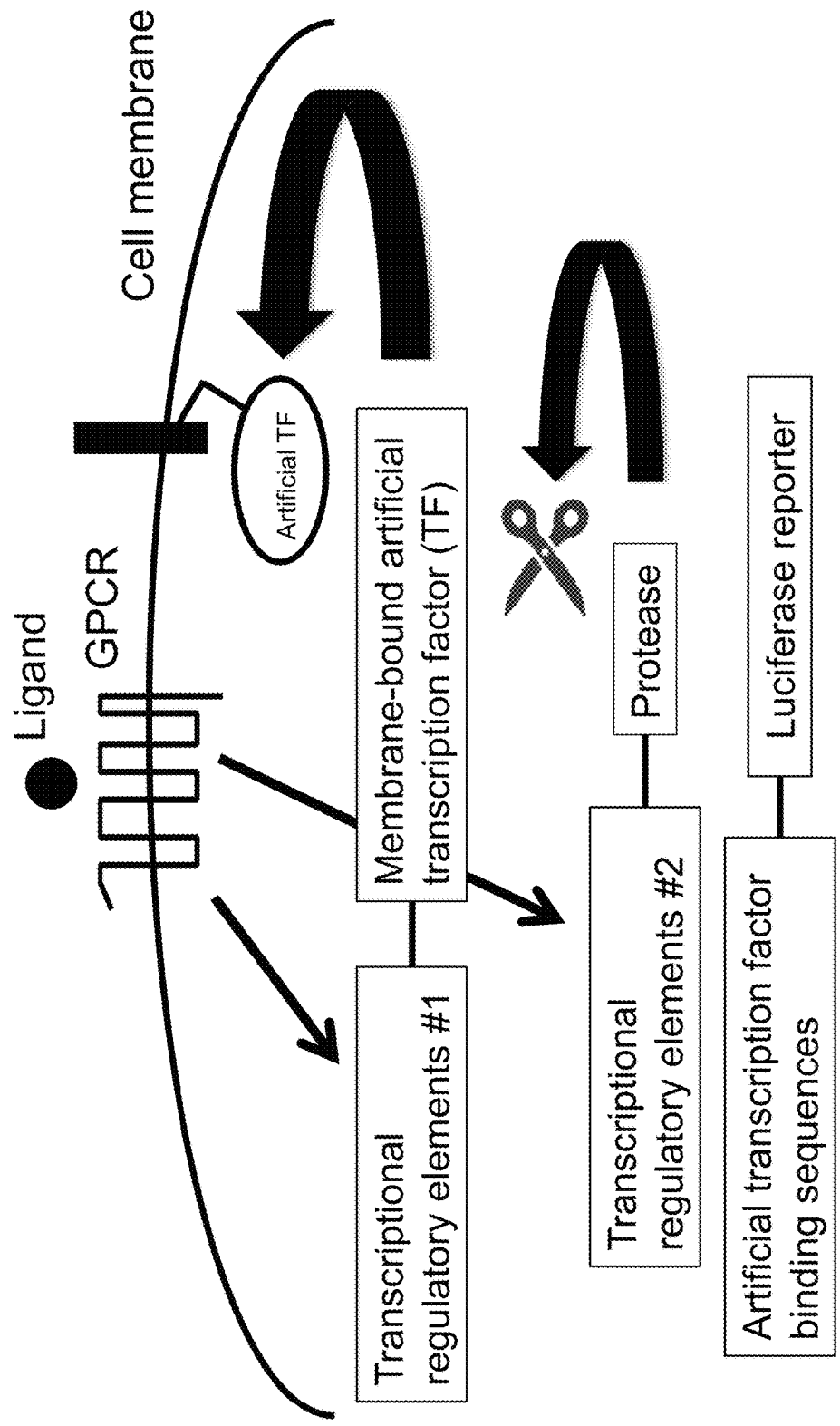
FIG. 1 is a schematic figure showing the mechanism of measuring ligand activity using the construct of the present invention. A reporter gene (e.g., luciferase) and a target receptor gene plasmid are introduced into cells. It is configured that a membrane-bound artificial transcription factor and a protease are induced to be expressed by receptor stimulation. This can be realized by exogenously introducing a construct operably linked to the transcriptional regulatory region of a gene whose expression is induced by receptor stimulation into cells.

Hereinafter, the present invention will be described with reference to the best mode. It should be understood that, throughout the present description as a whole, singular terms include the plural concepts thereof, unless otherwise particularly specified. Accordingly, it should be understood that singular articles (e.g., "a," "an," "the," etc. in English) also include the plural concepts thereof, unless otherwise particularly specified. In addition, it should also be understood that the terms used in the present description are used to have meanings commonly used in the present technical field, unless otherwise particularly specified. Thus, unless otherwise defined, all technical and scientific terms used herein have the same meanings as those commonly understood by a skilled person in the present technical field, to which this invention belongs. In the case of contraction, the present description (including definitions) has priority.

(1) Outlines

Activation of a plurality of intracellular signal transduction pathways occurring in the same time phase after a ligand has bound to a membrane protein expressed in a cell membrane, namely, activation of a certain membrane protein, and the expression of a plurality of different genes occurring downstream thereof at almost the same time after the activation, will be discussed below.

In general, the binding of a ligand to a membrane protein activates a gene transcriptional regulatory region in a cell, and a gene downstream thereof is thereby expressed, and a protein encoded by such a gene is then generated. Among the genes whose expression is induced in this way, our attention is paid, in particular, to the presence of a plurality of independent genes whose expression is induced at almost the same time (wherein these genes are referred to as gene 1, gene 2, gene 3, and further, gene N, and the transcriptional regulatory regions of these genes are referred to as transcriptional regulatory region 1, transcriptional regulatory region 2, transcriptional regulatory region 3, and further, transcriptional regulatory region N, respectively).

In the present invention, a construct 1, in which a first target gene (a gene encoding a first factor), instead of a gene 1, is linked downstream of a transcriptional regulatory region 1, is constructed, and also, a construct 2, in which a second target gene (a gene encoding a second factor), instead of a gene 2, is linked downstream of a transcriptional regulatory region 2, is constructed. These constructs are introduced into cells.

As shown in FIG. 1, when a protein 1 is set to be a cell membrane-bound artificial transcription factor having a protease cleavage region and when a protein 2 is set to be a protease, signal transduction occurs by the binding of a ligand to a membrane protein (for example, a GPCR), and the transcriptional regulatory region 1 functions to express the cell membrane-bound artificial transcription factor, and the expressed and generated transcription factor binds to the cell membrane. At this stage, this transcription factor is inactive because it remains bound to the cell membrane.

Next, when the transcriptional regulatory region 2 functions and the protein 2 (protease) is thereby expressed at the same time, independently or in parallel with the activation of the transcriptional regulatory region 1 by the above-described signal transduction, the protease acts on the protease cleavage region linked to the above-described transcription factor, so as to separate the transcription factor from the cell membrane. The transcription factor separated from the cell membrane is translocated into the nucleus and becomes active.

A construct (which is referred to as an "artificial transcription factor binding sequence-luciferase reporter" in FIG. 1), in which a sequence to which this active transcription factor binds (an artificial transcription factor binding sequence) is linked to a reporter gene, is produced, and this construct, together with the construct 1 and the construct 2, is introduced into cells, so that the separated transcription factor, as described above, binds to the artificial transcription factor binding sequence, and a reporter gene located downstream thereof is expressed.

Eventually, since the action of the ligand on the membrane protein is converted to a product of the degree of activation of a plurality of signal transduction pathways generated by the binding of the ligand to the membrane protein, if the expression of a reporter gene in a construct in which the reporter gene is present is detected by light emission, etc., a synergistically amplified output can be obtained. Thus, since the ligand corresponds to the test compound, a construct is appropriately constructed depending on the purpose of the combination of a compound to be tested and a membrane protein, and is then introduced into cells, so that the action of the test compound on the membrane protein can be investigated with high sensitivity, using the expression of the reporter gene as an indicator.

In the present invention, the genes associated with the signal transduction pathways are not limited to the expression of the above genes 1 and 2, but may be associated with the 3rd gene, . . . , and Nth genes. Hence, in the present invention, in order to examine how the test compound influences on the above-described system, provided herein are constructs, in which nucleotide sequences encoding first to Nth factors (which are referred to as first to Nth nucleotide sequences, respectively) are each operably linked to the transcriptional regulatory regions of an N number of genes (1st to Nth genes) whose expression is induced at the same time phase by the activation of the membrane protein, or a combination of these constructs.

2. Definitions

Hereinafter, the definitions and/or the basic technical contents of the terms particularly used in the present description will be described, as appropriate.

In the present description, a molecule "responsible for signal transduction" means any given molecule whose change brings on a change in another molecule. Examples of such a molecule may include, but are not limited to, receptors such as G protein-coupled receptors and ion channels.

In the present description, "the expression of a certain gene is induced" by a certain event means that a difference, preferably, a significant difference is generated between the expression level of the gene when the event occurs and the expression level of the gene when the event does not occur.

In the present description, the term "construct" means one or more nucleic acids having a certain structure, and preferably, non-naturally occurring ones. Unless explicitly specified, the term "construct" means one or more constructs. The constructs are not limited to those that are isolated per se, but may also mean a portion having a non-naturally occurring structure comprising a foreign sequence, in a case where the foreign sequence is inserted into a longer nucleic acid (e.g., genomic DNA).

In the present description, the term "chimera" means a polypeptide comprising all or a part of a first protein and all or a part of a second protein different from the first protein. The chimera used in the present description may be the first protein, a part of which is replaced with a corresponding portion of the second protein.

In the present description, the term "activity" means the function of a molecule in the broadest sense in the present technical field. The term "activity" generally includes, but is not limited to, the biological, biochemical, physical or chemical function of a molecule. Examples of the activity may include enzyme activity, the ability to interact with other molecules, the ability to activate, promote, stabilize, inhibit, suppress or destabilize the function of other molecules, stability, and the ability to localize in a specific position in a cell.

In the present description, the term "activation" generally means that a living body or a biological substance exhibits its function. Activation of a protein means that the protein increases its activity level by some kind of stimulation or spontaneously, and exhibits some function. As a result of activation, various biological phenomena such as, for example, signal transduction, occur.

In the present description, the "expression" of a gene, a polynucleotide, a polypeptide or the like means that the gene or the like undergoes a certain action in vivo, so that it takes another form. Preferably, it means that a gene, a polynucleotide, or the like is transcribed and translated, so that it takes the form of a polypeptide. However, production of mRNA as a result of transcription is also an aspect of the expression. Accordingly, the term "expression product" is used in the present description to include such a polypeptide or protein, or mRNA. More preferably, the form of such a polypeptide may be as a result of undergoing post-translational processing.

In the present description, the term "transcriptional regulatory region" is a sequence capable of regulating transcription initiation or transcription efficiency, and examples of the transcriptional regulatory region may include a promoter, an enhancer, a responsive element, and a silencer.

In the present description, the term "label" means a substance (e.g., a substance that generates a substance, energy, an electromagnetic wave, or a certain type of optical signal, etc.) for distinguishing a target molecule or substance from other molecules or substances. Examples of the label used in the present invention may include, but are not limited to, luciferase, fluorescent proteins such as a green fluorescent protein (GFP), beta-galactosidase, beta-lactamase, alkaline phosphatase, and beta-glucuronidase. In the present invention, the target of interest can be modified utilizing such a label, so that the target can be detected by a detection means used. Such modifications are known in the present technical field, and those skilled in the art can implement such methods, as appropriate, depending on the label or the target of interest.

In the present description, the term "enzyme" is understood in a broad sense and is a general term for proteins that catalyze any given reactions. The enzyme is neither changed nor decomposed by itself, and mediates or promotes a chemical change in a living body. A substance that reacts with an enzyme is called a "substrate," and in the present description, the "substrate" is understood in the broadest sense. For each enzyme, what substance is used as a substrate and to what the substrate is changed are determined, and this is called enzyme specificity. In the present invention, such specificity can be utilized.

In the present description, the term "introduction" means introduction of a nucleic acid or the like into cells. Such introduction can be realized by transformation, transfection, conjugation, protoplast fusion, electroporation, particle gun technology, calcium phosphate precipitation, *Agrobacterium* method, direct microinjection, etc.

In the present description, the term "transcription factor" means a protein or a polypeptide that binds to a specific DNA sequence associated with a genomic locus or a gene of interest, in order to regulate transcription. The transcription factor can promote (as an activator) or block (as a repressor) the recruitment of RNA polymerase to the gene of interest. The transcription factor can perform its function alone or as apart of a larger protein conjugate. The mechanisms of gene regulation used by transcription factors include: a) stabilizing or destabilizing RNA polymerase binding, b) acetylation or deacetylation of histone proteins, and c) recruitment of coactivator or corepressor proteins, but are not limited thereto. Moreover, the transcription factor plays a role in biological activities including, but not limited to, basal transcription, reinforcement of transcription, development, response to intercellular signal transduction, response to environmental signals, cell cycle control, and pathogenesis. For information regarding transcription factors, please refer to: Latchman and DS (1997) Int. J. Biochem. Cell Biol. 29 (12): 1305-12; Lee T I, Young R A (2000), which is incorporated herein by reference in its entirety. References are made to Annu. Rev. Genet. 34: 77-137, and Mitchell P J, Tjian R (1989) Science 245 (4916): 371-8. The cell membrane-bound transcription factor is an artificial transcription factor having a structure localized in the cell membrane. Examples of possible configurations of the cell membrane-bound transcription factor may include, but are not limited to, linking to the intracellular domain of a cell membrane protein, and anchoring to the cell membrane from the inside of a cell via lipid modification, such as palmitoylation.

In the present description, the term "cell membrane-type" or "membrane type" means that a factor comprises any given structure localized in the cell membrane or is linked to such a structure.

In the present description, the term "protease" is also called a proteolytic enzyme, and is a general term for enzymes that catalyze a reaction that hydrolyzes a peptide bond of a protein or the like.

In the present description, the term "membrane protein" means a protein present inside of or on the outer surface of a cell membrane. The membrane protein is embedded in the cell membrane or loosely binds to the cell membrane.

In the present description, the term "gene" means a factor that determines genetic traits, and the term "gene" may mean a "polynucleotide," an "oligonucleotide," and a "nucleic acid."

In the present description, the terms "protein," "polypeptide," "oligopeptide," and "peptide" are used to have the same meanings, and all of them mean an amino acid polymer having any given length. This polymer may be linear, branched, or cyclic. The amino acids may be natural or non-natural, and may also be modified amino acids. This term may also include those assembled into a conjugate of multiple polypeptide chains. This term may further include natural or artificially modified amino acid polymers. This definition may also include, for example, polypeptides containing one or two or more analogs of amino acids (e.g., including unnatural amino acids, etc.), peptide-like compounds (e.g., peptoids), and other modifications known in the present technical field. When the polypeptide according to the embodiment of the present invention comprises a "specific amino acid sequence," any of amino acids in the amino acid sequence may be chemically modified. Further, any of the amino acids in the amino acid sequence may form a salt or a solvate. Further, any of the amino acids in the amino acid sequence may be L-type or D-type. Even in such cases, it can be said that the protein according to the embodiment of the present invention comprises the above "specific amino acid sequence."

In the present description, the terms "polynucleotide," "oligonucleotide," and "nucleic acid" have the same meanings, and all of them mean a nucleotide polymer having any given length. This term also includes an "oligonucleotide derivative" or a "polynucleotide derivative." The term "oligonucleotide derivative" or "polynucleotide derivative" means an oligonucleotide or a polynucleotide, which contains nucleotide derivatives or involves unusual bonds between nucleotides, and these terms are used interchangeably. Unless otherwise indicated, a specific nucleic acid sequence is also intended to include conservatively modified variants (e.g., degenerate codon substitutions) and complementary sequences thereof, as well as explicitly stated sequences. In the present description, the term "nucleic acid" is also used interchangeably with the terms gene, cDNA, mRNA, oligonucleotide, and polynucleotide. In the present description, the term "nucleotide" may be either natural or non-natural.

In the present description, the "homology" of a gene means the degree of identity between two or more gene sequences, and in general, to have "homology" means that the degree of identity or similarity is high. Any given protein, nucleic acid or gene used in the present invention may be a protein, a nucleic acid or a gene comprising a specifically referred specific sequence or a sequence having homology to the specific sequence, and for example, it may be encoded by a nucleic acid having homology to the nucleic acid encoding the protein specifically described in the present specification. Whether or not two types of genes have homology to each other can be determined by a direct sequence comparison, or in the case of a nucleic acid, by a hybridization method performed under stringent conditions. When two gene sequences are directly compared, if the DNA sequences between the gene sequences typically have identity of at least 50%, preferably at least 70%, more preferably at least 80%, 90%, 95%, 96%, 97%, 98% or 99%, the genes are homologous to each other.

In the present description, the term "functional equivalent" means any given entity that has the same function of interest as the original entity as a target but has a different structure from the original entity. Any given protein or nucleic acid used in the present invention may preferably be a functional equivalent of the protein or nucleic acid specifically described in the present description. As the functional equivalent of the present invention, a protein having an amino acid sequence comprising an insertion, substitution or deletion of one or more amino acids, or addition of one or more amino acids to either one or both termini, of the original amino acid sequence, can be used. The modified amino acid sequence may be, for example, an amino acid sequence comprising an insertion, substitution or deletion of, for example, 1 to 30, preferably 1 to 20, more preferably 1 to 9, further preferably 1 to 5, and particularly preferably 1 or 2 amino acids, or addition thereof to either one or both termini, of the original amino acid sequence. It may also be an amino acid sequence having a conservative substitution of one or more (preferably 1 or several, or 1, 2, 3 or 4) amino acids. The term "conservative substitution" is used herein to mean that one or more amino acid residues are substituted with another (other) chemically similar amino acid residue(s), so as not to substantially modify the function of the protein. Functionally similar amino acids that can be used in such substitution are known for every amino acid in the present technical field.

Amino acids may be indicated herein with either their commonly known three-letter symbols or with the one-letter symbols recommended by IUPAC-IUB Biochemical Nomenclature Commission. Likewise, nucleotides may also be indicated herein with their generally recognized one-letter codes. In the present description, comparisons of similarity, identity and homology between amino acid sequences or between nucleotide sequences are calculated with BLAST, a tool for sequence analysis, using default parameters. Search for the identity can be performed using, for example, BLAST 2.2.28 (issued in 2013.4.2) of NCBI. In the present description, the value of identity usually means a value obtained by performing alignment under default conditions, using the above-mentioned BLAST. However, if higher values are output due to changes in the parameters, the highest value is used as a value of the identity. When the identity is evaluated in a plurality of areas, the highest value among them is set to be an identity value. Similarity is a numerical value calculated for similar amino acids, in addition to identity.

In one embodiment of the present invention, "several" may be, for example, 10, 8, 6, 5, 4, 3, or 2, or may also be less than any of those values. It has been known that a polypeptide, in which one or several amino acid residues have been deleted, added, inserted, or substituted with other amino acids, maintains its biological activity (Mark et al., Proc. Natl Acad Sci USA 1984 September; 81 (18): 5566-5666, Zoller et al., Nucleic Acids Res. 1982 Oct. 25; 10 (20): 6487-6500, and Wang et al., Science. 29; 224 (4656): 1431-1433). It is possible to select a protein having the same activity as that of a wild-type protein from mutant-type proteins, into which a deletion or the like has been introduced, by performing various types of characterizations such as FACS analysis or ELISA.

In one embodiment of the present invention, "90% or more" may be, for example, 90%, 95%, 96%, 97%, 98%, 99%, or 100% or more, or may further be within the range of any two values as mentioned above. The "homology" may be obtained by calculating the ratio of the number of homologous amino acids in two or more amino acid sequences according to a method known in the present technical field. Before calculation of the ratio, the amino acid sequences of amino acid sequence groups to be compared are aligned, and in order to maximize the ratio of identical amino acids, a gap is introduced in a part of the amino acid sequence, as necessary. The method for alignment, the method of calculating the ratio, the comparison method, and relevant computer programs have been conventionally well known in the present technical field (e.g., BLAST, GENETYX, etc.). In the present description, the "homology" can be represented with a value measured by NCBI BLAST, unless otherwise specified. As an algorithm used in comparison of amino acid sequences using BLAST, Blastp can be used with default setting. The measurement results are quantified as Positives or Identities.

When the present invention refers to a biomolecule or a substance (a protein, a nucleic acid, etc.), the biomolecule or the substance can preferably be a "purified" or "isolated" biomolecule or substance. In the present description, the "purified" substance or biological factor (e.g., a nucleic acid, a protein, etc.) means a substance or a biological factor, from which at least a part of a factor naturally accompanying with the substance or the biological factor has been removed. The term "purified" used in the present description means that preferably at least 75% by weight of, more preferably at least 85% by weight of, further preferably at least 95% by weight of, and most preferably at least 98% by weight of the same type of biological factor is present. The substance or the biological factor used in the present invention is preferably a "purified" substance. The "isolated" substance or biological factor (e.g., a nucleic acid, a protein, etc.) used in the present description means a substance or a biological factor, from which a factor naturally accompanying with the substance or the biological factor has been removed. The degree indicated with the term "isolated" used in the present description is fluctuated depending on the purpose. Thus, the degree of isolation is not necessarily indicated by purity. However, if necessary, it means that preferably at least 75% by weight of, more preferably at least 85% of, further preferably at least 95% of, and most preferably at least 98% by weight of the same type of biological factor is present. The substance used in the present invention is preferably an "isolated" substance or biological factor.

In the present description, the term "fragment" means a polypeptide or a polynucleotide having a sequence length of 1 to n−1 with respect to a full-length polypeptide or polynucleotide (wherein the length is n). In the present invention, for example, the nucleotide sequence used in the construct may be a fragment of another factor. Alternatively, in the present invention, when a chimeric molecule is envisioned, the chimeric molecule may be a combination of a fragment of one element and a fragment of another element. The length of the fragment can be appropriately changed depending on the purpose. For example, in the case of a polypeptide, the lower limit of the length is 3, 4, 5, 6, 7, 8, 9, 10, 15, 20, 25, 30, 40, 50 or more amino acids. In addition, lengths represented by integers that are not specifically recited herein (e.g., 11 amino acids, etc.) may also be suitable as lower limits. On the other hand, in the case of a polynucleotide, the length may be 5, 6, 7, 8, 9, 10, 15, 20, 25, 30, 40, 50, 75, 100 or more nucleotides. In addition, lengths represented by integers that are not specifically recited herein (e.g., 11 nucleotides, etc.) may also be suitable as lower limits.

The "cleavable linker" used in the present description is any given linker that is cleaved with a protease, and examples of the cleavable linker include linkers that are specifically cleaved because they have specific amino acid sequences.

In the present description, the term "approximately" means that a fluctuation of ±10% of the indicated value is acceptable. In the present description, when it is clearly specified that "within the range" of "two values," the range includes the two values themselves.

3. Molecule Responsible for Signal Transduction

The present invention provides a means for investigating the action of a compound on a molecule responsible for signal transduction. Herein, the molecule responsible for signal transduction is not particularly limited, as long as it transmits signals to a site downstream thereof by activation of the molecule. The molecule responsible for signal transduction may be a molecule on which a test compound acts directly (e.g., a receptor itself), or may also be a molecule that is activated by signal transduction from a molecule on which a test compound has acted, and then transmits signals to a site downstream thereof (e.g., a protein coupled with a receptor). As a molecule responsible for signal transmission, a molecule that induces the expression of some gene downstream thereof can be used. Examples of the molecule responsible for signal transduction may include proteins, nucleic acids, lipids, sugars, and conjugates thereof. The molecule responsible for signal transduction is preferably a protein responsible for signal transduction.

The molecule responsible for signal transduction may be a membrane protein that responds to stimulation by an extracellular ligand and then transmits signals into a cell. Examples of the membrane protein may include receptors (GPCRs, enzyme-linked receptors, ion channel-linked receptors, etc.), channels, transporters, and cell adhesion molecules.

In one embodiment, the protein responsible for signal transduction is a GPCR or a G protein coupled with the GPCR. It is said that a total of approximately 1,000 types of GPCRs are present on the genome. Among them, there are approximately 300 types of receptors other than odorant receptors (which recognize physiologically active substances), and there are approximately 100 types of receptors whose ligands (substances that activate receptors) are unknown (i.e., orphan receptors). In one embodiment of the invention, the GPCR may be a non-odorant GPCR.

GPCRs are each coupled with predetermined G proteins, and signal transduction into cells can be realized by transmitting the activation of the GPCRs to the G proteins. GPCRs are considered to be a group of receptor molecules having a characteristic seven-transmembrane structure. A receptor stimulated by a ligand transmits signals into cells via a heterotrimeric GTP-binding protein (G protein composed of three subunits $\alpha$, $\beta$ and $\gamma$). The G proteins are broadly classified into Gs, Gi, Gq and G12/13 based on the sequence of the $\alpha$ subunit, whereas the GPCRs are classified into four groups, namely, "Gs-coupled GPCR," "Gq-coupled GPCR," "Gi-coupled GPCR," and "G12/13-coupled GPCR." In the present description, the G proteins in each group may be simply referred to as Gs, Gi, Gq, and G12/13, at times. In addition, mouse and rat GPCRs are highly homologous to human GPCRs at the amino acid level (85% or more), but often significant differences are observed in terms of the way of being activated by artificial ligands. If it is desired to know the action of the ligand on a human GPCR, such a human GPCR may be preferably used.

These G proteins transmit signals to a site downstream thereof in different ways. The "s" of Gs is derived from activation (stimulation), and Gs initiates the subsequent signaling cascade by activating a membrane enzyme, adenylate cyclase. In addition, Gs activates phospholipase A2, phospholipase C or the like to transmit signals into cells. cAMP produced by the activated adenylate cyclase activates protein kinase A. Gi is also referred to as Gi/o, and "i/o" means acronyms for inhibition/other. Since Gi often inhibits the activity of adenylate cyclase, it suppresses signals derived from Gs. In addition, Gi is involved in a wide range of signal transduction systems, such as activation of phosphatidylinositol-specific phospholipase C$\beta$ and phosphodiesterase via a $\beta\gamma$ subunit. Gq performs signal transduction by activating phospholipase C$\beta$. G12/13 cross-talks with a signal transduction system via low-molecular-weight G proteins Ras and Rho.

GPCRs are also referred to as a group of receptor molecules that are targeted by approximately 40% of marketed pharmaceutical products, and it is greatly significant to observe GPCR activation by compounds. When a G protein is activated by GPCR stimulation, the amount of second messengers in cells is changed. Thus, there is a method for evaluating the activated state of a GPCR by measuring the amount of the second messengers. However, this method is problematic in terms of screening efficiency and costs.

As an index for evaluating the activated state of a cell membrane receptor molecule including a GPCR, a receptor to be evaluated is overexpressed in animal cells, and changes in various gene expressions triggered when the cells are stimulated by a ligand are often utilized. When change of the expression levels of a gene before and after ligand stimulation is quantified, the experimental technique of directly measuring an mRNA or a protein produced by the gene is complicated, and thus, this technique is not suitable for a screening operation involving a large number of specimens. Hence, in general, a reporter assay using an exogenous reporter gene plasmid is carried out, instead of the aforementioned experimental technique.

A reporter assay can be constructed as follows.
1) In a cell in which a receptor to be evaluated is overexpressed, a gene group whose expression levels are significantly increased before and after ligand stimulation is identified.
2) A gene having a high stimulation response ratio (expression levels after ligand stimulation/expression levels before ligand stimulation) is selected from this gene group, and the transcriptional regulatory region of the gene is identified.
3) The identified transcriptional regulatory region is cloned, and an artificial gene (an exogenous reporter gene plasmid) having a reporter gene (e.g., luciferase) linked downstream thereof is then prepared.
4) The above-described artificial gene is exogenously transfected into a cell in which the receptor to be evaluated has been overexpressed, and the activity of the exogenous reporter gene product is then measured before and after ligand stimulation.

The reporter assay is overwhelmingly simple, compared with actual quantification of an mRNA or a protein. However, when there are no gene groups whose expression levels are significantly increased before and after ligand stimulation, or even if there is such a gene group, when it has a low stimulation response ratio, it becomes difficult to construct a highly sensitive reporter assay system.

Therefore, in order to monitor the activated state of the GPCR (the activated state of the G protein), it is most convenient and efficient to detect the activated state by a reporter assay. However, a good reporter capable of monitoring the activated state of G12/13 and Gi/o (an expression fluctuating gene) has not been known. In order to monitor G12/13 activation or Gi/o activation by a reporter assay, the improvement of the reporter assay has been needed. In addition, although it has been reported that Gs activation could be monitored, for example, by the CRE-reporter system, it has been found that activation of some Gs-coupled GPCRs could not be detected by the CRE-reporter system (See FIG. 10). Hence, a system capable of monitoring all of Gs-coupled GPCRs has been required.

Moreover, each G protein has different modes of downstream signal transduction, depending on the types thereof, and thus, the G proteins cannot be monitored by the unified reporter assay system, as described above. Accordingly, it has been difficult to search for ligands of orphan GPCRs whose ligands are unknown.

In the present invention, the transcriptional regulatory regions of a plurality of genes whose expression is induced after stimulation of a receptor with a ligand are operably linked to one another by intervening an enzyme reaction, thereby providing a highly sensitive reporter assay system, in which the "stimulation response ratio of transcriptional activity before and after ligand stimulation" of each transcriptional regulatory region is synergistically integrated. By using the assay system of the present invention, various GPCRs coupled with all types of G proteins, namely, Gs, Gi, Gq, and G12/13, can be uniformly assayed.

Besides, the GPCRs that can be analyzed in the present invention may be one or more of the following, and may be preferably substantially all of the following.

TABLE 1-1

|    | #1-#20 | #21-#40 | #41-#60 | #61-#80 | #81-#100 | #101-#120 | #121-#140 | #141-#160 |
|----|--------|---------|---------|---------|----------|-----------|-----------|-----------|
| 1  | HTR1A  | ADORA3  | CALCRL  | ACKR4(CCR11) | DRD1 | GALR2 | GPR109B | MCHR2 |
| 2  | HTR1B  | ADRA1A  | CASR    | CCRL2   | DRD2     | GALR3     | KISS1R    | MC1R |
| 3  | HTR1D  | ADRA1B  | GPRC6A  | ACKR1 (CCBP1) | DRD3 | GPR151(GALR4) | LTB4R | MC2R |
| 4  | HTR1E  | ADRA1D  | CNR1    | ACKR2(CCBP2) | DRD4 | GHSR | LTB4R2 | MC3R |
| 5  | HTR1F  | ADRA2A  | CNR2    | CXCR1   | DRD5     | GHRHR     | CYSLTR1   | MC4R |
| 6  | HTR2A  | ADRA2B  | GPR18   | CXCR2   | EDNRA    | GIPR      | CYSLTR2   | MC5R |
| 7  | HTR2B  | ADRA2C  | GPR55   | CXCR3   | EDNRB    | GLP1R     | OXER1(GPR170) | MTNR1A |
| 8  | HTR2C  | ADRB1   | GPR119  | CXCR4   | GPR30    | GLP2R     | PTAFR     | MTNR1B |
| 9  | HTR4   | ADRB2   | CMKLR1  | CXCR5   | GPR183   | GCGR      | LPAR1     | GRM1 |
| 10 | HTR5A  | ADRB3   | GPR1    | CXCR6   | FPR1     | SCTR      | LPAR2     | GRM2 |
| 11 | HTR6   | AGTR1   | CCR1    | ACKR3(CXCR7) | FPR2 | FSHR      | LPAR3     | GRM3 |
| 12 | HTR7   | AGTR2   | CCR2    | XCR1    | FPR3     | LHCGR     | LPAR4     | GRM4 |
| 13 | CHRM1  | APLNR   | CCR3    | CX3CR1  | GPR40    | TSHR      | LPAR5     | GRM5 |
| 14 | CHRM2  | GPBAR1(TGR5) | CCR4 | CCKAR  | GPR41    | GNRHR     | LPAR6     | GRM6 |
| 15 | CHRM3  | BRS3    | CCR5    | CCKBR   | GPR43    | HRH1      | S1PR1     | GRM7 |
| 16 | CHRM4  | GRPR    | CCR6    | C3AR1   | GPR84    | HRH2      | S1PR2     | GRM8 |
| 17 | CHRM5  | NMBR    | CCR7    | C5AR1   | GPR120   | HRH3      | S1PR3     | MLNR |
| 18 | ADORA1 | BDKRB1  | CCR8    | C5AR2   | GABBR1   | HRH4      | S1PR4     | NMUR1 |
| 19 | ADORA2A| BDKRB2  | CCR9    | CRHR1   | GABBR2   | GPR81     | S1PR5     | NMUR2 |
| 20 | ADORA2B| CALCR   | CCR10   | CRHR2   | GALR1    | GPR109A   | MCHR1     | NPFFR1 |

TABLE 1-2

|    | #161-#180 | #181-#200 | #201-#220 | #221-#240 | #241-#260 | #261-#280 | #281-#300 | #301-#314 |
|----|-----------|-----------|-----------|-----------|-----------|-----------|-----------|-----------|
| 1  | NPFFR2    | P2RY6     | TBXA2R    | TAAR1     | GPR12     | GPR61     | GPR153    | MRGPRX3 |
| 2  | NPSR1     | P2RY11    | F2R       | TAAR2     | GPR15     | GPR62     | GPR160    | MRGPRX4 |
| 3  | NPBWR1    | P2RY12    | F2RL1     | TAAR5     | GPR17     | GPR63     | GPR161    | GPR156 |
| 4  | NPBWR2    | P2RY13    | F2RL2     | TAAR6     | GPR19     | GPR75     | GPR162    | GPR158 |
| 5  | NPY1R     | P2RY14    | F2RL3     | TAAR8     | GPR20     | GPR78     | GPR171    | GPR179 |
| 6  | NPY2R     | P2RY8     | QRFPR     | TAAR9     | GPR21     | GPR82     | GPR173    | GPRC5A |
| 7  | NPY4R     | P2RY10    | RXFP1     | UTS2R     | GPR22     | GPR83     | GPR174    | GPRC5B |
| 8  | NPY5R     | PTH1R     | RXFP2     | AVPR1A    | GPR25     | GPR85     | GPR176    | GPRC5C |
| 9  | NTSR1     | PTH2R     | RXFP3     | AVPR1B    | GPR26     | GPR87     | GPR182    | GPRC5D |
| 10 | NTSR2     | PROKR1    | RXFP4     | AVPR2     | GPR27     | GPR88     | LGR4      | GPR107 |
| 11 | OPRD1     | PROKR2    | SSTR1     | OXTR      | GPR31     | GPR101    | LGR5      | GPR137 |
| 12 | OPRK1     | PRLHR     | SSTR2     | ADCYAP1R1 | GPR32     | GPR135    | LGR6      | GPR143 |
| 13 | OPRM1     | PTGDR     | SSTR3     | VIPR1     | GPR34     | GPR139    | MAS1      | GPR157 |
| 14 | OPRL1     | PTGDR2    | SSTR4     | VIPR2     | GPR35     | GPR141    | MASL1     | GPR175 |
| 15 | HCRTR1    | PTGER1    | SSTR5     | GPR4      | GPR37     | GPR142    | MRGPRD    |        |
| 16 | HCRTR2    | PTGER2    | GPR91(SUCNR1) | GPR65(TDAG8) | GPR37L1 | GPR146 | MRGPRE |        |
| 17 | OXGR1(GPR80/99) | PTGER3 | TACR1   | GPR68(OGR1) | GPR39   | GPR148    | MRGPRF    |        |
| 18 | P2RY1     | PTGER4    | TACR2     | GPR132(G2A) | GPR45   | GPR149    | MRGPRG    |        |
| 19 | P2RY2     | PTGFR     | TACR3     | GPR3      | GPR50     | GPR150    | MRGPRX1   |        |
| 20 | P2RY4     | PTGIR     | TRHR      | GPR6      | GPR52     | GPR152    | MRGPRX2   |        |

4. Detection System

In the present invention, provided is a system for detecting activation of a protein by integrating changes in the transcriptional regulatory region of a gene whose expression is changed by activation of the protein (for example, by stimulation with a ligand or an ion) with mediation of a plurality of factors.

In one embodiment, the transcriptional regulatory regions of first to Nth genes whose expression is induced by activation of a certain protein are operably linked to nucleotide sequences encoding first to Nth factors (wherein N is any given integer of 2 or more, and the letter N is used below in this meaning, as necessary). Each of the first to Nth factors may enhance the activity of at least one of the first to Nth factors that are different from the present factor. For example, each factor may increase the expression levels of other factors, or may be a reaction substrate catalyzed by other factors, or may catalyze a reaction of generating the substrate.

Sequences encoding the first to Nth factors may be incorporated into the gene loci of the first to Nth genes on the genome, or nucleic acid molecules, in which the transcriptional regulatory regions of the first to Nth genes are operably linked to the sequences encoding the first to Nth factors, may also be introduced therein.

Furthermore, the assay system of the present invention may comprise a label whose expression is triggered by at least one of the first to Nth factors. As such a label, a molecule whose presence can be easily detected can be used. The label may be a protein, and in such a case, a construct comprising a sequence encoding the label may be used.

Examples of the label may include luciferase, green fluorescent protein (GFP), β-glucuronidase, β-galactosidase, β-lactamase, and alkaline phosphatase. The expression of the label may be triggered by activation of the transcription of the label by the factor, or may also be triggered by the action of another factor to reinforce the signals.

As one example of the construction of the system of the present invention, assuming that there are an N number of genes (genes #1 to gene #N) whose expression is induced after the stimulation of a receptor by a ligand, the following n+1 number of constructs can be constructed:

(1) a first construct, in which the "transcriptional regulatory region of gene #1" is operably linked to the "gene encoding the substrate (S) in the enzyme reaction";

(2) a second construct, in which the "transcriptional regulatory region of gene #2" is operably linked to the "gene encoding the enzyme (E1) in the enzyme reaction";

(3) a third construct, in which the "transcriptional regulatory region of gene #3" is operably linked to the "gene encoding the enzyme (E2) having a product P1 of S and E1 as a substrate";

(4) a fourth construct, in which the "transcriptional regulatory region of gene #4" is operably linked to the "gene encoding the enzyme (E3) having a product P2 of P1 and E2 as a substrate";

↓

(N) an nth construct, in which the "transcriptional regulatory region of gene #N" is operably linked to the "gene encoding the enzyme (E (n−1)) having a product P (n−2) of P (n−3) and E (n−2) as a substrate"; and (N+1) a reporter gene construct designed, so that a reporter gene is activated by a final product P (n−1) obtained after a series of enzyme reactions.

By exogenously, simultaneously introducing the above-described n+1 number of constructs into cells or by forming them in cells by knock-in, there can be constructed a highly sensitive reporter assay system, in which the "stimulation response ratios of transcriptional activity before and after ligand stimulation" of an N number of different transcriptional regulatory regions are synergistically integrated.

A general enzyme reaction formula is represented by:

Enzyme [E]+substrate [S]→enzyme-substrate complex [ES]→enzyme [E]+product [P] ([ ] indicates concentration), and the reaction rate is proportional to the product of [S] and [E]. For this reason, assuming that [S] and [E] are constant during the passage of time, [P] after a certain time has passed after initiation of the reaction is also proportional to the product of [S] and [E]. Therefore, the concentration of the final product P (n−1) produced by the above-described series of enzyme reactions is: [P (n−1)]=[S]×[E1]×[E2]× . . . ×[E (n−1)], and the final stimulation response ratio of the reporter gene is theoretically:

(stimulation response ratio of gene #1)×(stimulation response ratio of gene #2)×(stimulation response ratio of gene #3)×(stimulation response ratio of gene #4)× . . . ×(stimulation of gene #N). That is to say, the final stimulation response ratio can be all of the stimulation response ratios of the N number of genes that are multiplied (synergistic amplification). However, since this assumption is a very simplified model of the principle, [S] and [E] in each reaction are not constant in the actual chain reactions.

Figure 2:
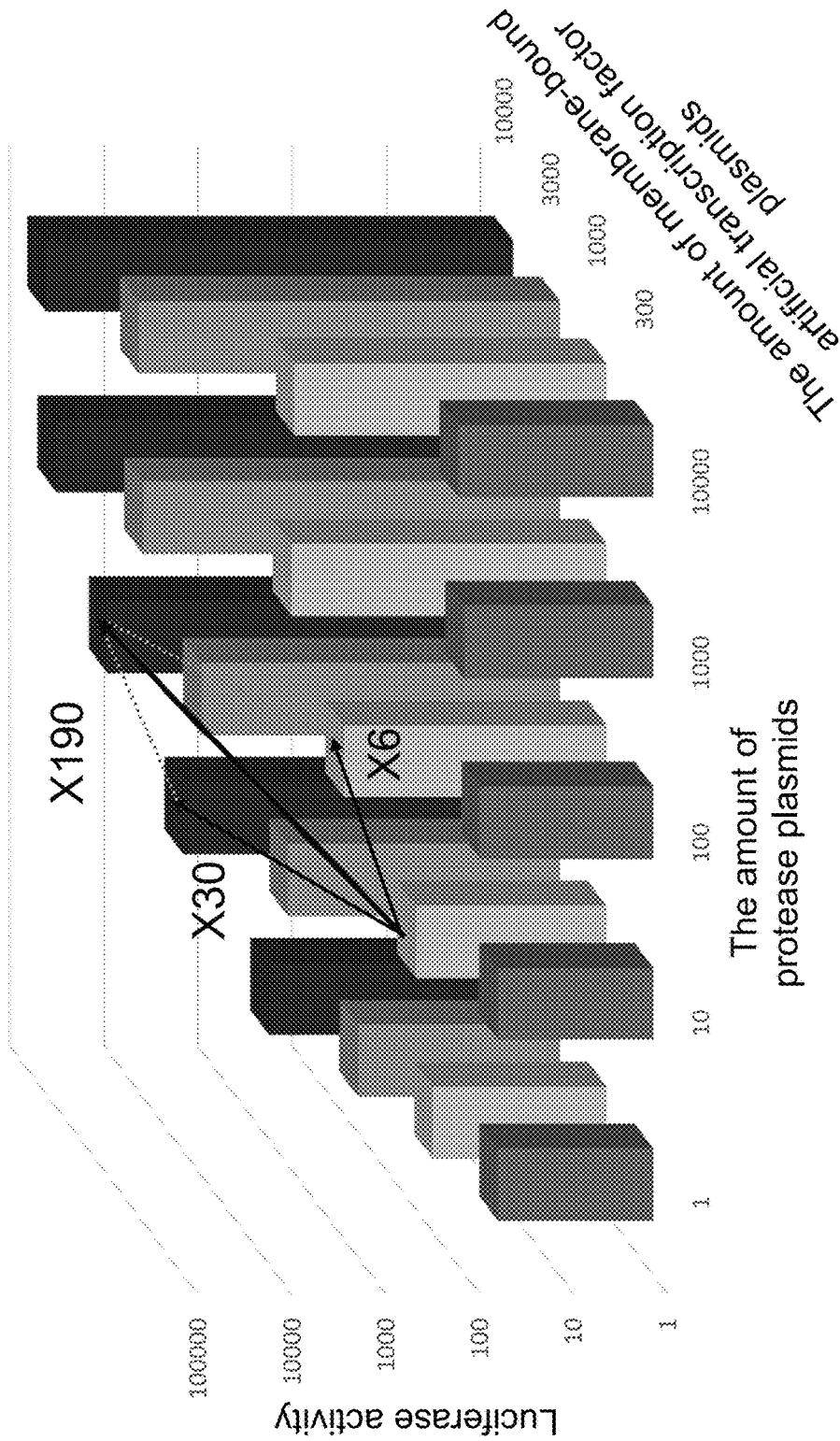
FIG. 2 is a figure showing the results of a proof-of-concept experiment that demonstrate that synergistic signal amplification effects are obtained by using a membrane-bound transcription factor and a protease as factors linked downstream of the transcriptional regulatory region.

Thus, by intervention of enzyme reactions, the transcriptional regulatory regions of a plurality of genes can be functionally linked, and it is thereby expected that a signal amplification effect can be obtained. In order to realize this effect, one example of a combination of factors linked downstream of the transcriptional regulatory region may be a cell membrane-type transcription factor and a protease (FIG. 2). FIG. 2 shows that two types of plasmids, namely, a plasmid expressing a cell membrane-type transcription factor and a plasmid expressing a protease were prepared, and that each plasmid is then exogenously transfected in various amounts (see FIG. 2) into a cell group (a UAS-luciferase reporter gene has also been exogenously introduced into the cells), followed by measuring luciferase activity. The ratio of luciferase activity between the compared two groups is described as a multiple. For example, luciferase activity in a group into which 10 proteases and 1000 cell membrane-type transcription factors had been transfected and luciferase activity in a group into which 100 proteases and 10000 cell membrane-type transcription factors had been transfected were measured and compared with each other. As a result, the group, into which the 100 proteases and the 10000 cell membrane-type transcription factors had been transfected, exhibited luciferase activity that was approximately 190-fold higher than luciferase activity in the group into which the 10 proteases and the 1000 cell membrane-type transcription factors had been transfected. Since the main purpose of the present experiment is to show that luciferase activity is defined by the product of the amount of the cell membrane transcription factor and the amount of the protease, the cell membrane transcription factor and the protease are driven by a constitutive promoter, and they are not linked to the transcriptional regulatory region.

Moreover, in addition to the relationship that one factor activates one factor as described above, a plurality of factors that form a complex and such a complex then activate another factor or a label can also be used. In this case, it is desirable that the reaction speed is relatively slow.

In the present invention, as described above, the transcriptional regulatory region of a gene whose expression is induced by activating a molecule responsible for signal transduction can be used. Depending on the type of the cell, the gene whose expression is induced by the molecule responsible for signal transduction may be different, but those skilled in the art can appropriately identify the gene by the method described in the present description.

As such expression-induced genes, those in which a difference can be detected when the gene expression is induced can be used. Even a gene that cannot be detected with sufficient sensitivity when it is used alone can be used by combining multiple genes with one another. As such expression-induced genes, those having an increase in the expression levels of at least approximately 1.1 time, approximately 1.2 times, approximately 1.5 times, approximately 2 times, approximately 5 times, approximately 10 times, or more, of the basal expression levels, when the expression is induced, can be used. Preferably, a gene whose expression levels are increased by approximately 5 to 10 times or more is used. In the present description, identification of an expression-variable gene by comparison between four groups is described. However, even a gene having a significant difference between two groups can be used as an expression-induced gene.

As the expression levels of a gene, the number of cycles in quantitative PCR (e.g., a Ct value), fluorescence intensity in a microarray, the read count in RNA-Seq (the read count mapped to the gene), etc. can be used. Those skilled in the art can appropriately normalize and use them as indicators. For example, when the expression levels of a gene are measured by RNA-Seq, a value obtained by standardizing the read count by TMM, the median of the ratio, DEGES, FPKM (fragments per kilobase off of exon per million reads mapped), or RPKM (reads per kilobase of exon per million reads mapped) can be used.

Furthermore, the basal expression levels of an expression-variable gene are different depending on the type of the gene, and the expression levels are preferably large. For example, if the FPKM value in RNA-Seq analysis is approximately 1 or more, it is considered that the gene can be used. The gene having an FPKM value in RNA-Seq analysis of approximately 5 to 10 or more is more preferable. In general, an FPKM value of 10 is considered to be high expression, an FPKM value of 5 is considered to be moderate expression, and an FPKM value of 1 is considered to be low expression.

Further, the first to Nth genes whose expression is induced may not be all different from one another. That is, different factors may be operably linked to the transcriptional regulatory region of an identical gene.

When the transcriptional regulatory regions of two or more "different" genes are utilized, certain advantages exist. When two or more factors are introduced into the genome of a cell according to gene knock-in, knocking in two different locations on the genome is technically easier and more reliable than knocking in the same location. For example, since HeLa cells are generally considered to be pseudotriploids, if two factors are to be knocked in the same location on the genome, after the knocking-in of the first factor, the second factor needs to be knocked in either one of the remaining two alleles. When the same gene locus is targeted, whether (1) all of three alleles can be knocked in, or (2) transcription is "on" in all of the three alleles, cannot be determined in advance. Accordingly, it is considered that knocking-in two different locations has a higher probability of success.

When the same region is utilized, stimulus-independent fluctuations are also amplified. By using different regions, noise amplification is avoided, and the improvement of assay precision is expected. The improvement of assay precision can appear as a large difference in precision, when high throughput progresses and the measurement can be performed with a very small number of cells on a microchannel.

In one embodiment, the transcriptional regulatory regions of two or more genes selected from the group consisting of ARC, CCL20, CTGF, DUSP5, EGR1, EGR2, EGR3, FOSB, NR4A1, NR4A3, CYR61 and FOS can be used. In a further embodiment, when the cells are HeLa cells, the transcriptional regulatory regions of CTGF and NR4A1 can be used, and when the cells are HEK293T cells, the transcriptional regulatory regions of FOS and FOSB can be used.

For example, a gene expression response induced when G12/13 was specifically activated in cells (HeLa cells) was analyzed on a genome-wide basis using a next-generation sequencer. As a result, 10 candidate genes (out of approximately 22,000 genes), in which approximately 10 times or more of expression was induced, were found by a genome-wide expression analysis (see Table 2-1 below).

TABLE 2-1

| Gene_ID | FPKM | fold induction |
|---------|------|----------------|
| ARC     | 0.38 | 13.2           |
| CCL20   | 0.13 | 36.6           |
| CTGF    | 11.49| 26.1           |
| DUSP5   | 16   | 14.1           |
| EGR1    | 4.79 | 10.2           |
| EGR2    | 0.12 | 34.8           |
| EGR3    | 0.04 | 65.1           |
| FOSB    | 3.46 | 18.6           |
| NR4A1   | 68.03| 23.1           |
| NR4A3   | 8.92 | 14.7           |

Other than the aforementioned genes, examples of the gene whose expression is induced may include, but are not limited to, ABHD13, ABL2, ACKR3, ACTG1, ADAMTS1, ADAMTS5, ADAP1, ADM, ADRB2, AEBP2, AEN, AHR, AKAP2, ALDH1B1, ALPK2, ANKRD1, ANKRD33B, AP1AR, ARC, AREG, ARHGAP23, ARHGAP28, ARHGAP32, ARHGDIB, ARID5B, ARL5B, ATF3, ATP2B1, ATXN7, BACH1, BCL10, BHLHE40, BIRC3, BMP2, BMPR1B, BTG2, C19orf71, C1QTNF1, C8orf4, C9orf72, CASZ1, CBX4, CCDC68, CCL20, CCNL1, CCNT1, CD83, CDC42EP2, CDC42SE1, CDH5, CDKN1A, CDKN2AIP, CEBPD, CHD1, CHD2, CITED2, CITED4, CMIP, CNN2, COQ10B, CPEB3, CPEB4, CRB1, CREM, CRISPLD2, CSRNP1, CSRP1, CTGF, CTTNBP2NL, CXCL2, CYR61, DAAM1, DAPP1, DAW1, DCUN1D3, DDAH1, DENND3, DKK1, DNAJB4, DNAJC6, DUSP1, DUSP16, DUSP4, DUSP5, DUSP8, EDN1, EDN2, EGLN1, EGR1, EGR2, EGR3, ELAVL2, ELF3, ELL, ELL2, ELMSAN1, EPAS1, EPGN, EPHA2, EPPK1, ERRFI1, ETS2, ETV3, F3, FAM60A, FAM86B3P, FAT4, FBLIM1, FBXO33, FBXO46, FGF2, FHL1, FHL2, FOSB, FOSL1, FOSL2, FOXC1, FOXC2, FRMD4B, FSTL3, GAB2, GADD45A, GADD45B, GATA6, GLI2, GPCPD1, GPRC5A, GRAMD3, HBEGF, HECA, HELZ2, HES4, HK2, HLA-H, HMGCS1, HRH1, HSPA2, ICAM1, IER2, IER3, IER5, IFFO2, IL32, IL6, IQCJ-SCHIP1, IRF2BP2, IRF2BPL, IRS2, ITGB8, ITPRIP, JAG1, JPH2, JUN, JUNB, JUND, KCNJ12, KCNK1, KDM6B, KIAA0355, KIAA0825, KIAA1217, KLF2, KLF4, KLF5, KLF6, KLF7, KLF9, KLHL29, KRT16, KRT17, KRT34, KRT80, LATS2, LDLR, LIFR, LIMA1, LINC00657, LOC100129550, LYPD3, MAFF, MAFK, MALAT1, MAMDC2, MAP2K3, MAP3K14, MAP3K8, MB21D2, MC1R, MCL1, MESDC1, MFAP5, MFSD2A, MITF, MMP12, MMP24, MN1, MPZL3, MTCL1, MXD1, MYADM, MYH9, NAB1, NAB2, NABP1, NAV2, NCEH1, NCOA7, NEDD9, NFIL3, NFKB2, NFKBIA, NFKBID, NFKBIE, NOCT, NR4A1, NR4A2, NR4A3, NT5DC3, NT5E, NTN4, NUAK2, NYAP2, OLR1, OTUD1, PANX1, PDE4D, PDP1, PER1, PER2, PFKFB3, PHLDA1, PHLDA3, PHLDB2, PIGA, PIM1, PLAUR, PLEKHG3, PLEKHO2, PMAIP1, PMP22, PPP1R15B, PPP1R3B, PPP1R3C, PPP2R3A, PPTC7, PRDM1, PRG2, PRRG1, PSD4, PTGER4, PTGS2, PTPRH, PXDC1, RAB20, RAB32, RAP1GAP2, RASAL2, RASD1, RASSF8, RC3H1, RCAN1, REL, RELB, RELT, RGS2, RHOB, RIMKLB, RND3, RNF19A, RNF19B, RNF217, ROR1, RP2, RUNX1, RUSC2, SAMD4A, SAV1, SCML1, SDC4, SERPINE1, SERTAD1, SFMBT2, SGK1, SGMS2, SH3RF1, SIK1, SIRT1, SLC19A2, SLC20A1, SLC25A16, SLC26A2, SLC2A13, SLC2A3, SLC30A7, SLC38A2, SLC7A11, SLFNL1, SLFNL1-AS1, SNRK, SOCS3, SOCS6, SOWAHC, SPRED2, SRF, SSC5D, STARD4, STEAP4, STK38L, STX11, TAGLN, TBX3, TGFBR1, TGFBR3, THBS1, TICAM1, TIPARP, TLE4, TM4SF1, TMEM158, TMEM160, TNFAIP3, TNFRSF10A, TNFRSF8, TNS4, TP53I11, TPM1, TPM4, TPPP, TRAF1, TRAF4, TRIB1, TRMT44, TSC22D1, TSC22D2, TUFT1, UBALD1, UGCG, USP2, USP36, USP53, VCL, VGLL3, VPS37B, WDR1, WDR37, WEE1, WWC2, YOD1, ZBTB10, ZBTB21, ZC3H12A, ZC3H12C, ZC3HAV1, ZFAND5, ZFP36, ZFP36L1, ZFP36L2, ZNF217, ZNF267, ZNF281, ZNF324, ZNF331, ZNF529, ZNF548, ZNF644, ZSWIM4, and ZYX. It has been demonstrated in the present invention that these genes have the activity as described in Example C. One or more of these genes can be used.

Further, the gene expression response induced when G12/13 was specifically activated in cells (HEK293T cells) was analyzed on a genome-wide basis using a next-generation sequencer. As a result, 9 candidate genes, in which approximately 10 times or more of expression was induced, were found by a genome-wide expression analysis (shown in the following Table 2-2).

TABLE 2-2

| gene_id | FPKM | fold induction |
|---|---|---|
| CTGF | 0.53 | 17.3 |
| CYR61 | 3.37 | 19 |
| DUSP5 | 0.89 | 10.5 |
| EGR1 | 2.81 | 51.7 |
| EGR2 | 0.25 | 15.3 |
| EGR3 | 0.19 | 55.9 |
| FOS | 1.31 | 40.7 |
| FOSB | 0.98 | 22.9 |
| NR4A3 | 0.4 | 10.6 |

Furthermore, other examples of the gene whose expression is induced in the present invention may be the following:

NR4A2, LOC100506747, NR4A1, EPPK1, JUN, AMOTL2, FLNA, ARC, IER2, and JUNB (expression fluctuation of 5 times or more in at least any experiment); and CNN2, DUSP1, MAFF, GPR3, TPM1, PTGS2, ATF3, GOS2, TRIB1, SNAI2, PDLIM7, NFKBIZ, TIMP3, FHL2, SPRY2, FOSL2, FERMT2, VCL, NUPR1, TPM4, GRASP, NKX2-5, TUFT1, ID1, FOSL1, MYADM, ACTB, LPP, KLF7, KLF6, ADAMTS1, BTG2, ACTG1, CSRNP1, WDR1, SRF, GEM, ZYX, NR2F1, LOC101928358, ITPRIP, FUT1, COL3A1, LIMA1, SLC8A1, JAG1, SLC6A9, PMAIP1, SLC2A10, PCK2, ZFP36L1, MAFB, CBX4, FZD10, ZBTB10, JDP2, ZNF214, RHOB, ID2, RND3, IRF2BPL, BMP2, SOX4, JUND, SLC1A4, PNRC1, and SYBU (expression fluctuation of 2 times or more in at least any experiment).

Various factors can be used as factors in the present invention, but one preferred example is a transcription factor. The transcription factor can increase the expression of a label or the expression of another factor.

The transcription factor may be, for example, an artificial transcription factor. Examples of the artificial transcription factor may include those shown in the following table. Individual factors bind to the DNA sequences in the right column. A label or another factor can be operably linked to the DNA sequence to which the transcription factor binds.

TABLE 3

| Artificial transcription factor candidate group | DNA sequences to which artificial transcription factors (left) bind |
|---|---|
| Gal4VP16 | UAS |
| Gal4VP64 | UAS |
| tTA | TRE |
| LexA | lexAop |
| lacI | lacO |
| trpR | trpO |
| ZFHG1 | ZFHG1binding site |

In the embodiment of the present invention, the transcription factor may be configured so that it is expressed in an inactivated state. "Inactivation" can be realized, for example, by the transcription factor that does not translocate into the nucleus where transcription takes place, or by the transcription factor that is in an inactive state (e.g., a dephosphorylated state, etc.). By allowing the transcription factor to express in such a state, synergistic enhancement of the signals with the expression of the second factor can be expected.

Preferably, a cell membrane-bound transcription factor can be used as such a transcription factor. The cell membrane-bound transcription factor may be obtained by linking any given molecule localized in the cell membrane to a transcription factor. For example, a molecule that is localized in a cell membrane and a transcription factor may be expressed as a fusion protein containing a peptide linker between them, as necessary. The linker may be a cleavable linker, and for example, the linker may have a sequence that is specifically cleaved by a protease described later. An example of configurations that can be taken by the cell membrane-bound transcription factors other than those described above may be that a transcription factor is anchored from the inside of a cell to the cell membrane via lipid modification such as palmitoylation. Thus, by linking a transcription factor to a molecule localized in the cell membrane, or by including a portion localized in the cell membrane as a part of a transcription factor, the transcription factor can be utilized as a cell membrane-bound transcription factor.

As a factor used in the present invention, a factor having the activity of changing a transcription factor expressed in the above-described inactivated state to an active state can be used. For example, such a factor may have the activity of dissociating the transcription factor from the cell membranes. Depending on the structure of the transcription factor, those skilled in the art can select and use an appropriate factor. For example, when the transcription factor is linked to a membrane-binding moiety via a peptidic cleavable linker, a protease (preferably, a protease specific to the linker sequence) can be used.

A protease can be used as a factor in the present invention. Examples of such a protease may include, but are not limited to, 3C (HRV 3C protease, which is also referred to as Precision protease), TEV protease (Tobacco Etch Virus Protease), caspase 3/7, enterokinase, caspase 8, PSA (prostate-specific antigen) or kallikrein-associated peptidase-3 (KLK3), SARS 3CL1 (3C-like proteinase from SARS coronavirus), factor Xa protease, and thrombin.

In one embodiment of the present invention, the factor having the activity of changing the transcription factor to an active state (for example, a protease) may be a cell membrane-type factor. Such a cell membrane-type factor may be linked to a structure localized in the cell membrane, or may comprise a structure localized in the cell membrane. As the structure of the cell membrane-type factor, the structure localized in the cell membrane in the cell membrane-bound transcription factor described in the present description can also be used. Examples of the possible configuration of the cell membrane-type factor may include a factor (e.g., a protease) that is linked to the intracellular domain of a cell membrane protein, and a factor that is anchored from the inside of a cell to the cell membrane via lipid modification such as palmitoylation. Thus, the factor is linked to a molecule localized in the cell membrane, or a portion localized in the cell membrane is included as a part of the factor, so that the factor can be utilized as a cell membrane-type factor. By utilizing such a cell membrane-type factor, a substrate (a cell membrane-type transcription factor) and an enzyme (a cell membrane-type protease) are localized in an identical intracellular compartment, and the reaction progresses efficiently. It is thereby expected to obtain the effect of detecting a signal with high sensitivity even under conditions where the amounts of the substrate and the enzyme are limited.

Figure 5:
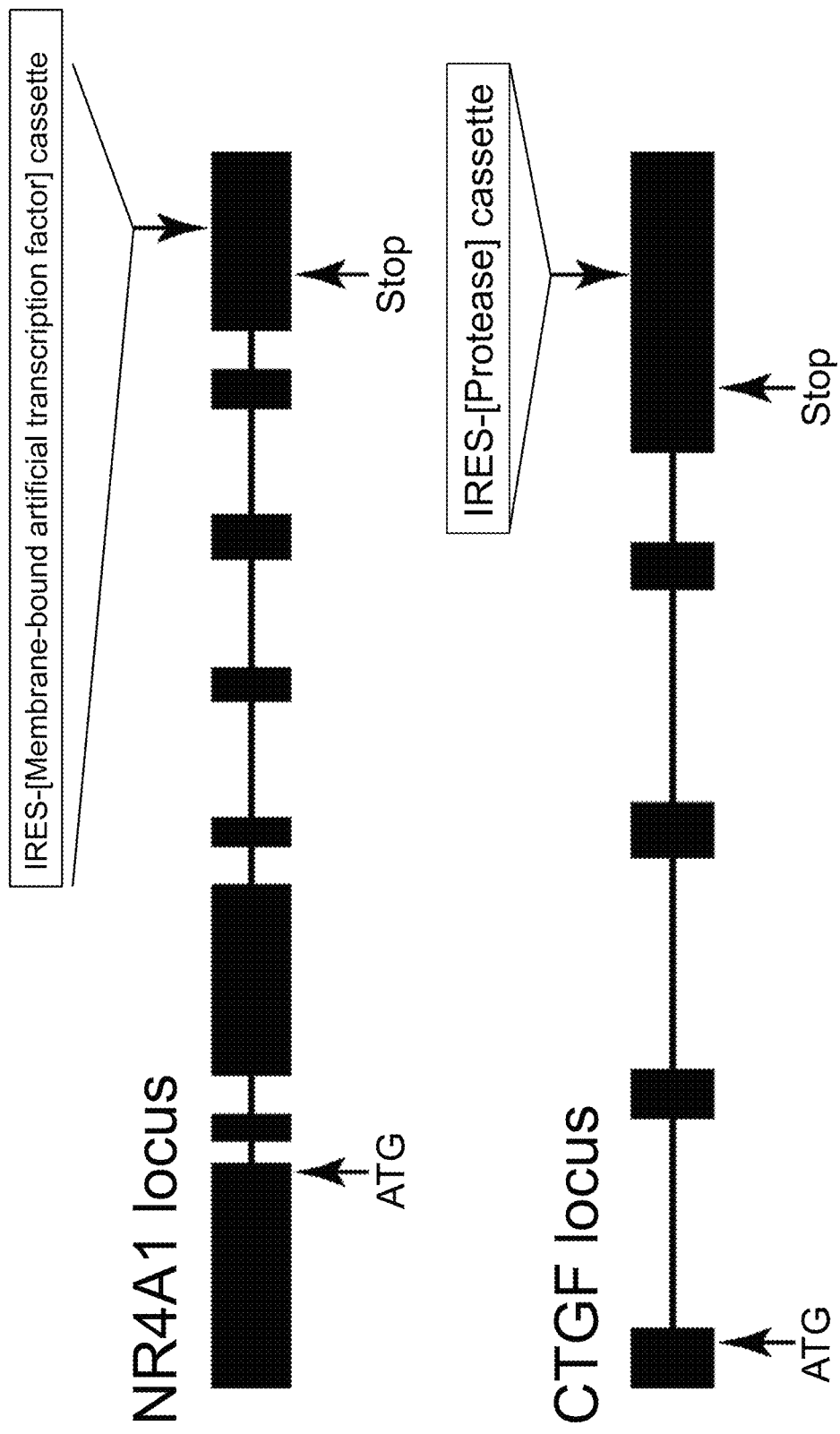
FIG. 5 is an example of the configuration of the construct of the present invention. Two different loci (NR4A1 locus and CTGF locus) are selected from a list of genes whose expressions are induced when GPCR is stimulated by a ligand (in HeLa cells), and two reporter assay system component factors (a membrane-bound artificial transcription factor and a protease) can be knocked-in into the 3'-UTR of each locus.
Figure 6:
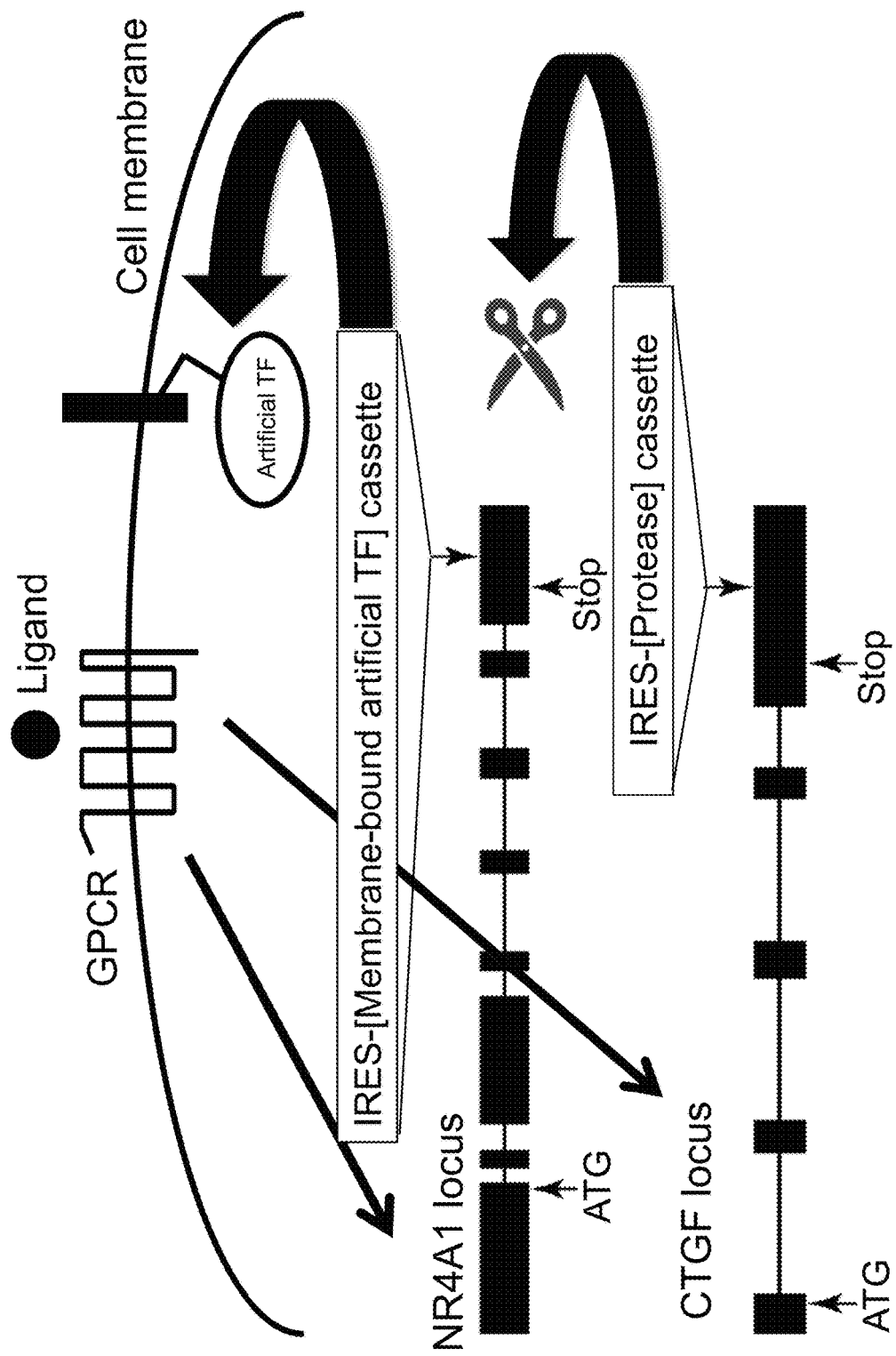
FIG. 6 shows the mechanism of measuring ligand activity in genome-modified cells, in which a membrane-bound artificial transcription factor and a protease are each knocked-in into the 3'-UTR of an NR4A1 gene and a CTGF gene whose expressions are induced by ligand stimulation.

In one example, two different gene loci (NR4A1 locus and CTGF locus) can be selected from the aforementioned gene list (HeLa cells) whose expression is induced. In addition, a cell membrane-bound artificial transcription factor and a protease can be introduced into in the 3' UTR of those gene loci according to gene knock-in (FIG. 5). By forming the construct as shown in FIG. 5, there are obtained HeLa cells whose genome has been modified so that the expression of the cell membrane-bound artificial transcription factor and the protease are induced by GPCR stimulation (FIG. 6).

In another embodiment of the present invention, when the cells are HEK293T, by introducing a cell membrane-bound artificial transcription factor and a protease into the 3' UTR of the selected two different gene loci (FOS locus and FOSB locus) according to gene knock-in, indicator cells having the same function as the HeLa cells can be produced.

Using such cells, the ligand activity of a test compound can be measured as follows.
1. Luciferase and a GPCR gene of interest are introduced into reporter cells.
2. The genome of cells used in the assay has been modified in advance, so that the expression of a cell membrane-bound artificial transcription factor and a protease can be induced by GPCR stimulation.
3. The transcription factor and the protease stimulated by GPCR synergistically induce luciferase expression.

5. Construct/Kit

In one embodiment, a construct or a combination of constructs for investigating the action of a test compound on a protein responsible for signal transduction is provided. The construct or the combination of constructs may comprise first to Nth nucleotide sequences encoding first to Nth factors, respectively, which are operably linked to the transcriptional regulatory regions of first to Nth genes whose expression is induced by activation of the protein responsible for signal transduction. Herein, N is an integer of 2 or more. There can also be provided a combination of constructs, comprising the aforementioned construct or the aforementioned combination of constructs, and a construct comprising a nucleotide sequence encoding a label that is configured so that its expression is triggered by at least one of the first to Nth factors.

In addition, these constructs may also be provided in the form of a kit. In one embodiment, a kit for investigating the action of a test compound on a protein responsible for signal transduction is provided, and the kit may include the above-described construct or the above-described combination of constructs.

In a further embodiment, there may be provided a kit for investigating the action of a test compound on a protein responsible for signal transduction, wherein the kit includes a plurality of tandemly related factors. For example, the kit may be a kit including:
(1) a first construct in which the transcriptional regulatory region of a first gene is linked to a nucleotide sequence encoding a substrate (S) for an enzyme reaction;
(2) a second construct in which the transcriptional regulatory region of a second gene is linked to a nucleotide sequence encoding an enzyme (E1) for an enzyme reaction, wherein a product P1 is generated as a result of the enzyme reaction between S and E1;
with regard to each n that is a natural number of 3 to N, provided that N is 3 or more,
(n) an nth construct in which the transcriptional regulatory region of an nth gene is linked to a gene encoding an enzyme (E (n−1)) that produces a product (P (n−1)) using P (n−2) as a substrate; and
(N+1) a reporter gene construct that is configured so that a reporter gene is activated by a product P (N−1) of an enzyme reaction, wherein
the expression of each of an N number of first to Nth genes is induced by stimulation of the protein by the test compound, wherein N is a natural number of 2 or more and n is a natural number of 1 to N. The kit may further include a construct encoding the chimeric G protein α subunit described in the present description. The kit may further include a drug for introducing the construct or the combination of constructs into a cell, or for forming the construct or the combination of constructs in a cell. By specifying the first to Nth genes whose expression is induced by the activation of the above-described protein, the above-described construct, the above-described combination of constructs, or the above-described kit can be produced.

6. Cells

In the present invention, there are provided cells into which the assay system described in the present description is incorporated. As such cells, one or more cells selected from the group consisting of, for example, HeLa cells, HEK293 cells, CHO cells, COS-1/7 cells, HL60 cells, K562 cells, Jurkat cells, HepG2 cells, Saos-2 cells, F9 cells, C2C12 cells, PC12 cells, NIH/3T3 cells, U2OS cells, Vero cells, MDCK cells, MEF cells, U937 cells, C6 cells, Neuro2A cells, SK-N-MC cells, SK-N-SH cells, HUVEC cells, THP-1 cells, BW5147 cells, Ba/F3 cells, Y-1 cells, H295R cells, MIN6 cells, NIT-1 cells, and MDA-MB435S cells, can be used.

The cell of the present invention may comprise the chimeric G protein described in the present description or a nucleic acid encoding the same, as well as the assay system described in the present description. In addition, the cell of the present invention may be a cell, in which a molecule responsible for desired signal transduction (or a molecule that activates a molecule responsible for signal transduction, for example, a receptor) is overexpressed.

The cell of the present invention can be produced by introducing into a cell, a plurality of nucleic acid molecules constituting the assay system described in the present description. That is, the cell of the present invention can be produced by introducing one or more nucleic acid molecules comprising nucleic acid sequences encoding first to Nth factors, which are operably linked to the transcriptional regulatory regions of first to Nth genes whose expression is induced by activation of a molecule responsible for signal transduction, into the concerned cell line.

Introduction of nucleic acids into cells can be performed by lipofection, gene gun, a calcium chloride method, calcium phosphate precipitation, conjugation, protoplast fusion, electroporation, an *Agrobacterium* method, virus infection, direct microinjection, and the like.

Alternatively, the first to Nth factors are incorporated into the gene loci of endogenous first to Nth genes to form a construct in a cell, so that the cell of the present invention can be produced. For incorporation of the first to Nth factors into the endogenous gene loci, a technique known in the present technical field can be used, and for example, a genome editing technique can be used.

As such a genome editing technique, for example, a CRISPR-Cas9 system, zinc finger nuclease, TALEN, PPR nuclease, homologous recombination, a modification method thereof, and the like can be used. The genome editing can be carried out, as appropriate, by those skilled in the art, with reference to information disclosed in Curr Protoc Mol Biol (2012) Chapter 12: Unit 12.15, Nat Biotechnol (2012) 30: 460-465, Nucleic Acids Res (2011) 39: e82, JP Patent Publication (Kohyo) No. 2013-513389 A, Nat Biotechnol (2002) 20: 135-141, Mol Cell (2008) 31: 294-301, Nat Methods (2011) 8: 67-69, Nat Biotechnol (2008) 26: 695-701, Japanese Patent No. 4968498, JP Patent Publication (Kokai) No. 2013-128413 A, etc.

In the present invention, provided is a cell expressing a protein responsible for signal transduction, comprising: first to Nth nucleotide sequences encoding first to Nth factors, respectively, which are operably linked to the transcriptional regulatory regions of first to Nth genes whose expression is induced by activation of the above-described protein, and a nucleotide sequence encoding a label that is configured so that its expression is triggered by at least one of the first to Nth factors, wherein N is an integer of 2 or more.

The cell may express a protein responsible for signal transduction and may comprise a plurality of linearly related factors. For example, the cell comprises:

(1) a first construct in which the transcriptional regulatory region of a first gene is linked to a nucleotide sequence encoding a substrate (S) for an enzyme reaction;

(2) a second construct in which the transcriptional regulatory region of a second gene is linked to a nucleotide sequence encoding an enzyme (E1) for an enzyme reaction, wherein a product P1 is generated as a result of the enzyme reaction between S and E1;

with regard to each n that is a natural number of 3 to N, provided that N is 3 or more, (n) an nth construct in which the transcriptional regulatory region of an nth gene is linked to a gene encoding an enzyme (E (n−1)) that produces a product (P (n−1)) using P (n−2) as a substrate; and (N+1) a reporter gene construct that is configured so that a reporter gene is activated by a product P (N−1) of an enzyme reaction, wherein the expression of each of an N number of first to Nth genes is induced by activation of the protein, wherein N is a natural number of 2 or more and n is a natural number of 1 to N.

In one embodiment, provided is a kit including a plurality of cells, each expressing a different membrane protein, wherein each of the plurality of cells has characteristics described in the present description. The kit may be for comprehensively analyzing the action of a test compound on a membrane protein. In one embodiment, provided is a method for analyzing the action of a test compound on a membrane protein, characterized in that it uses the cell described herein or the kit described herein.

As a method for producing a cell described in the present description, provided is a production method comprising a step of transfecting a cell with a membrane protein or a GPCR, and a step of introducing the first to Nth nucleotides into the gene loci of first to Nth genes whose expression is induced, so that they are operably linked to the transcriptional regulatory regions of individual genes.

The cell of the present invention is a cell that expresses a membrane protein, wherein the cell comprising:

a first nucleotide sequence operably linked to the transcriptional regulatory region of a first gene whose expression is induced by activation of the membrane protein, the nucleotide sequence encoding a cell membrane-bound transcription factor, a second nucleotide sequence operably linked to the transcriptional regulatory region of a second gene whose expression is induced by activation of the membrane protein, the nucleotide sequence encoding a protease, and a nucleotide sequence encoding luciferase that is configured so that its expression is triggered by the transcription factor, wherein the membrane protein is a G protein-coupled receptor (GPCR), an enzyme-linked receptor, an ion channel-linked receptor, or a channel, and the cell membrane-bound transcription factor comprises a cleavable linker cleaved with the protease between a cell membrane-bound portion and a transcription factor portion.

Examples of the present cell may include a HeLa cell and a HEK293T cell. When the cell is a HeLa cell, for example, the first gene is NR4A1 and the second gene is CTGF. When the cell is a HEK293T cell, for example, the first gene is FOS and the second gene is FOSB.

7. Chimera

In another aspect, the present invention also provides a chimeric G protein, a nucleic acid encoding the same, a cell expressing the same, and a method of using the same. In the present description, provided are a G protein α subunit that becomes a chimera and a chimeric G protein comprising the same. Since the coupling of the G protein with the receptor is determined by the amino acid sequence at the C-terminus of the Gα subunit, by using a chimeric G protein, activation of a GPCR coupled with a certain G protein can be detected using an intracellular signal generated when a different G protein is activated. The present invention provides a chimeric G protein α subunit, in which the C-terminal amino acid sequence of a certain G12/13 α subunit is replaced with the amino acid sequence of a different G protein α subunit.

Examples of the different Gα subunit may include Gαs, Gαi, and Gαq, and the Gαs unit is preferable. The range to be replaced as a chimera may be approximately 50 amino acids or less, approximately 40 amino acids or less, approximately 30 amino acids or less, approximately 20 amino acids or less, or approximately 10 amino acids or less, on the C-terminal side of the G12/13 α subunit. The range to be replaced as a chimera is preferably 6 amino acids.

The chimeric G protein provided by the present invention can be used in the method for investigating the action of a test compound on a protein responsible for signal transduction described in the present description. The construct described herein can be used in combination with a chimeric G protein (or a construct encoding the same). For example, a chimeric G protein can be further expressed in a cell comprising the above-described construct, and a signal from a GPCR coupled with a G protein other than G12/13 (e.g., Gs) can be detected in the same detection system as that for a signal from G12/13.

In one embodiment, the chimeric G protein may comprise an α subunit having the sequence of SEQ ID NO: 6, the sequence of SEQ ID NO: 8, or a sequence having a sequence identity of at least approximately 90% thereto, or a fragment thereof.

One embodiment relates to a chimeric G protein α subunit having an amino acid sequence, in which the amino acid sequence of the C-terminus in the amino acid sequence of a first Gα subunit belonging to Gα12/13 is replaced with the amino acid sequence of a Gα subunit different from the first Gα subunit. As such a different Gα, Gαs can be used. Approximately 6 amino acids at the C-terminus thereof can be replaced with the amino acid sequence of a different Gα subunit. A chimeric G protein comprising such a chimeric G protein α subunit is also provided. A conjugate comprising a chimeric G protein and a GPCR coupled to the chimeric G protein, or a cell comprising the same is provided. The cell may further comprise the construct described in the present description. These cells can be used in the functional analysis of a GPCR. The chimeric G protein can also be provided as a construct comprising a nucleotide sequence encoding the same.

8. Gene Identification

In another aspect, the present invention provides a method for identifying a gene whose expression is induced by activation of a protein responsible for signal transduction in a certain cell. The activatable gene found by this method can be utilized in the comprehensive assay of a protein of the present invention, and can be used as a part of the construct of the present invention.

This method of the present invention can be used to investigate the interaction between a protein responsible for signal transduction and a test compound. The method may comprise: a step of obtaining the expression levels of a gene in a cell expressing a protein, when the cell is allowed to come into contact with an activator of the protein; a step of obtaining the expression levels of a gene in the cell, when the cell is not allowed to come into contact with the activator; and a step of selecting, as a candidate gene, a gene whose expression increases in the case of contacting with the activator compared with in the case of not contacting with the activator.

Regarding the identification of a gene whose expression is induced, a comparison can be made among four groups, based on the presence or absence of the protein and the presence or absence of the activator. A gene whose expression increases when the cell expressing the protein is allowed to come into contact with the activator can be selected as candidate genes.

In one embodiment, in order to investigate the action of a test compound on a molecule responsible for signal transduction, provided is a method for identifying a gene whose expression is induced by activation of the above-described molecule in a cell. The method may comprise: a step of obtaining the expression levels of a gene, when a cell expressing the above-described molecule is allowed to come into contact with an activator of the above-described molecule; and a step of obtaining the expression levels of the gene, when the cell is not allowed to come into contact with the activator. Moreover, the method may comprise a step of selecting, as a candidate gene, a gene whose expression increases in a case where the cell is allowed to come into contact with the activator, compared with in a case where the cell is not allowed to come into contact with the activator.

In one embodiment, provided is a method for identifying a gene whose expression is induced by activation of a molecule responsible for signal transduction in a certain cell, wherein the method is characterized by a comparison among four groups. The method may comprise:

a step of obtaining the expression levels of a gene, when a cell expressing the above-described molecule is allowed to come into contact with an activator of the above-described molecule;

a step of obtaining the expression levels of the gene, when the cell expressing the above-described molecule is not allowed to come into contact with the activator;

a step of obtaining the expression levels of the gene, when the cell not expressing the above-described molecule is allowed to come into contact with the activator; and a step of obtaining the expression levels of the gene, when the cell not expressing the above-described molecule is not allowed to come into contact with the activator. In addition, the method may comprise a step of selecting, as a candidate gene, a gene whose expression increases in the case where the cell expressing the above-described molecule is allowed to come into contact with an activator of the above-described molecule, compared with other cases.

A GPCR that is specifically coupled with the G protein G12/13 can be used as a molecule responsible for signal transduction. This method may be for the production of a cell used for an assay. In the above-described cell, a nucleotide sequence is incorporated into a gene locus such that it is operably linked to the transcriptional regulatory region of the candidate gene, thereby producing the cell used for an assay.

The expression of a gene can be measured by any given method known in the present technical field. Examples of the technique of measuring the expression levels of a gene may include microarray, RNA-Seq, and quantitative PCR. Preferably, RNA-Seq can be adopted. The sequencing method is not limited, as long as the sequence of a nucleic acid sample can be determined thereby, and any given method known in the present technical field can be utilized. It is preferable to use next-generation sequencing (NGS). Examples of the next-generation sequencing may include, but are not limited to, pyrosequencing, sequencing by synthesis, sequencing by ligation, and ion semiconductor sequencing.

The method for identifying a gene of the present invention can be carried out, as appropriate, by referring to, for example, "Next-Generation Sequencer: Advanced Method for Each Purpose" (Cell Engineering Separate Volume) and references such as Cold Spring Harb Protoc. 2015 November; 2015 (11): 951-969.

9. Application

The present invention can be utilized to comprehensively investigate the action of a test compound on a membrane protein. Such comprehensive investigation is useful not only for investigating the action of a test compound on a intended specific target, but also for detecting the action of a test compound on a molecule different from the intended specific target, namely, off-target activity. By investigating the action of a test compound on a specific target, the usefulness of the test compound for pharmaceutical drugs, etc. can be examined. In addition, by detecting off-target activity, the safety test or toxicity test of the compound can be carried out. Accordingly, the present invention is useful for supporting drug discovery. As one usage method, the binding of a test compound that activates a target receptor to one or more receptors including the target receptor can be screened. As receptors whose binding can be screened, those disclosed in the present description can be used as target receptors. For example, GPCRs (e.g., G12/13-coupled GPCRs that have been hardly detected so far) can be used as targets. The GPCRs include receptors relating to tastes (e.g., a bitter taste receptor). As an example, by investigating the action of a test compound on such a bitter taste receptor, the taste characteristics of the test compound can be examined. Moreover, according to comprehensive screening, what is called, an orphan receptor whose ligand is unknown can be used as a target. In addition, as described in the Examples of the present description, it is also possible to detect activation of receptor-type tyrosine kinase.

EXAMPLES

Example A1: Reporter System Using Transcriptional Regulatory Region Sequences of a Plurality of Genes Whose Expressions are Induced

[Overview]

The present example is intended to demonstrate that signals are amplified by exogenously and transiently introducing a plurality of reporter assay component genes having different transcriptional regulatory regions into animal cells. More specifically, it is shown in the present example that signals are amplified by exogenously and transiently introducing a plurality of reporter assay component genes having different transcriptional regulatory regions (in the present experiment, an NFAT (nuclear factor of activated T-cells) transcriptional regulatory region and an SRF (serum response factor) transcriptional regulatory region) into animal cells.

[Materials and Methods]

It had already been known that an angiotensin type 1 receptor (hAgtr1) belonging to a GPCR group is activated by its ligand angiotensin II, and increases the expression of a gene having an NFAT (nuclear factor of activated T-cells) transcriptional regulatory region or an SRF (serum response factor) transcriptional regulatory region, independently from the cell species used in the assay (i.e., almost common in all cell species). In view of the foregoing, as factors connecting these two transcriptional regulatory regions with each other, the following two artificial genes (TMGV and TM3C) were produced.

(1) Production of Cell Membrane-Bound Artificial Transcription Factor (TMGV: Transmembrane Gal4VP64)

The amino acid sequence GSSSLEVLFQGPGSSS (SEQ ID NO: 2) including the HRV protease 3C recognition cleavage sequence (LEVLFQGP (SEQ ID NO: 1)) was connected in-frame with the C-terminus of a human IL2 receptor alpha chain (NM_000417) from which a stop codon was deleted, and thereafter, Gal4VP64 (GV: an artificial transcription factor), from which a start codon was deleted, was further connected in-frame with the C-terminus.

(2) Production of Membrane-Bound HRV 3C Protease (TM3C: Transmembrane 3C)

The GS-linker sequence (GGGGSGGGGSGGGGS) (SEQ ID NO: 3) and HRV protease 3C (the amino acid sequence of which was humanized), from which both a start codon and a stop codon were deleted, were connected in-frame in this order with the C-terminus of a human IL2 receptor alpha chain (NM_000417) from which a stop codon was deleted, and thereafter, for the purpose of destabilizing the membrane protein, a PEST sequence was further added to the C-terminus thereof.

When the above-described (1) TMGV and (2) TM3C were simultaneously transfected into cells, both of the two components were translocated to the cell membrane according to an IL2 receptor transport system. When the two components meet on the cell membrane, (1) TMGV functions as a substrate (S), and (2) TM3C functions as an enzyme (E), so that the artificial transcription factor GV is released from the cell membrane to the cytoplasm. GV (soluble GV: sGV) released from the membrane can be considered to be a product (P) generated as a result of the enzyme reaction. That is to say, the amount of the product (sGV) is determined by the product of the concentrations of (1) TMGV and (2) TM3C on the cell membrane. The amount of the produced sGV can be quantified by utilizing a reporter gene UAS-luciferase prepared by connecting luciferase with a UAS sequence (wherein UAS is an sGV binding sequence, and the expression of luciferase is induced by the binding of sGV).

Figure 3:
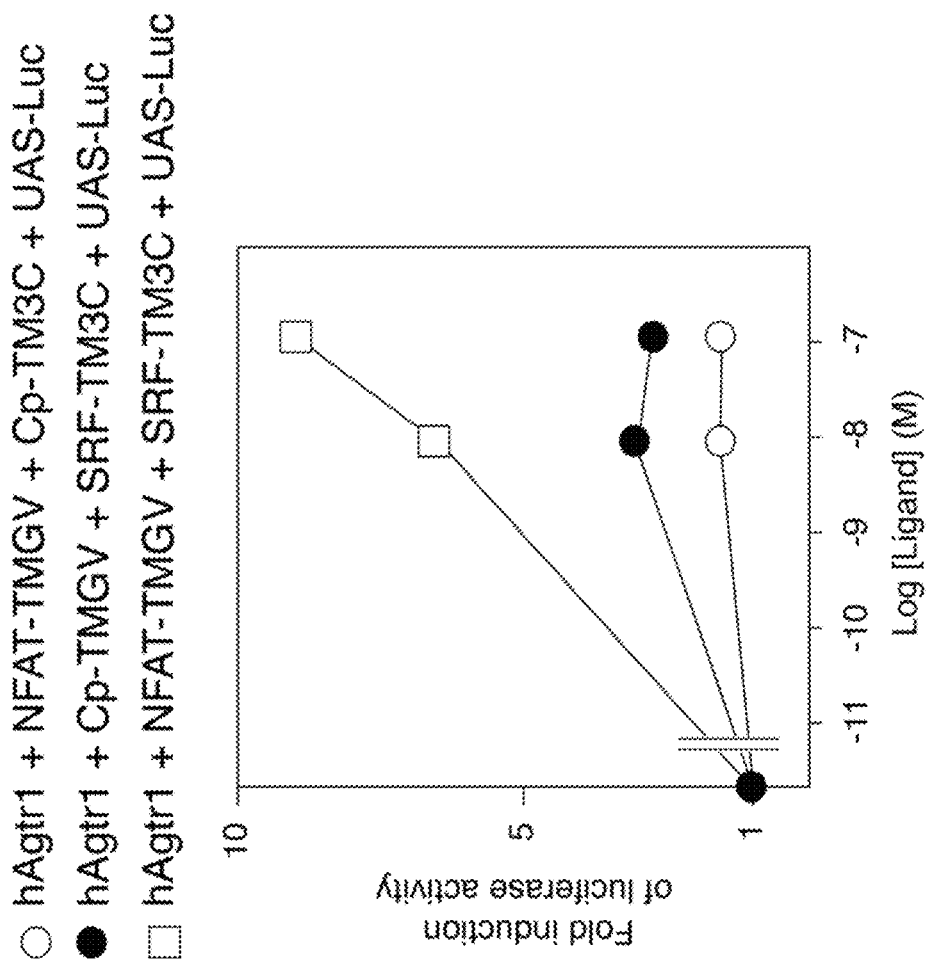
FIG. 3 shows signals detected by exogenously and transiently introducing a plurality of reporter assay component genes (NFAT-TMGV and SRF-TM3C) having different transcriptional regulatory regions into animal cells. The horizontal axis indicates a ligand concentration, and the vertical axis indicates the luminescence intensity output in each assay system. TMGV: membrane-bound artificial transcription factor; TM3C: protease.

Therefore, in the present example, plasmid cocktails including the following three different combinations were prepared:

(1) hAgtr1+NFAT-TMGV+constitutive promotor (Cp)-TM3C+UAS-luciferase (wherein only the expression of TMGV is induced by ligand stimulation);

(2) hAgtr1+Cp-TMGV+SRF-TM3C+UAS-luciferase (wherein only the expression of TM3C is induced by ligand stimulation); and (3) hAgtr1+NFAT-TMGV+SRF-TM3C+UAS-luciferase (wherein the expression of both TMGV and TM3C is induced by ligand stimulation).
Used cells: HeLa cells
Day 1: HeLa cells were seeded on a 96-well plate at a density of 24000 cells/well.
Day 2: Within 24 hours after the seeding on the 96-well plate, 84.6 ng of DNA per well (a plasmid cocktail consisting of 60 ng of hAgtr1, 12 ng of TMGV, 0.6 ng of TM3C, and 12 ng of UAS-luciferase) was transfected into the cells according to a lipofection method.
Day 3: Twenty-four hours after the transfection, the cells were stimulated by a ligand (angiotensin II, at concentrations of 100 nM, 10 nM, and 0 nM). After the stimulation for 6 hours, a culture supernatant was discarded, and a substrate for luciferase was added, and then, luminescence signals were measured using a plate reader.
[Results]
The results are shown in FIG. 3. More favorable ligand concentration-dependent signals were detected in the above combination (3), compared with the above combinations (1) and (2). It was demonstrated that signals were amplified by exogenously and transiently introducing a plurality of reporter assay component genes having different transcriptional regulatory regions into animal cells.

Example A2: Use of a Plurality of Reporter Assay Component Genes Having Identical Transcriptional Regulatory Regions

Figure 4:
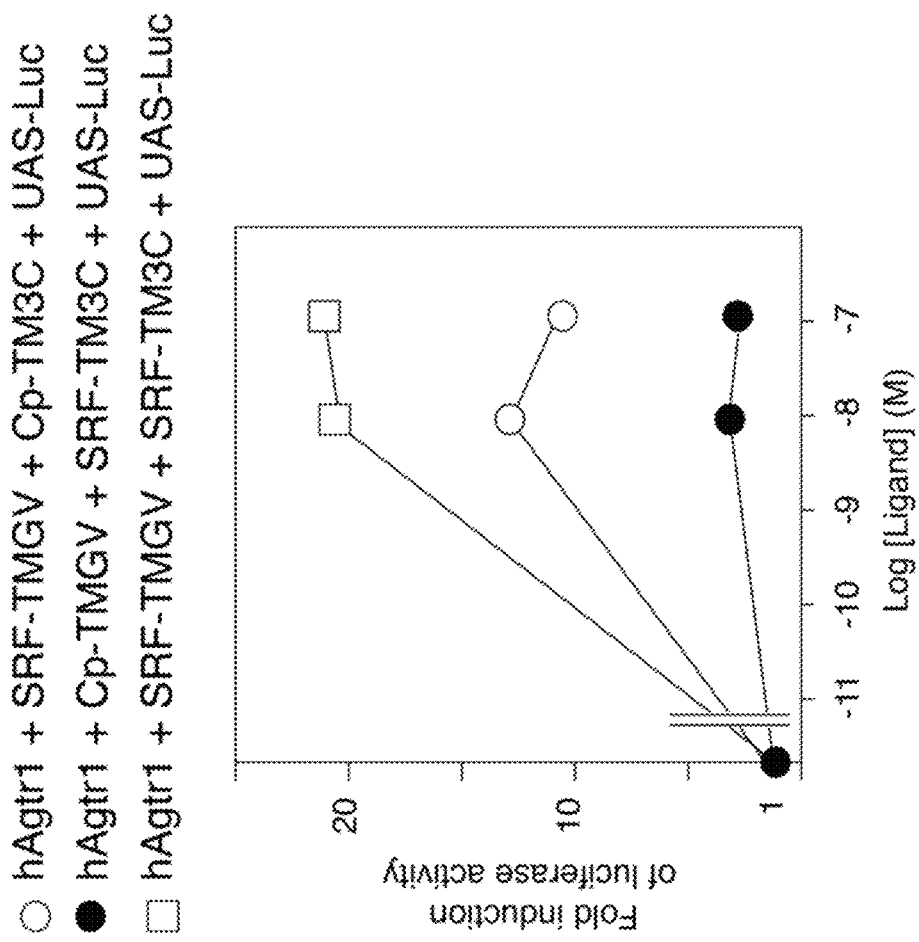
FIG. 4 shows signals detected by exogenously and transiently introducing a plurality of reporter assay component genes (SRF-TMGV and SRF-TM3C) having identical transcriptional regulatory regions into animal cells. The horizontal axis indicates a ligand concentration, and the vertical axis indicates the luminescence intensity output in each assay system. TMGV: membrane-bound artificial transcription factor; TM3C: protease.

[Overview]
The present example is intended to demonstrate that signals are amplified by exogenously and transiently introducing a plurality of reporter assay component genes having identical transcriptional regulatory regions (which are, in the present experiment, SRF (serum response factor) transcriptional regulatory regions) into animal cells.
[Materials and Methods]
It had already been known that an angiotensin type 1 receptor (hAgtr1) belonging to a GPCR group is activated by its ligand angiotensin II, and increases the expression of a gene having an SRF (serum response factor) transcriptional regulatory region, independently from the cell species used in the assay (i.e., almost common in all cell species).
Hence, plasmid cocktails including the following three different combinations were prepared:
(1) hAgtr1+SRF-TMGV+constitutive promotor (Cp)-TM3C+UAS-luciferase (wherein only the expression of TMGV is induced by ligand stimulation);
(2) hAgtr1+Cp-TMGV+SRF-TM3C+UAS-luciferase (wherein only the expression of TM3C is induced by ligand stimulation); and
(3) hAgtr1+SRF-TMGV+SRF-TM3C+UAS-luciferase (wherein the expression of both TMGV and TM3C is induced by ligand stimulation).
Used cells: HeLa cells
Day 1: HeLa cells were seeded on a 96-well plate at a density of 24000 cells/well.
Day 2: Within 24 hours after the seeding on the 96-well plate, 84.6 ng of DNA per well (a plasmid cocktail consisting of 60 ng of hAgtr1, 12 ng of TMGV, 0.6 ng of TM3C, and 12 ng of UAS-luciferase) was transfected into the cells according to a lipofection method.
Day 3: Twenty-four hours after the transfection, the cells were stimulated by a ligand (angiotensin II, at concentrations of 100 nM, 10 nM, and 0 nM). After the stimulation for 6 hours, a culture supernatant was discarded, and a substrate for luciferase was added, and then, luminescence signals were measured using a plate reader.
[Results]
The results are shown in FIG. 4. More favorable ligand concentration-dependent signals were detected in the above combination (3), compared with the above combinations (1) and (2). It was demonstrated that signals were amplified by exogenously and transiently introducing a plurality of reporter assay component genes having identical transcriptional regulatory regions into animal cells.

Example A3: Establishment of Indicator Cells Used in Novel GPCR Assay System Capable of Detecting G12/13-Coupled GPCR with High Sensitivity

[Overview]
Since a transcriptional regulatory region responding to a G12/13 protein with a high response ratio before and after activation of the G12/13 protein has not yet been elucidated at the present time, it is difficult to evaluate a GPCR coupled with G12/13 using an ordinary reporter assay system. Thus, whether or not such a G12/13-coupled GPCR can be evaluated by utilizing the findings obtained in the aforementioned examples was verified.
[Materials and Methods]
A GPCR stimulated by a ligand transmits signals into cells through a heterotrimeric GTP-binding protein (G protein composed of three subunits, α, β and γ). The G protein is roughly classified into Gs, Gi, Gq, and G12/13, based on the sequence of α subunit. GPCRs are classified into four groups, namely, "Gs-coupled GPCRs," "Gq-coupled GPCRs," "Gi-coupled GPCRs" and "G12/13-coupled GPCRs."
The "transcriptional regulatory region responding to a G12/13 protein with a high response ratio before and after activation of the G12/13 protein," regardless of the animal cell species used in the assay, has not been elucidated at the present time, it is difficult to evaluate a "G12/13-coupled GPCR" using an ordinary reporter assay system.
First, HeLa cells, in which a "GPCR specifically coupled with a G12/13 protein" was overexpressed, were prepared. Subsequently, the cells were stimulated with a ligand corresponding to the overexpressed GPCR (specific activation of the G12/13 protein), and a group of genes whose expressions are induced before and after ligand stimulation was listed up (refer to the after-mentioned Example C for identification of candidate genes). Consistent with the fact that the "transcriptional regulatory region responding to a G12/13 protein with a high response ratio before and after activation of the G12/13 protein" has not been known, genes whose expressions are induced with a high stimulation response ratio (30 times or more) could not be identified, and only several genes whose expressions are induced with a middle stimulation response ratio (5 to 10 times or more) could be identified.
Hence, two genes having a middle stimulation response ratio of about 10 times (gene #1 and gene #2) were focused on (gene #1: NR4A1, gene #2: CTGF).
Transcription of a gene is often cooperatively controlled by a plurality of transcriptional regulatory regions located in different sites on the chromosome. In a case where a gene whose expression is induced with an extremely high stimulation response ratio before and after ligand stimulation can be focused on, one of the plurality of transcriptional regulatory regions possessed by the gene is cloned, and an artificial reporter gene plasmid is then produced based on the clone, so that it is likely that a reporter assay system having a sufficient stimulation response ratio can be constructed. However, as in the present case, in a case where a gene originally having only a middle level of stimulation response ratio is focused on, even if one of the plurality of transcriptional regulatory regions possessed by the gene is cloned and an artificial reporter gene plasmid is then produced, it is likely that a reporter assay system having a sufficient stimulation response ratio cannot be constructed.

Hence, in the present case, instead of adopting common means, a reserve thinking is adopted such that reporter assay system components (i.e., TMGV and TM3C) are directly knocked-in into the 3'-UTR of gene #1 and gene #2, and such that the reporter system itself is incorporated in the chromosome of cells (i.e., is allowed to be endogenously present in cells). Thus, by utilizing all of the transcriptional regulatory regions of gene #1 and gene #2 endogenously existing in HeLa cells, indicator cells regulating the transcription of TMGV and TM3C were established (FIG. 5 and FIG. 6).

Upon the establishment of the above-described indicator cells, first, gene fragments, namely, (1) IRES-TMGV and (2) IRES-TM3C were produced by adding an IRES (internal ribosome entry site) sequence to the N-terminal side of the aforementioned two reporter assay system components.

Using the genome editing technique, the two gene fragments were each knocked-in into the 3'-UTR of gene #1 and gene #2 in the genome of HeLa cells. The cells, in which the above-described two gene fragments were knocked-in in two different genomic sites, were monocloned to prepare indicator cells to be subjected to the assay system (indicator HeLa cells).

Procedures for Production of Indicator HeLa Cells

Indicator HeLa cells were produced as described below, with reference to the genome editing procedures described in Suzuki K et al Nature 540: 144-149, 2016).

(1) In order to knock-in the IRES-TMGV fragment into the target site on the genome (a first target site: 3'-UTR of gene #1) by CRISPR, a flox-blasticidin resistance gene cassette (in which the blasticidin resistance gene cassette had previously been flanked by loxP) was connected with the N-terminal side of IRES-TMGV, and thereafter, the same sequence as a nucleic acid sequence recognized by CRISPR on the genome (for the first target site) was further added to both termini, so that a plasmid was constructed with a pBluescript backbone. That is, the nucleic acid sequence is as follows. (CRISPR recognition sequence: for the first target site)-(flox-blasticidin cassette)-(IRES-TMGV)-(CRISPR recognition sequence: for the first target site). Hereinafter, this is referred to as "TMGV donor plasmid (DP-TMGV)."

(2) A plasmid necessary for causing a DNA double-strand break (DSB) to the target site on the genome (the first target site) by utilizing CRISPR was constructed based on pX330-U6-Chimeric_BB-CBh-hSpCas9 (Addgene #42230) (pV330-1$^{st}$ target).

(3) HeLa cells were seeded on a 6-cm dish ($5\times10^5$ cells per dish). The following day, "3 µg of pV330-1$^{st}$ target and 0.03 µg of DP-TMGV" were transiently transfected into the cells according to a lipofection method.

(4) From the following day after the gene transfection, blasticidin was added to the cell culture medium to a concentration of 10 µg/ml, and the cells were cultured for about 2 weeks.

(5) The HeLa cells that had proliferated in the presence of blasticidin were subjected to limiting dilution for monocloning.

(6) The genome was recovered from each monoclone, and whether or not a (flox-blasticidin cassette)-(IRES-TMGV) gene fragment had been inserted into the target site (the first target site) was confirmed by a genomic PCR method.

(7) Cre recombinase was transiently transfected into a clone, in which the (flox-blasticidin cassette)-(IRES-TMGV) gene fragment had been inserted into the target site (the cells were seeded on a 6-cm dish ($5\times10^5$ cells per dish), and on the following day, 3 µg of an iCre-IRES-puromycin expression plasmid was transfected into the cells by lipofection). From the following day after the gene transfection, puromycin was added to the cell culture medium to a concentration of 10 µg/ml, and the cells were cultured for 3 days. By this step, the blasticidin cassette was removed from the genome, so that a state, in which only IRES-TMGV was inserted into the genomic site of interest (the first target site), could be obtained.

(8) The thus established monoclone group was further sorted by the following method. GPR55 has been known as GPCR that is specifically coupled with G12/13. Hence, a plasmid cocktail consisting of a GPR55 expression plasmid+a TM3C-expression plasmid+UAS-luciferase was transfected into each of the established clones (by lipofection of 60 ng of GPR55, 10 ng of TM3C, and 30 ng of UAS-luciferase per well of a 96-well plate), and 24 hours after the gene transfection, the cells were stimulated for 6 hours with LPI (lysophosphatidylinositol: 3 concentrations of 3 uM, 300 nM and 0 nM were used), a ligand for GPR55. After the stimulation, a culture supernatant was discarded, and a substrate for luciferase was added, and then, luminescence signals were measured using a plate reader. According to this assay, a clone most sensitively responding to LPI stimulation was identified, and it was then used in the subsequent experiments (hereinafter this clone is referred to as "N182").

(9) In order to knock-in the IRES-TM3C fragment into the target site on the genome (a second target site: 3'-UTR of gene #2) by CRISPR, a flox-neomycin resistance gene cassette (in which the neomycin resistance gene cassette had previously been flanked by loxP) was connected with the N-terminal side of IRES-TM3C, and thereafter, the same sequence as a nucleic acid sequence recognized by CRISPR on the genome (for the second target site) was further added to both termini, so that a plasmid was constructed with a pBluescript backbone. That is, the nucleic acid sequence is as follows. (CRISPR recognition sequence: for the second target site)-(flox-neomycin cassette)-(IRES-TM3C)-(CRISPR recognition sequence: for the second target site).

Hereinafter, this is referred to as "TM3C donor plasmid (DP-TM3C)."

(10) A plasmid necessary for causing DSB to the target site on the genome (the second target site) by utilizing CRISPR was constructed based on pX330-U6-Chimeric_BB-CBh-hSpCas9 (Addgene #42230) (pV330-2$^{nd}$ target).

(11) N182 cells were seeded on a 6-cm dish ($5\times10^5$ cells per dish). The following day, "3 µg of pV330-2$^{nd}$ target and 0.03 µg of DP-TMGV" were transiently transfected into the cells according to a lipofection method.

(12) From the following day after the gene transfection, G418 was added to the cell culture medium to a concentration of 1 mg/ml, and the cells were cultured for about 2 weeks.

(13) Cre recombinase was transiently transfected into N182 cells that had proliferated in the presence of G418 (the cells were seeded on a 6-cm dish ($5 \times 10^5$ cells per dish), and on the following day, 3 μg of an iCre-IRES-puromycin expression plasmid was transfected into the cells by lipofection). From the day following the gene transfection, puromycin was added to the cell culture medium to a concentration of 10 μg/ml, and the cells were cultured for 3 days. By this step, the neomycin cassette was removed from the genome, so that a state, in which only IRES-TM3C was inserted into the genomic site of interest (the second target site), could be obtained.

(14) The N182 cells that had proliferated in the presence of G418 and puromycin were subjected to limiting dilution for monocloning.

(15) The genome was recovered from each monoclone, and whether or not an IRES-TM3C gene fragment had been inserted into the target site (the second target site) was confirmed by a genomic PCR method.

(16) Clones, in which the IRES-TM3C gene fragment had been inserted into the target site, were further sorted by the following method. A plasmid cocktail consisting of a GPR55 expression plasmid+UAS-luciferase was transfected into each of the established clones (by lipofection of 60 ng of GPR55 and 30 ng of UAS-luciferase per well of a 96-well plate), and 24 hours after the gene transfection, the cells were stimulated for 6 hours with LPI (lysophosphatidylinositol: 3 concentrations of 3 uM, 300 nM and 0 nM were used), a ligand for GPR55. After the stimulation, a culture supernatant was discarded, and a substrate for luciferase was added, and then, luminescence signals were measured using a plate reader. According to this assay, a clone most sensitively responding to LPI stimulation was identified (hereinafter this clone is referred to as "NCP19").

Assay Protocols of Novel GPCR Assay System
Used plasmids:
  (1) A plasmid that expresses a GPCR to be evaluated (a GPCR expression plasmid); and
  (2) UAS-luciferase (an artificial reporter gene in which the expression of luciferase is induced by sGV).
Used cells:
  NCP19 (FIG. 6).
Procedures
  Day 1: NCP19 cells were seeded on a 96-well microplates at a density of 24000 cells/well.
  Day 2: Within 24 hours after the seeding on the 96-well plate, 90 ng of DNA per well (a plasmid cocktail consisting of 60 ng of GPCR+30 ng UAS-luciferase) was transfected into the cells according to a lipofection method.
  Day 3: Twenty-four hours after the transfection, the cells were stimulated by a ligand. After the stimulation for 6 hours, a culture supernatant was discarded, and a substrate for luciferase was added, and then, luminescence signals were measured using a plate reader.

As GPCRs, the following receptors: GPR55 (G12/13-coupled GPCR), LPAR6 (G12/13-coupled GPCR), OPRM1 (Gi/o-coupled GPCR), SSTR2 (Gi/o-coupled GPCR), HRH1 (Gq-coupled GPCR), GPR119 (Gs-coupled GPCR), Adrb2 (Gs-coupled GPCR) and ADORA2A (Gs-coupled GPCR) were used.

[Conventional Method]
An attempt was made to detect GPR55 and LPAR6 according to a conventional method. The details of the conventional method are as follows.
Used cells: HeLa cells (purchased from ATCC) and HEK293T cells
Used plasmids:
  (1) Plasmids that express GPCRs to be evaluated (GPCR expression plasmids), which are, in the present experiment, GPR55- and LPAR6-expression plasmids; and
  (2) SRF-luciferase.
  Day 1: HeLa cells or HEK293T cells were seeded on a 96-well plate at a density of 24000 cells/well.
  Day 2: Within 24 hours after the seeding on the 96-well plate, 90 ng of DNA per well (a plasmid cocktail consisting of 60 ng of GPCR+30 ng of SRF-luciferase) was transfected into the cells according to a lipofection method.
  Day 3: Twenty-four hours after the transfection, the cells were stimulated by a ligand (see FIG. 7 for the stimulation concentration). After the stimulation for 6 hours, a culture supernatant was discarded, and a substrate for luciferase was added, and then, luminescence signals were measured using a plate reader.

Figure 7:
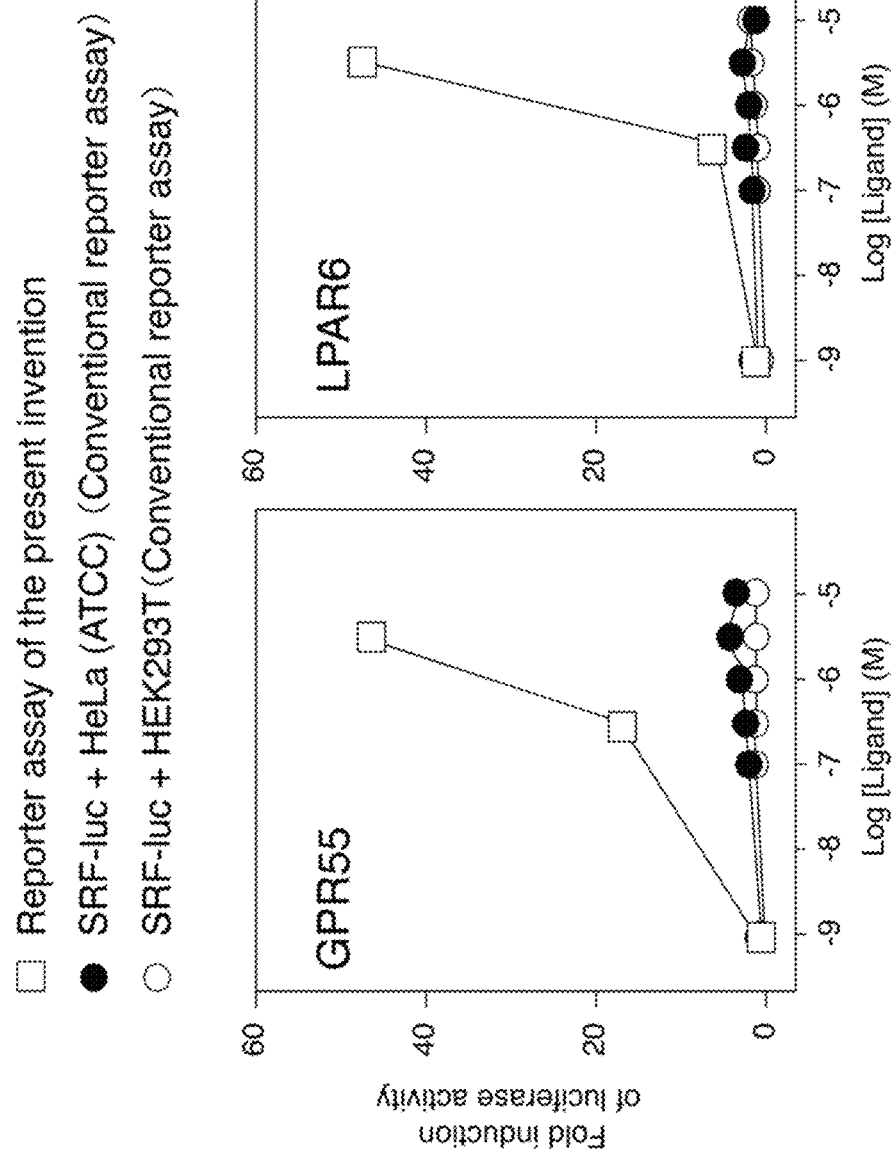
FIG. 7 is a figure showing the results obtained by detecting activation of G12/13-coupled GPCRs (GPR55 and LPAR6) by their corresponding ligands according to the assay system of the present invention and conventional methods. The horizontal axis indicates a ligand concentration, and the vertical axis indicates the luminescence intensity output in each assay system. In the assay system of the present invention, significant improvement (30 times or more) was obtained in terms of both sensitivity and S/N ratio. According to the present invention, a sensitive assay capable of monitoring activation of G12/13-coupled GPCRs can be provided.

The results are shown in FIG. 7 as "SRF-luc+HeLa (ATCC)" and "SRF-luc+HEK293T."

Moreover, regarding GPR55 and LPAR6, signal detection was also performed using an exogenous protease. This assay system is different from the assay system using NCP19 cells, in that the protease is exogenously introduced via a plasmid expressing the protease with a constitutive promoter. More details are as follows.
Used cells: N182 cells (cells in which only TMGV had previously knocked-in into the genome)
Used plasmids:
  (1) Plasmids that express GPCRs to be evaluated (GPCR expression plasmids), which are, in the present experiment, GPR55- and LPAR6-expression plasmids;
  (2) a TM3C expression plasmid (a plasmid expressing a protease with a constitutive promotor); and
  (3) UAS-luciferase.
  Day 1: N182 cells were seeded on a 96-well plate at a density of 24000 cells/well.
  Day 2: Within 24 hours after the seeding on the 96-well plate, 100 ng of DNA per well (a plasmid cocktail consisting of 60 ng of GPCR+10 ng of TM3C+30 ng of UAS-luciferase) was transfected into the cells according to a lipofection method.
  Day 3: Twenty-four hours after the transfection, the cells were stimulated by a ligand (see FIG. 8 for the stimulation concentration). After the stimulation for 6 hours, a culture supernatant was discarded, and a substrate for luciferase was added, and then, luminescence signals were measured using a plate reader.

Figure 8:
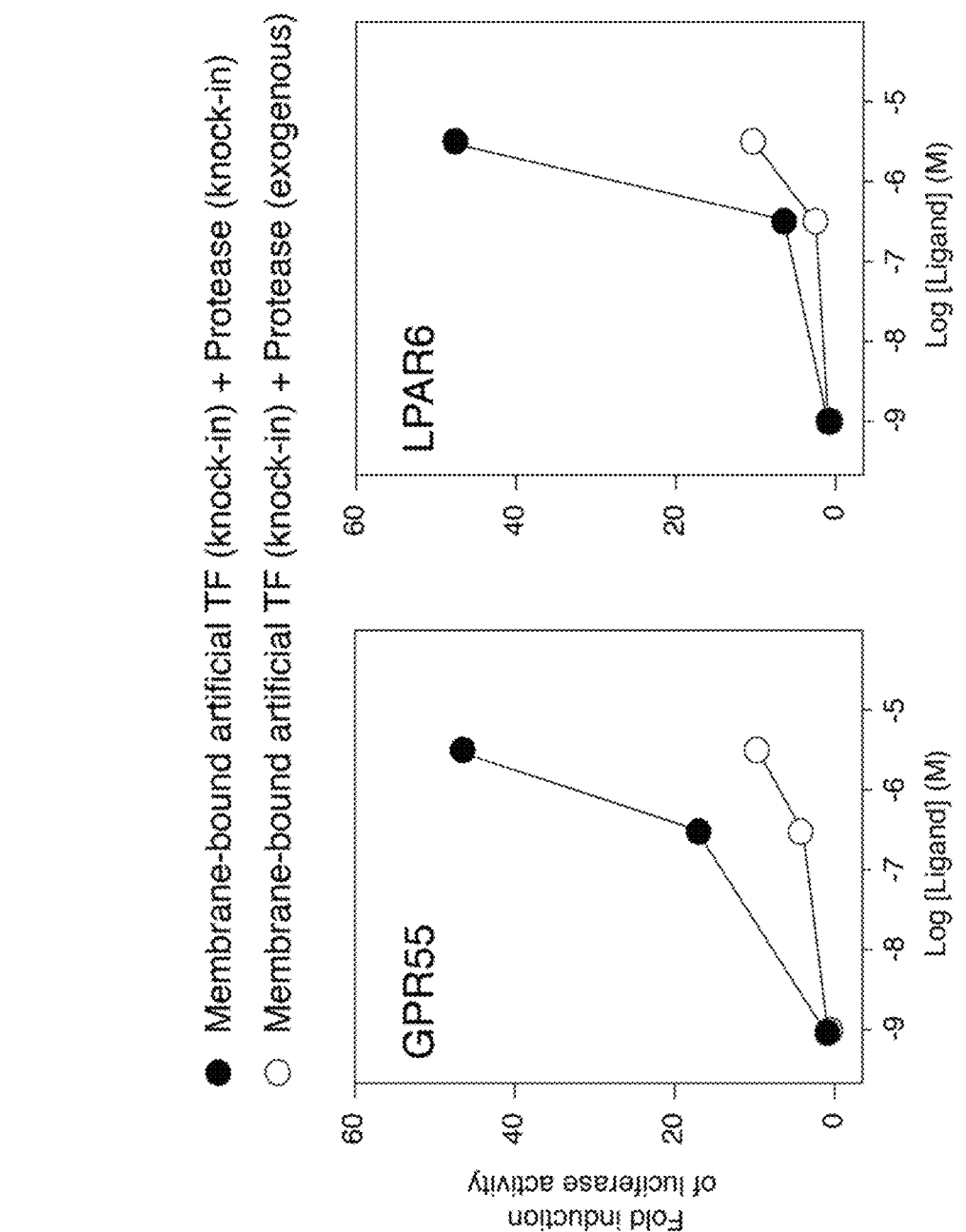
FIG. 8 is a figure showing that synergistic signal amplification is actually generated by utilizing a plurality of loci whose expressions are induced by ligand stimulation. The horizontal axis indicates a ligand concentration, and the vertical axis indicates the luminescence intensity output in each assay system. The obtained results are consistent with the proof-of-concept experiment shown in FIG. 3.

The results are shown in FIG. 8 as "cell membrane-bound artificial transcription factor (knock-in)+protease (exogenous)."

Figure 10:
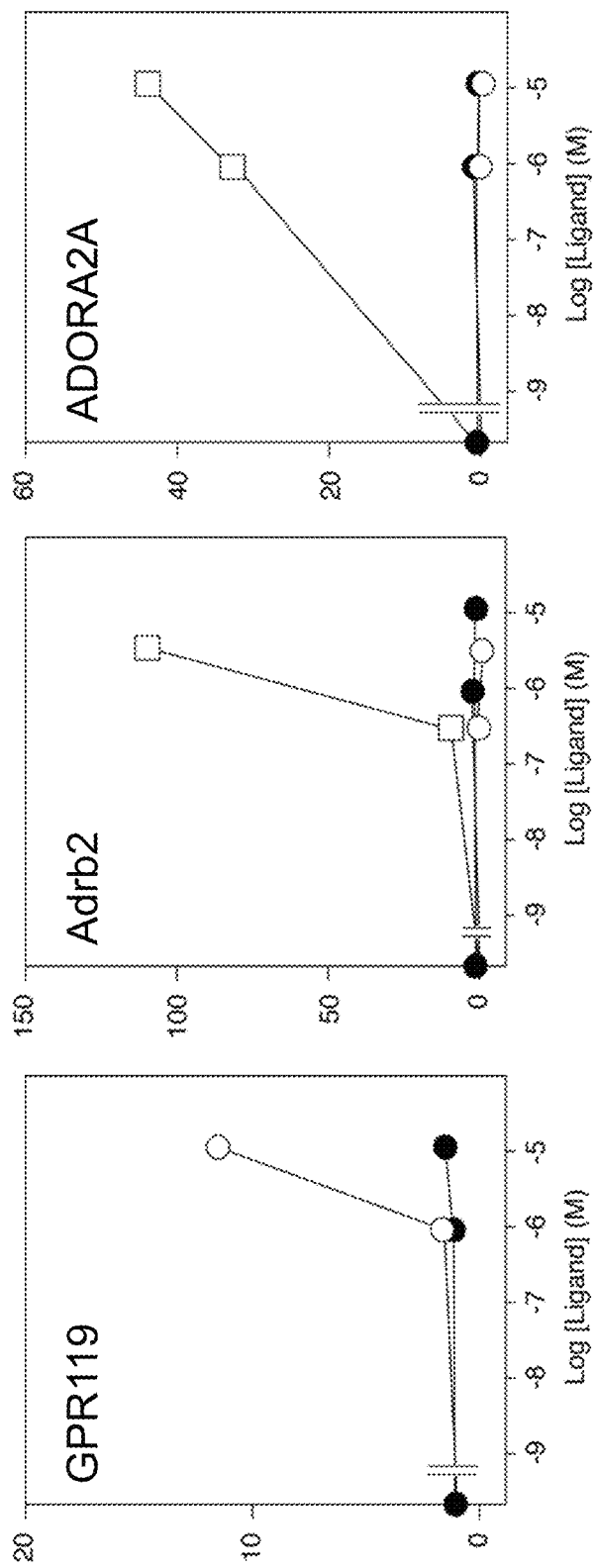
FIG. 10 is a figure showing that, by using a G12/s chimeric G protein, activation of GPCRs coupled with Gs can be detected according to the assay system of the present invention. The filled circle indicates the results of the cAMP response element (CRE)-reporter assay, which had been conventionally considered to be able to monitor activation of Gs. As shown in the figure regarding a β2 adrenergic receptor (Adrb2) and an adenosine 2A receptor (ADORA2A), not all Gs-coupled GPCRs can be evaluated by the CRE-reporter system. However, activation of such GPCRs coupled with Gs can also be detected by the present invention.

Furthermore, regarding GPR119 (Gs), Adrb2 (Gs), and ADORA2A (Gs), detection was also performed using a Cre reporter system that has been conventionally used in activation of Gs. More details are as follows.
Used cells: HeLa cells
Used plasmids:
  (1) Plasmids that express GPCRs to be evaluated (GPCR expression plasmids), which are, in the present experiment, GPR119-, Adrb2- and ADORA2A-expression plasmids; and (2) CRE-luciferase.
Day 1: HeLa cells were seeded on a 96-well plate at a density of 24000 cells/well.
Day 2: Within 24 hours after the seeding on the 96-well plate, 90 ng of DNA per well (a plasmid cocktail consisting of 60 ng of GPCR+30 ng of CRE-luciferase) was transfected into the cells according to a lipofection method.
Day 3: Twenty-four hours after the transfection, the cells were stimulated by a ligand (see FIG. 10 for the stimulation concentration). After the stimulation for 6 hours, a culture supernatant was discarded, and a substrate for luciferase was added, and then, luminescence signals were measured using a plate reader. The results are shown in FIG. 10 as "CRE-reporter (conventional method)."

[Results]

Signals obtained from each assay system by addition of various concentrations of ligands (luminescent intensity and magnification of change from signals when the ligand had the lowest concentration) are shown in FIG. 7 to FIG. 11. According to the above-described assay protocols, an increase in the signals along with an increase in the ligand concentration was observed.

[Consideration]

Using the above-described assay protocols, activation of the "G12/13-coupled GPCR" could be evaluated without problems (FIGS. 7 and 8). Thus, one of the purposes of the present assay system, namely, evaluation of the "G12/13-coupled GPCR" with high sensitivity was achieved. According to the conventional method, such activation could not be evaluated (FIG. 7).

Moreover, when compared with a case where one of the factors was not knocked-in into a locus (in the case of using an exogenous protease), an increase in the ligand concentration-dependent signals was further greatened (FIG. 8). These results suggest that it is important for an increase in signals that each of the two factors is forced to be influenced by transcriptional regulation downstream of the ligand stimulation.

Figure 9:
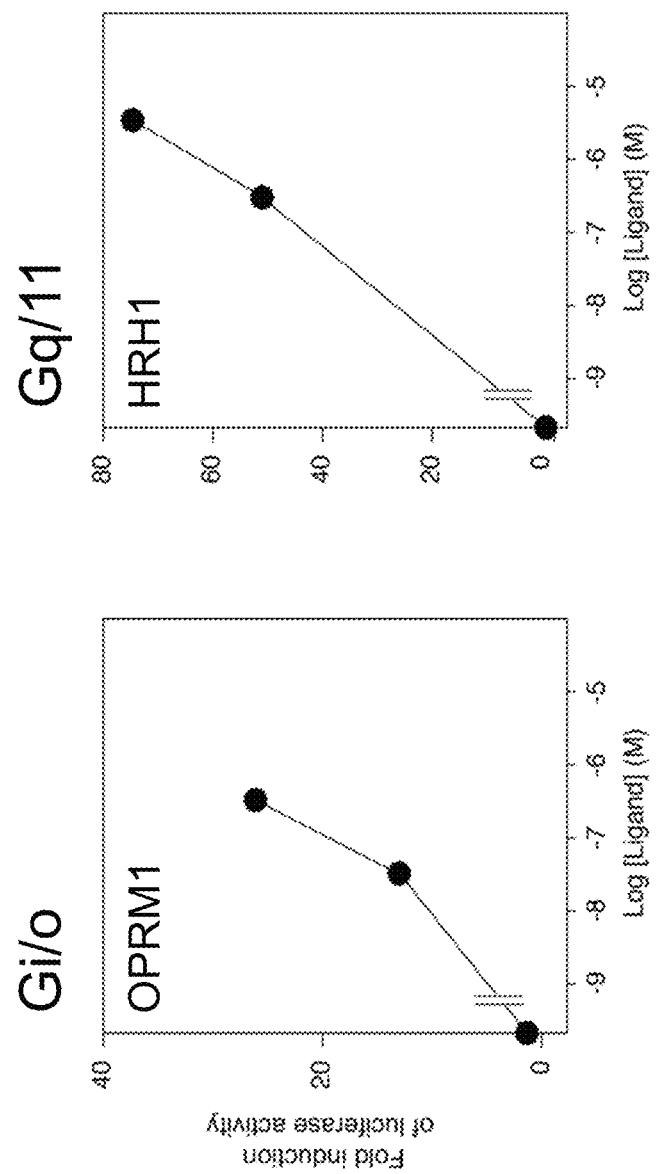
FIG. 9 is a figure showing that activation of GPCRs coupled with Gi/o G proteins and activation of GPCRs coupled with Gq/11 G proteins can be monitored by the assay system of the present invention. The horizontal axis indicates a ligand concentration, and the vertical axis indicates the luminescence intensity output in each assay system. Conventionally, there had been no good reporter systems capable of monitoring activation of Gi/o, but according to the present invention, signals by activation of Gi/o were unexpectedly detected.
Figure 11:
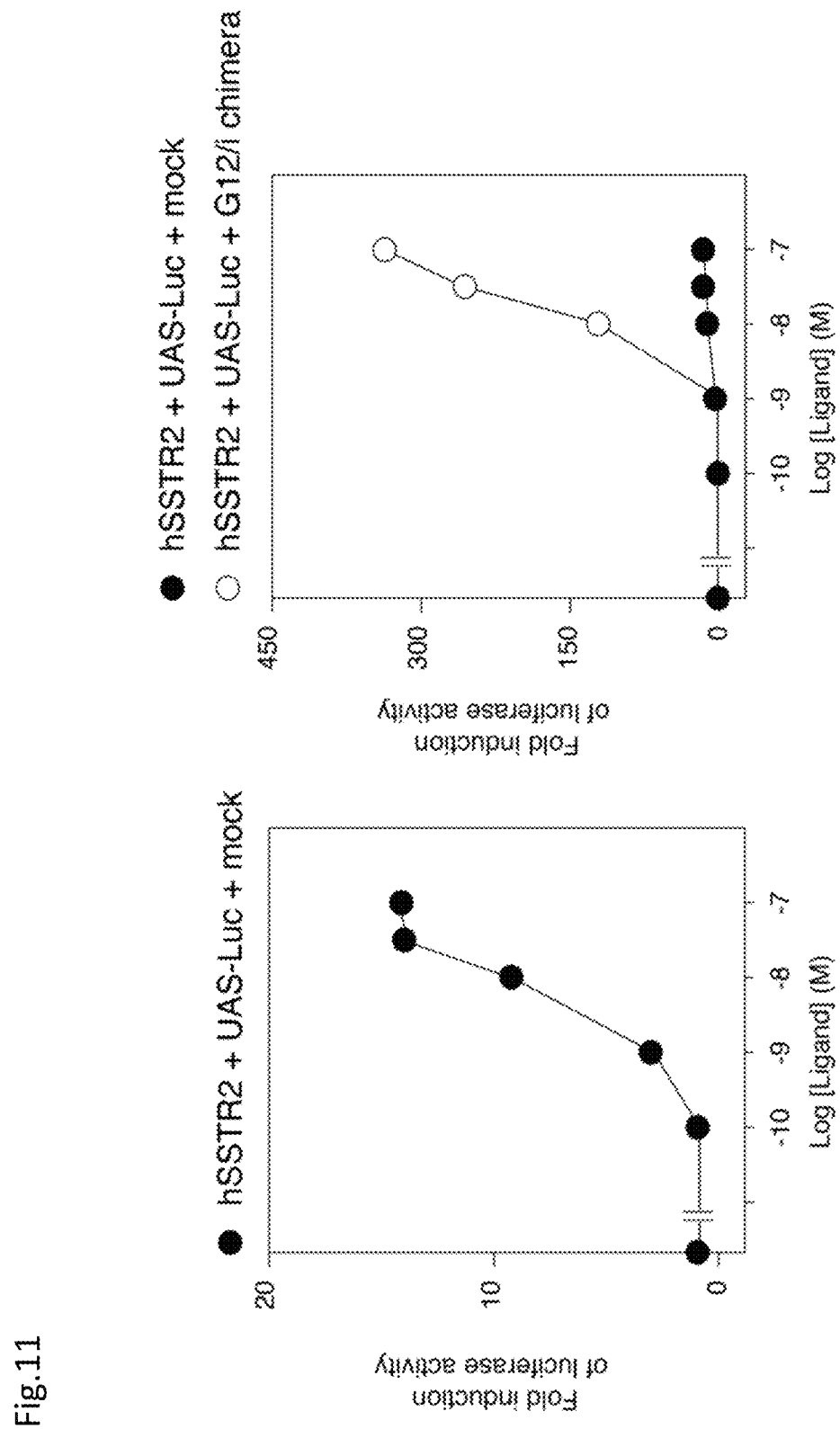
FIG. 11 is a figure showing the results obtained by detecting activation of hSSTR2 according to the assay system of the present invention. The left figure shows the results obtained in the case of not using a G12/i chimeric protein, whereas the right figure shows the results obtained in the presence and absence of a G12/i chimera. It is to be noted that the scale of the vertical axis is about 20 times different between the left figure and the right figure.

Furthermore, using the same assay protocols as described above, the "Gq-coupled GPCRs" and the "Gi-coupled GPCRs" could also be evaluated (FIG. 9 and FIG. 11). Regarding the Gs-coupled GPCRs, although activation of the tested three Gs-coupled GPCRs could not be detected by the CRE-reporter assay as a conventional method, the signals were detected in GPR119 by the above-described assay protocols (FIG. 10).

Example A4: Detection of Activation of Receptor Tyrosine Kinase Flt3

[Overview]

The present example is intended to demonstrate that not only the activated state of GPCRs but also the activated state of other receptors can be monitored according to an assay system using NCP19 cells. In the present example, as one example of cell membrane receptors other than GPCRs, human Flt3 (hFlt3) belonging to the receptor tyrosine kinase family was used as an experimental target.

[Materials and Methods]
Used cells: NCP19
Used plasmids:
(1) a plasmid that expresses hFlt3 (an hFlt3 expression plasmid); and
(2) UAS-luciferase.

Day 1: NCP19 cells were seeded on a 96-well plate at a density of 24000 cells/well.
Day 2: Within 24 hours after the seeding on the 96-well plate, 90 ng of DNA per well (a plasmid cocktail consisting of 60 ng of hFlt3+30 ng of UAS-luciferase) was transfected into the cells according to a lipofection method.
Day 3: Twenty-four hours after the transfection, the cells were stimulated by a ligand (Flt3-ligand: at concentrations of 30, 3, 0.3, 0.03, and 0 ng/ml). After the stimulation for 6 hours, a culture supernatant was discarded, and a substrate for luciferase was added, and then, luminescence signals were measured using a plate reader.

Figure 12:
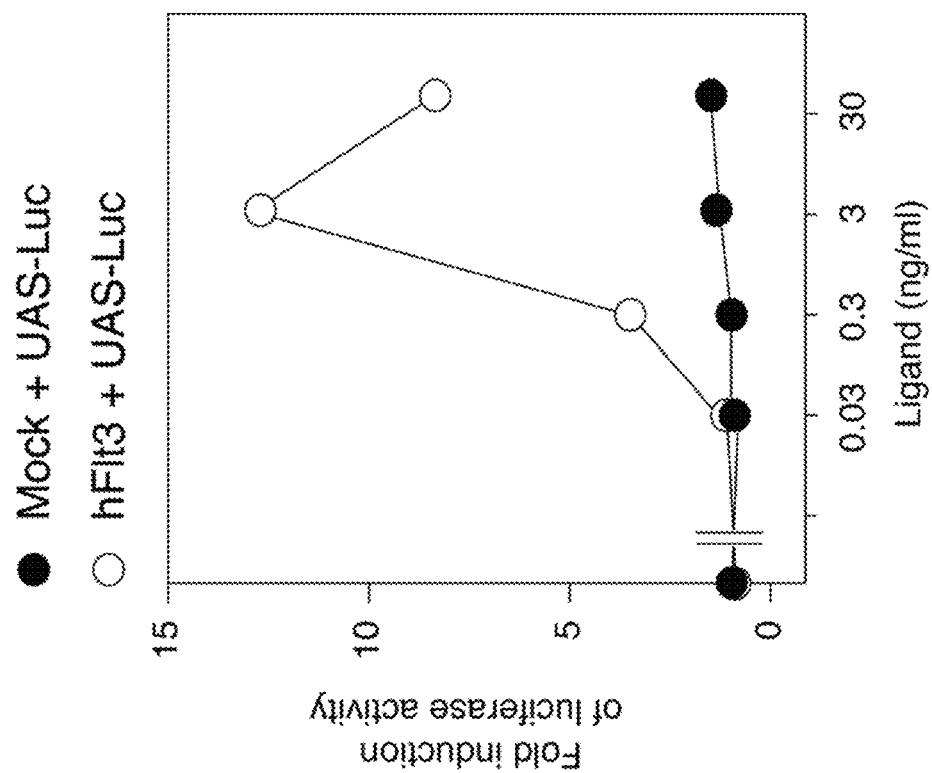
FIG. 12 is a figure showing the results obtained by detecting activation of hFlt3 according to the assay system of the present invention. The horizontal axis indicates a ligand concentration, and the vertical axis indicates the luminescence intensity output at each ligand concentration.

The results are shown in FIG. 12. As shown in FIG. 12, activation of hFlt3 by addition of the Flt3-ligand was detected as the luminescence of luciferase. It was demonstrated that not only the activated state of GPCRs but also the activated state of other receptors can be monitored according to the assay system using NCP19 cells, in which TMGV and TM3C are knocked-in into the transcriptional regulatory regions of NR4A1 and CTGF genes.

Example A5: Detection of Activation of Human EGF Receptor

[Overview]

The present example is intended to demonstrate that not only the activated state of GPCRs but also the activated state of other receptors can be monitored according to an assay system using NCP19 cells. In the present example, as one example of cell membrane receptors other than GPCRs, human EGF receptors belonging to the receptor tyrosine kinase family were used as experimental targets. Besides, the human EGF receptors hEGFR, hErbB2 and hErb3 are endogenously expressed in NCP19 cells.

[Materials and Methods]
Used cells: NCP19
Used plasmid: UAS-luciferase
Day 1: NCP19 cells were seeded on a 96-well plate at a density of 24000 cells/well.
Day 2: Within 24 hours after the seeding on the 96-well plate, 30 ng of DNA per well (30 ng of UAS-luciferase) was transfected into the cells according to a lipofection method.
Day 3: Twenty-four hours after the transfection, the cells were stimulated by a ligand (EGF: at concentrations of 10, 1, 0.1, 0.01, and 0 nM). After the stimulation for 6 hours, a culture supernatant was discarded, and a substrate for luciferase was added, and then, luminescence signals were measured using a plate reader.

Figure 13:
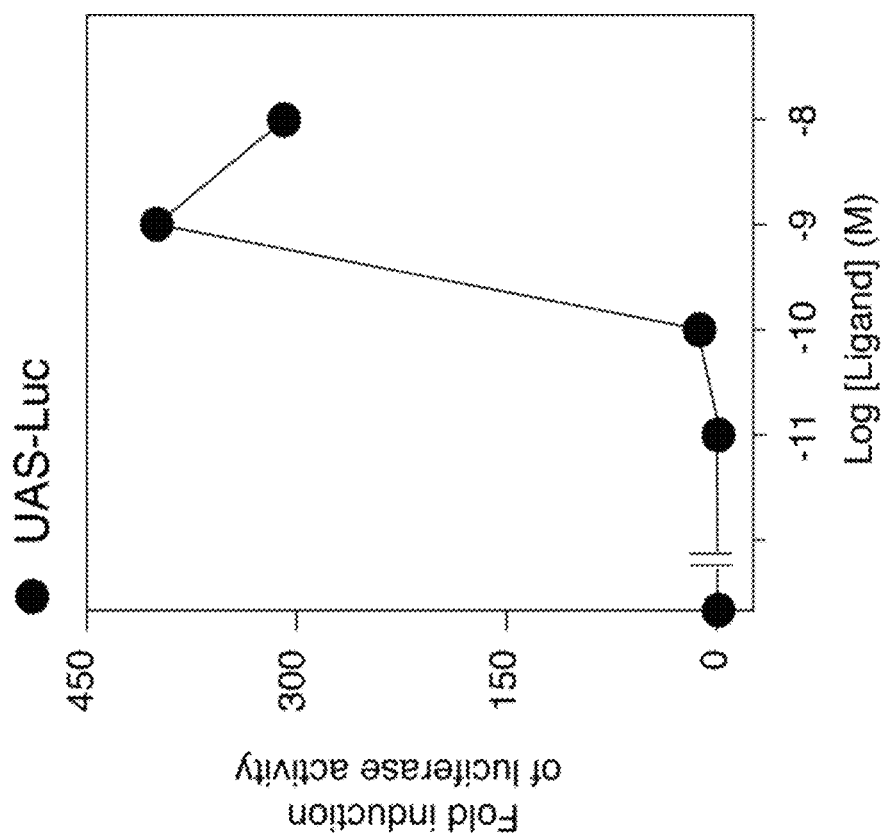
FIG. 13 is a figure showing the results obtained by detecting activation of a human EGF receptor according to the assay system of the present invention. The horizontal axis indicates a ligand concentration, and the vertical axis indicates the luminescence intensity output at each ligand concentration. It is to be noted that a human EGF receptor endogenously expressed in cells is utilized in the present assay.

The results are shown in FIG. 13. As shown in FIG. 13, activation of the EGF receptors by the addition of EGF was detected as the luminescence of luciferase. It was demonstrated that not only the activated state of GPCRs but also the activated state of other receptors can be monitored according to the assay system using NCP19 cells, in which TMGV and TM3C are knocked-in into the transcriptional regulatory regions of NR4A1 and CTGF genes.

Example A6: Analysis of GPCRs

According to the methods described in the above examples, any of the following GPCRs is expressed in cells. According to the methods described in the above examples, cells, in which the GPCRs are expressed, are stimulated by ligands, and the activated state of the receptors is monitored.

TABLE 4-1

|   | #1-#20 | #21-#40 | #41-#60 | #61-#80 | #81-#100 | #101-#120 | #121-#140 | #141-#160 |
|---|---|---|---|---|---|---|---|---|
| 1 | HTR1A | ADORA3 | CALCRL | ACKR4(CCR11) | DRD1 | GALR2 | GPR109B | MCHR2 |
| 2 | HTR1B | ADRA1A | CASR | CCRL2 | DRD2 | GALR3 | KISS1R | MC1R |
| 3 | HTR1D | ADRA1B | GPRC6A | ACKR1(CCBP1) | DRD3 | GPR151(GALR4) | LTB4R | MC2R |
| 4 | HTR1E | ADRA1D | CNR1 | ACKR2(CCBP2) | DRD4 | GHSR | LTB4R2 | MC3R |
| 5 | HTR1F | ADRA2A | CNR2 | CXCR1 | DRD5 | GHRHR | CYSLTR1 | MC4R |
| 6 | HTR2A | ADRA2B | GPR18 | CXCR2 | EDNRA | GIPR | CYSLTR2 | MC5R |
| 7 | HTR2B | ADRA2C | GPR55 | CXCR3 | EDNRB | GLP1R | OXER1(GPR170) | MTNR1A |
| 8 | HTR2C | ADRB1 | GPR119 | CXCR4 | GPR30 | GLP2R | PTAFR | MTNR1B |
| 9 | HTR4 | ADRB2 | CMKLR1 | CXCR5 | GPR183 | GCGR | LPAR1 | GRM1 |
| 10 | HTR5A | ADRB3 | GPR1 | CXCR6 | FPR1 | SCTR | LPAR2 | GRM2 |
| 11 | HTR6 | AGTR1 | CCR1 | ACKR3(CXCR7) | FPR2 | FSHR | LPAR3 | GRM3 |
| 12 | HTR7 | AGTR2 | CCR2 | XCR1 | FPR3 | LHCGR | LPAR4 | GRM4 |
| 13 | CHRM1 | APLNR | CCR3 | CX3CR1 | GPR40 | TSHR | LPAR5 | GRM5 |
| 14 | CHRM2 | GPBAR1(TGR5) | CCR4 | CCKAR | GPR41 | GNRHR | LPAR6 | GRM6 |
| 15 | CHRM3 | BRS3 | CCR5 | CCKBR | GPR43 | HRH1 | S1PR1 | GRM7 |
| 16 | CHRM4 | GRPR | CCR6 | C3AR1 | GPR84 | HRH2 | S1PR2 | GRM8 |
| 17 | CHRM5 | NMBR | CCR7 | C5AR1 | GPR120 | HRH3 | S1PR3 | MLNR |
| 18 | ADORA1 | BDKRB1 | CCR8 | C5AR2 | GABBR1 | HRH4 | S1PR4 | NMUR1 |
| 19 | ADORA2A | BDKRB2 | CCR9 | CRHR1 | GABBR2 | GPR81 | S1PR5 | NMUR2 |
| 20 | ADORA2B | CALCR | CCR10 | CRHR2 | GALR1 | GPR109A | MCHR1 | NPFFR1 |

TABLE 4-2

|   | #161-#180 | #181-#200 | #201-#220 | #221-#240 | #241-#260 | #261-#280 | #281-#300 | #301-#314 |
|---|---|---|---|---|---|---|---|---|
| 1 | NPFFR2 | P2RY6 | TBXA2R | TAAR1 | GPR12 | GPR61 | GPR153 | MRGPRX3 |
| 2 | NPSR1 | P2RY11 | F2R | TAAR2 | GPR15 | GPR62 | GPR160 | MRGPRX4 |
| 3 | NPBWR1 | P2RY12 | F2RL1 | TAAR5 | GPR17 | GPR63 | GPR161 | GPR156 |
| 4 | NPBWR2 | P2RY13 | F2RL2 | TAAR6 | GPR19 | GPR75 | GPR162 | GPR158 |
| 5 | NPY1R | P2RY14 | F2RL3 | TAAR8 | GPR20 | GPR78 | GPR171 | GPR179 |
| 6 | NPY2R | P2RY8 | QRFPR | TAAR9 | GPR21 | GPR82 | GPR173 | GPRC5A |
| 7 | NPY4R | P2RY10 | RXFP1 | UTS2R | GPR22 | GPR83 | GPR174 | GPRC5B |
| 8 | NPY5R | PTH1R | RXFP2 | AVPR1A | GPR25 | GPR85 | GPR176 | GPRC5C |
| 9 | NTSR1 | PTH2R | RXFP3 | AVPR1B | GPR26 | GPR87 | GPR182 | GPRC5D |
| 10 | NTSR2 | PROKR1 | RXFP4 | AVPR2 | GPR27 | GPR88 | LGR4 | GPR107 |
| 11 | OPRD1 | PROKR2 | SSTR1 | OXTR | GPR31 | GPR101 | LGR5 | GPR137 |
| 12 | OPRK1 | PRLHR | SSTR2 | ADCYAP1R1 | GPR32 | GPR135 | LGR6 | GPR143 |
| 13 | OPRM1 | PTGDR | SSTR3 | VIPR1 | GPR34 | GPR139 | MAS1 | GPR157 |
| 14 | OPRL1 | PTGDR2 | SSTR4 | VIPR2 | GPR35 | GPR141 | MASL1 | GPR175 |
| 15 | HCRTR1 | PTGER1 | SSTR5 | GPR4 | GPR37 | GPR142 | MRGPRD |  |
| 16 | HCRTR2 | PTGER2 | GPR91(SUCNR1) | GPR65(TDAG8) | GPR37L1 | GPR146 | MRGPRE |  |
| 17 | OXGR1(GPR80/99) | PTGER3 | TACR1 | GPR68(OGR1) | GPR39 | GPR148 | MRGPRF |  |
| 18 | P2RY1 | PTGER4 | TACR2 | GPR132(G2A) | GPR45 | GPR149 | MRGPRG |  |
| 19 | P2RY2 | PTGFR | TACR3 | GPR3 | GPR50 | GPR150 | MRGPRX1 |  |
| 20 | P2RY4 | PTGIR | TRHR | GPR6 | GPR52 | GPR152 | MRGPRX2 |  |

Example B1: Chimeric G Proteins

[Overview]

The activation of some Gs-coupled GPCRs (Adrb2 and ADORA2A) was not detected, when the above-described assay protocols were applied (FIG. 10). In order to implement efficient evaluation of the "Gs-coupled GPCRs" by modifying the protocols, the following experiment was carried out.

[Materials and Methods]

Day 2 in the protocols of Example A3 was modified as follows, and other procedures were carried out in the same manner as that of Example A3. Thereafter, the activation of Adrb2 and ADORA2A was evaluated.

<Modification>

Day 2: Within 24 hours after the seeding on the 96-well plate, 120 ng of DNA per well (a plasmid cocktail consisting of 60 ng of GPCR+30 ng of UAS-luciferase+30 ng of G12/s chimera) was transfected into the cells according to a lipofection method.

G12/s Chimera

The coupling of a G protein with a receptor is determined by an amino acid sequence consisting of several amino acids on the C-terminus of a Gα subunit. Accordingly, there was produced a Gα12/s chimera (hereinafter simply referred to as "G12/s chimera"), in which a truck portion is entirely derived from Gα12 and only the last 6 amino acids on the C-terminus are derived from Gαs (see the amino acid sequences below). This G12/s chimera can be coupled with the "Gs-coupled GPCRs" and can trigger the same signals as intracellular signals generated by activation of wild-type G12, in cells.

For the production of chimeric G proteins, please refer to Conklin B R et al., Nature 363: 274-276, 1993; and Conklin B R et al., Mol. Pharmacology 50: 885-890, 1996.

By utilizing such a chimera together with a system capable of evaluating activation of a G12/13 protein with high efficiency, the activation of GPCRs coupled with the Gs protein can be successfully evaluated. It has been reported that a Gq/12 chimera was constructed for the purpose of converting the activation of a G12/13 protein to a Gq pathway and evaluating it. However, when it is difficult to evaluate the activation of the G12/13 protein, the G12/s chimera cannot be used for the same purpose.

[Formula 1]
Human G12 Amino Acid Sequence (NP_031379)

(SEQ ID NO: 4)
MSGVVRTLSRCLLPAEAGGARERRAGSGARDAEREARRRSRDIDALLARE

RRAVRRLVKILLLGAGESGKSTFLKQMRIIHGREFDQKALLEFRDTIFDN

ILKGSRVLVDARDKLGIPWQYSENEKHGMFLMAFENKAGLPVEPATFQLY

VPALSALWRDSGIREAFSRRSEFQLGESVKYFLDNLDRIGQLNYFPSKQD

ILLARKATKGIVEHDFVIKKIPFKMVDVGGQRSQRQKWFQCFDGITSILF

MVSSSEYDQVLMEDRRTNRLVESMNIFETIVNNKLFFNVSIILFLNKMDL

LVEKVKTVSIKKHFPDFRGDPHRLEDVQRYLVQCFDRKRRNRSKPLFHHF

TTAIDTENVRFVFHAVKDTILQENLKDIMLQ

[Formula 2]
Human Gs Amino Acid Sequence (NP_000507)

(SEQ ID NO: 5)
MGCLGNSKTEDQRNEEKAQREANKKIEKQLQKDKQVYRATHRLLLLGAGE

SGKSTIVKQMRILHVNGFNGEGGEEDPQAARSNSDGEKATKVQDIKNNLK

EAIETIVAAMSNLVPPVELANPENQFRVDYILSVMNVPDFDFPPEFYEHA

KALWEDEGVRACYERSNEYQLIDCAQYFLDKIDVIKQADYVPSDQDLLRC

RVLTSGIFETKFQVDKVNFHMFDVGGQRDERRKWIQCFNDVTAIIFVVAS

SSYNMVIREDNQTNRLQEALNLFKSIWNNRWLRTISVILFLNKQDLLAEK

VLAGKSKIEDYFPEFARYTTPEDATPEPGEDPRVTRAKYFIRDEFLRIST

ASGDGRHYCYPHFTCAVDTENIRRVENDCRDIIQRMHLRQYELL

[Formula 3]
G12/s Chimera Amino Acid Sequence Used In The Present Assay

MSGVVRTLSRCLLPAEAGGARERRAGSGARDAEREARRRSRDIDALLARE

RRAVRRLVKILLLGAGESGKSTFLKQMRIIHGREFDQKALLEFRDTIFDN

ILKGSRVLVDARDKLGIPWQYSENEKHGMFLMAFENKAGLPVEPATFQLY

VPALSALWRDSGIREAFSRRSEFQLGESVKYFLDNLDRIGQLNYFPSKQD

ILLARKATKGIVEHDFVIKKIPFKMVDVGGQRSQRQKWFQCFDGITSILF

MVSSSEYDQVLMEDRRTNRLVESMNIFETIVNNKLFFNVSIILFLNKMDL

LVEKVKTVSIKKHFPDFRGDPHRLEDVQRYLVQCFDRKRRNRSKPLFHHF

TTAIDTENVRFVFHAVKDTILQENLRQYELL
(SEQ ID NO: 6, the underline indicates an amino acid sequence portion derived from Gs)

[Results]
In the case of using the protocols of the present example, an increase in the ligand concentration-dependent signals could be detected regarding both Adrb2 and ADORA2A (FIG. 10).

[Consideration]
It is demonstrated that the activity of the "Gs-coupled GPCRs" can also be evaluated efficiently by performing the above-described modification. Moreover, from these results, it is considered that the above-modified protocols are desirably used upon the evaluation of a GPCR whose G protein to be coupled therewith is unknown (an orphan GPCR).

Taking into consideration the results of the present example together with the results of Example A, it was revealed that when the above-described (1) IRES-TMGV and (2) IRES-TM3C were knocked-in into the 3'-UTR of two different genes whose expressions are induced when the G12/13 protein is specifically activated in the GPCR assay system of the present invention to establish reporter cells NCP19, and when the reporter cells NCP19 were then used, not only the "G12/13-coupled GPCRs" could be evaluated with high sensitivity, as expected, but also, "Gs-coupled GPCRs," "Gq-coupled GPCRs" and "Gi-coupled GPCRs" could be comprehensively evaluated with high sensitivity, which was an unexpected advantage.

Example B2: Chimeric G Protein Based on G12

[Overview]
The present example is intended to demonstrate that chimeric G proteins other than the G12/s chimera are also useful in the assay system using NCP19 cells. Human somatostatin type 2 receptor (hSSTR2) known as a receptor coupled with Gi and a G12/i chimera were used as experimental targets.

[Materials and Methods]
Used cells: NCP19
Used plasmids:
(1) an hSSTR2 expression plasmid;
(2) UAS-luciferase; and
(3) a G12/i chimeric protein expression plasmid (G12/i expression plasmid).

The amino acid sequence of human Gi1 and the amino acid sequence of G12/i chimera used in the present example are as follows.

[Formula 4]
Human gi1 Amino Acid Sequence (SEQ ID NO: 7)
MGCTLSAEDKAAVERSKMIDRNLREDGEKAAREVKLLLLGAGESGKSTIV

KQMKIIHEAGYSEEECKQYKAVVYSNTIQSIIAIIRAMGRLKIDFGDSAR

ADDARQLFVLAGAAEEGFMTAELAGVIKRLWKDSGVQACFNRSREYQLND

SAAYYLNDLDRIAQPNYIPTQQDVLRTRVKTTGIVETHFTFKDLHFKMFD

VGGQRSERKKWIHCFEGVTAIIFCVALSDYDLVLAEDEEMNRMHESMKLF

DSICNNKWFTDTSIILFLNKKDLFEEKIKKSPLTICYPEYAGSNTYEEAA

AYIQCQFEDLNKRKDTKEIYTHFTCATDTKNVQFVFDAVIDVIIKNNLKD

CGLF

[Formula 5]
G12/i1 Chimera Amino Acid Sequence

MSGVVRTLSRCLLPAEAGGARERRAGSGARDAEREARRRSRDIDALLARE

RRAVRRLVKILLLGAGESGKSTFLKQMRIIHGREFDQKALLEFRDTIFDN

ILKGSRVLVDARDKLGIPWQYSENEKHGMFLMAFENKAGLPVEPATFQLY

VPALSALWRDSGIREAFSRRSEFQLGESVKYFLDNLDRIGQLNYFPSKQD

ILLARKATKGIVEHDFVIKKIPFKMVDVGGQRSQRQKWFQCFDGITSILF

-continued

MVSSSEYDQVLMEDRRTNRLVESMNIFETIVNNKLFFNVSIILFLNKMDL

LVEKVKTVSIKKHFPDFRGDPHRLEDVQRYLVQCFDRKRRNRSKPLFHHF

TTAIDTENVRFVFHAVKDTILQENLKDCGLE
(SEQ ID NO: 8, the underline indicates an amino
acid sequence portion derived from Gil)

Day 1: NCP19 cells were seeded on a 96-well plate at a density of 24000 cells/well.

Day 2: Within 24 hours after the seeding on the 96-well plate, 100 ng of DNA per well (a plasmid cocktail consisting of 50 ng of hSSTR2+25 ng of UAS-luciferase+25 ng of G12/i chimera (or mock)) was transfected into the cells according to a lipofection method.

Day 3: Twenty-four hours after the transfection, the cells were stimulated by a ligand (somatostatin) (SST14: at concentrations of 100, 30, 10, 1, 0.1, and 0 nM). After the stimulation for 6 hours, a culture supernatant was discarded, and a substrate for luciferase was added, and then, luminescence signals were measured using a plate reader.

[Results]

The results are shown in FIG. 11. The activity can be sufficiently detected without G12/i chimeric proteins (FIG. 11, left). However, the activity-detecting ability is significantly improved in the presence of the chimeric protein (FIG. 11, right). It is to be noted that the scale of the vertical axis is different between the left and right figures by about 20 times.

Example C: Procedures for Identifying a Group of Genes Whose Expressions are Induced by Activation of Proteins

[Overview]

The present examples is intended to demonstrate a method for identifying a gene whose expression is induced by the activation of a protein of interest in used cells.

[Materials and Methods]

The two receptors, GPR55 and LPAR6, are known as GPCRs that specifically activate the G protein G12/13. Hence, using HeLa cells, GPR55, and LPAR6, experiments were carried out under the following seven conditions. LPI and LPA (Lysophosphatidic acid) have already been known to function as ligands for GPR55 and LPAR6, respectively.

Condition 1 HeLa cells (wild type)

Condition 2 HeLa cells (wild type)+mock+10 μM LPI: stimulation for 1 hour

Condition 3 HeLa cells (wild type)+GPR55+vehicle: stimulation for 1 hour

Condition 4 HeLa cells (wild type)+GPR55+10 μM LPI: stimulation for 1 hour

Condition 5 HeLa cells (wild type)+mock+10 μM LPA: stimulation for 1 hour

Condition 6 HeLa cells (wild type)+LPAR6+vehicle: stimulation for 1 hour

Condition 7 HeLa cells (wild type)+LPAR6+10 μM LPA: stimulation for 1 hour

Figure 14:
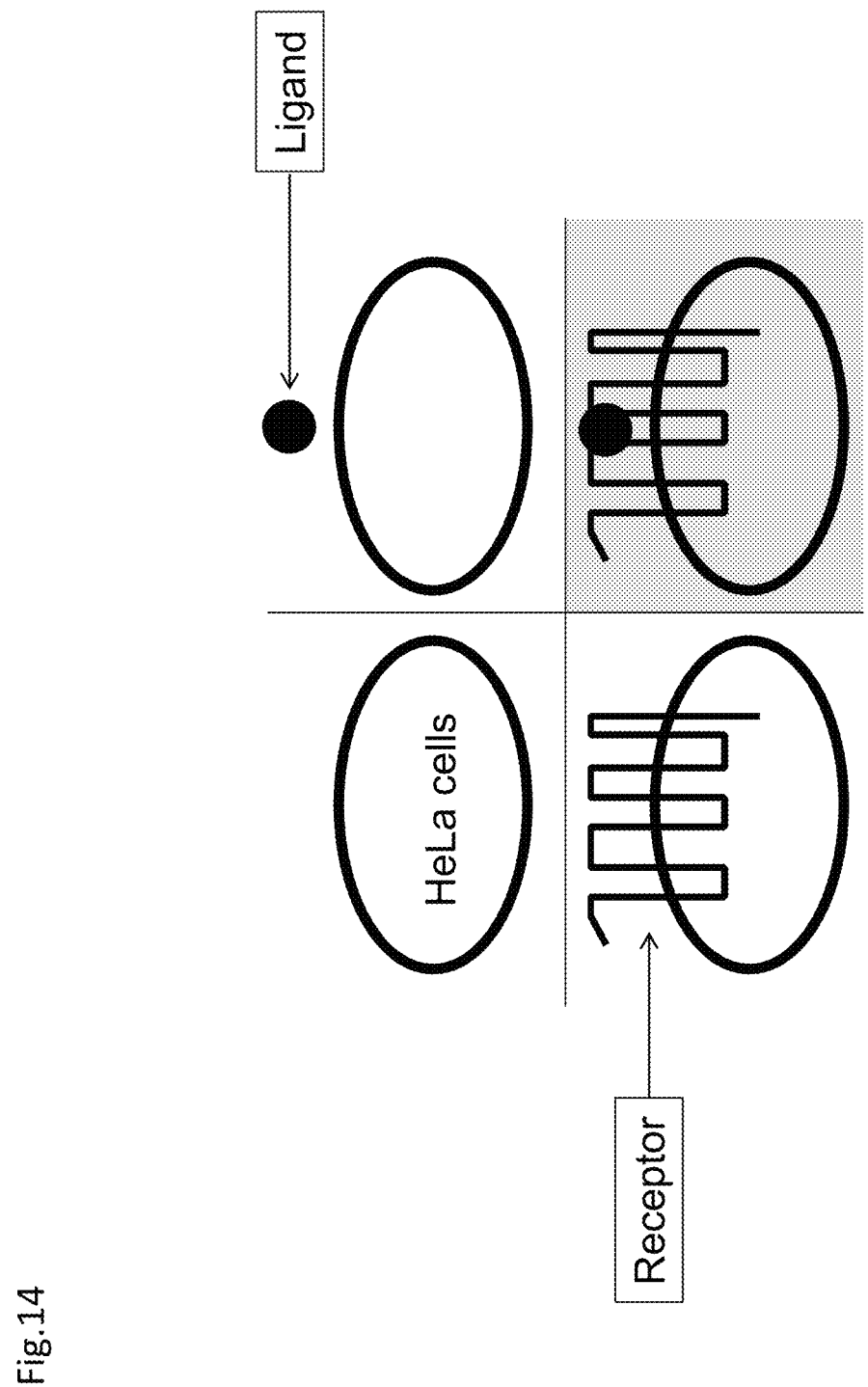
FIG. 14 is a schematic figure showing an example of a method for identifying a gene whose expression is induced by activation of a certain protein in a certain cell. For example, a gene expression response induced when G12/13 is specifically activated in a HeLa cell can be analyzed on a genome-wide basis, using a next-generation sequencer. In this case, gene expression can be measured in 4 groups, namely, without addition of a ligand (left) or with addition of a ligand (right), and without overexpression of a receptor (upper) and with overexpression of a receptor (lower). A gene whose expression is induced in a group involving with overexpression of a receptor and with addition of a ligand (lower right) can be determined to be a candidate gene to be used. Candidate genes whose expressions are about 10 times or more induced when G12/13 is specifically activated in HeLa cells were only 10 genes (out of approximately 22,000 genes) by a genome-wide expression analysis.
Figure 15:
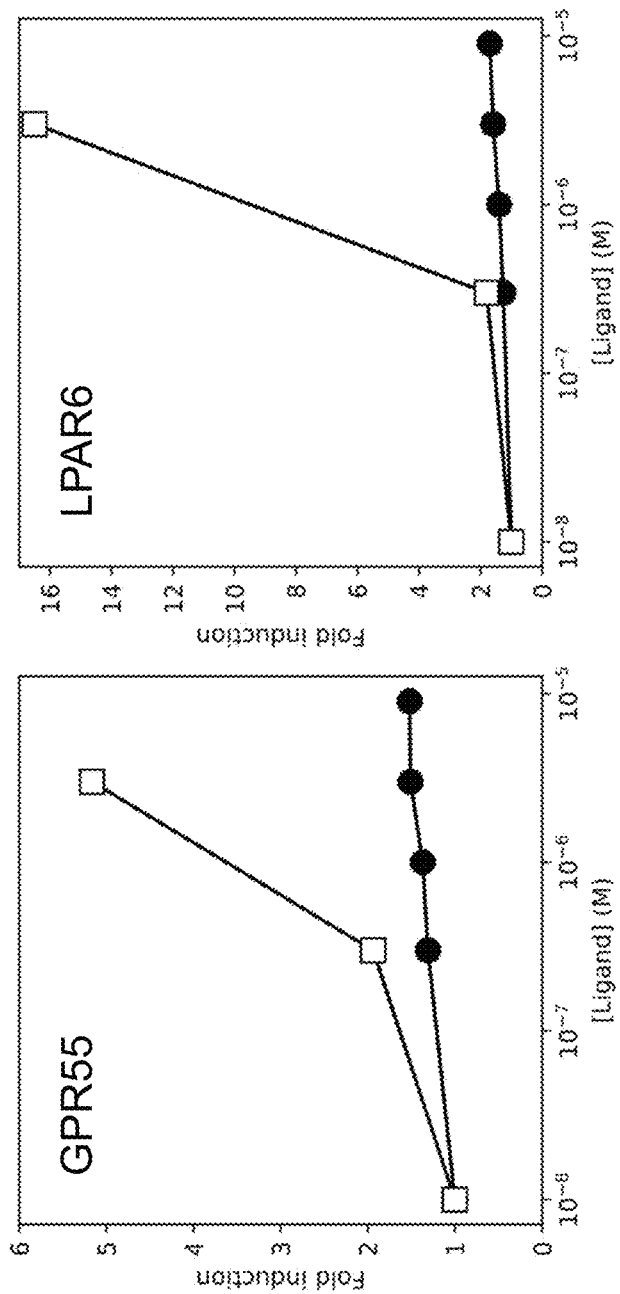
FIG. 15 is a figure showing that activation of G12/13-coupled GPCRs (GPR55 and LPAR6) by ligands was detected by the assay system of the present invention established using HEK293T cells. The horizontal axis indicates a ligand concentration, and the vertical axis indicates the luminescence intensity output in each assay system.
Figure 16:
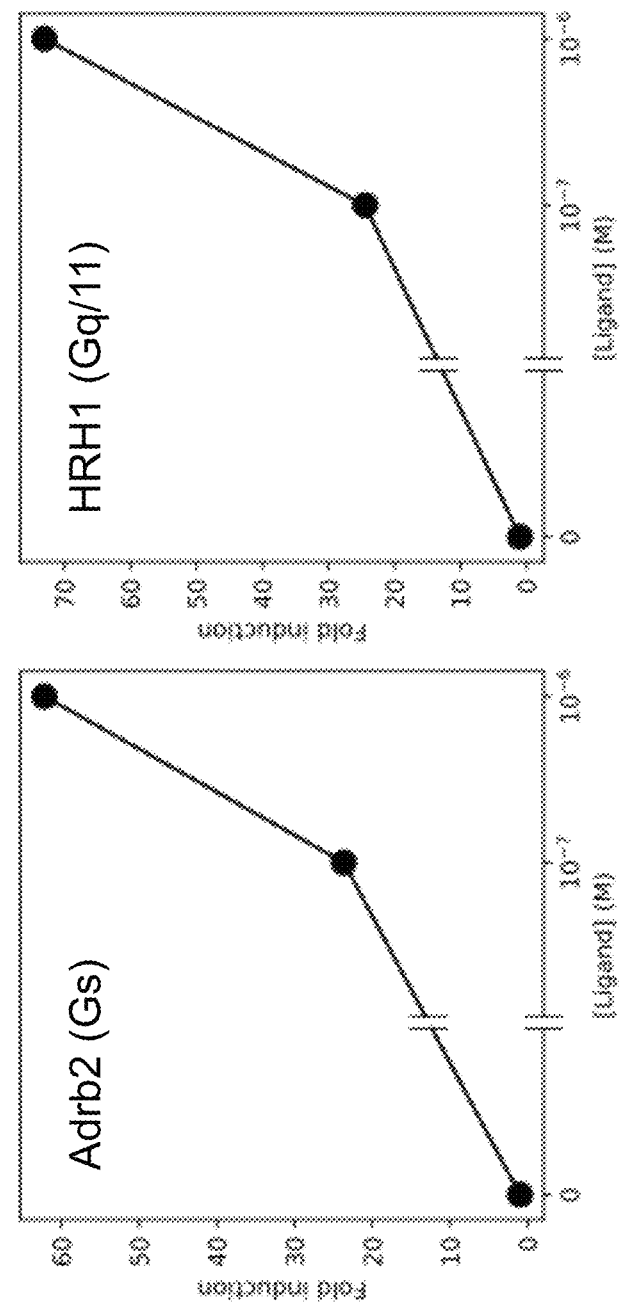
FIG. 16 is a figure showing that activation of a GPCR (Adrb2) coupled with a Gs G protein by a ligand and activation of a GPCR (HRH1) coupled with a Gq/11 G protein by a ligand were detected by the assay system of the present invention established using HEK293T cells.
Figure 17:
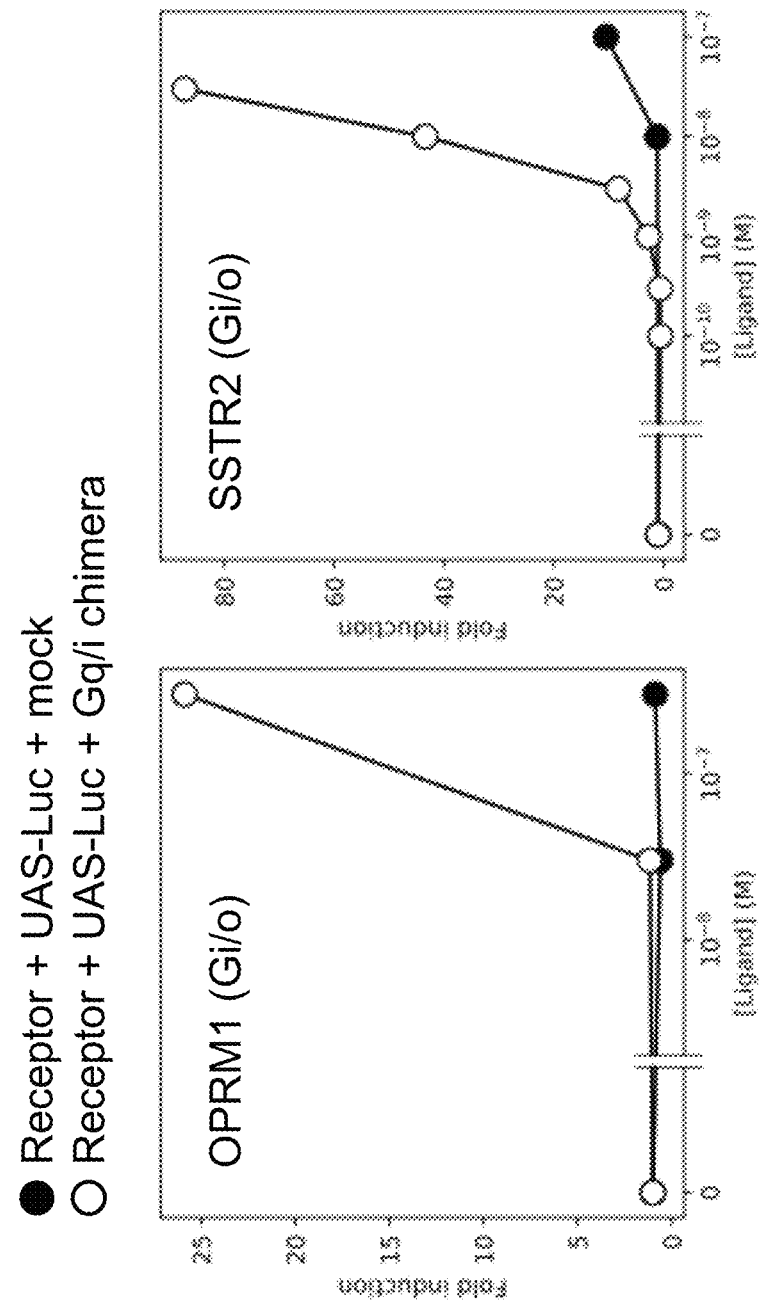
FIG. 17 is a figure showing that activation of GPCRs (OPRM1 and SSTR2) coupled with Gi/o G proteins was detected by the combined use of Gq/i1 and Gq/i3 chimeric proteins in the assay system of the present invention established using HEK293T cells.
Figure 18:
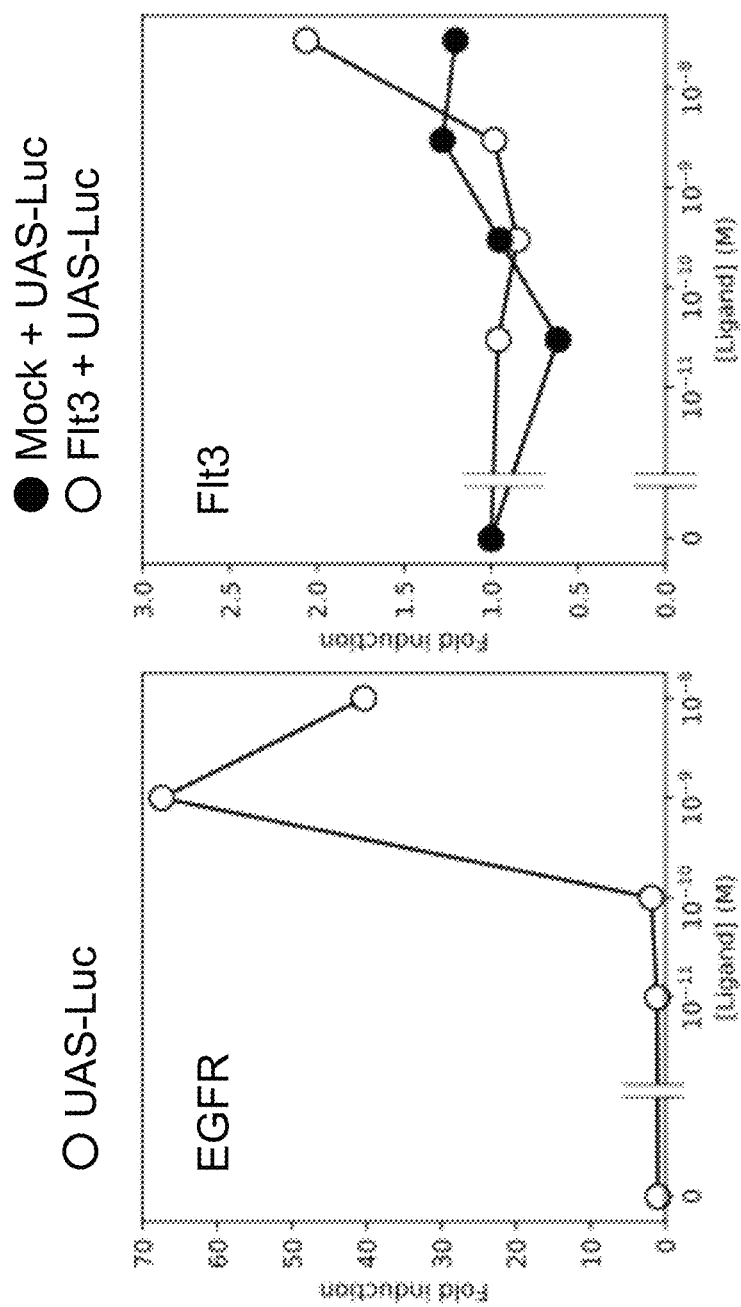
FIG. 18 is a figure showing that activation of receptor tyrosine kinases (Flt3 and EGFR) by ligands was detected by the assay system of the present invention established using HEK293T cells.

Taking the above-described "Condition 7" as an example, the experimental procedures are described below (see FIG. 14).

Day 1: HeLa cells were seeded on a 6-cm tissue culture dish ($5 \times 10^5$ cells per dish).

Day 2: An LPAR6 expression plasmid (2 μg) was transfected into the HeLa cells according to a lipofection method.

Day 3: After 24 hours had been passed after the gene transfection, the cells were stimulated by 10 μM LPA for 1 hour. Immediately after the stimulation, total RNA was recovered from the cells.

The experiments were each carried out under individual conditions in triplicates. Accordingly, the number of samples was a total of 21 samples (7×3=21).

The 21 total RNA samples recovered by the above-described experimental procedures were subjected to RNA seq analysis using a next-generation sequencer.

Experiment (1): Comparison made among four groups of Conditions 1, 2, 3 and 4

Experiment (2): Comparison made among four groups of Conditions 1, 5, 6 and 7

In Experiment (1), genes whose expression levels were significantly increased only under "Condition 4" were listed up. In Experiment (2), genes whose expression levels were significantly increased only under "Condition 7" were listed up.

The RNA seq analysis was outsourced to GeneWiz (Japan). The next-generation sequencer used in sequencing was Illumina HiSeq 4000, and the sequencing was carried out at 150 PE. As a result, 20 to 26 million PE reads (6 to 8 GB) were obtained per sample.

TruSeq Stranded mRNA Library Prep Kit (Illumina) was used for preparation of a library. Regarding the sequencing data, adaptor sequences were removed by Cutadapt (http://cutadapt.readthedocs.io/en/stable/), and 3'-termini having low-quality bases (Phred quality score <20) were trimmed by Trimmomatic (https://github.com/timflutre/trimmomatic). Subsequently, it was confirmed that all samples had a total read count $>2 \times 10^7$. Reads were aligned to the mm9 reference sequence using STAR ver. 2.5.2b (https://github.com/alexdobin/STAR). Samples having a unique mapping rate >90% could be used for the subsequent analyses. Quantification of gene expression and differential expression analysis were performed using the Cufflinks package ver. 2.2.1 (http://cole-trapnell-lab.github.io/cufflinks).

[Results]

Genes listed up in both of the two experiments were considered to be a group of genes of interest.

The group of genes is shown in the following Table 5.

TABLE 5

| Gene_ID | FPKM | fold induction |
| --- | --- | --- |
| ARC | 0.38 | 13.2 |
| CCL20 | 0.13 | 36.6 |
| CTGF | 11.49 | 26.1 |
| DUSP5 | 16 | 14.1 |
| EGR1 | 4.79 | 10.2 |
| EGR2 | 0.12 | 34.8 |
| EGR3 | 0.04 | 65.1 |
| FOSB | 3.46 | 18.6 |
| NR4A1 | 68.03 | 23.1 |
| NR4A3 | 8.92 | 14.7 |

Furthermore, other than the aforementioned genes, expression fluctuation was observed in the following genes:

THBS1, AREG, SLFNL1, SLFNL1-AS1, CDH5, NR4A2, CYR61, and CRISPLD2 (having an expression fluctuation of 10 times or more, at least, in any experiment);

FOSL1, TNFAIP3, EPPK1, NUAK2, CXCL2, KDM6B, PHLDA1, CSRNP1, TAGLN, PTGER4, JUN, ATF3, NCOA7, ADAMTS1, EDN1, ZC3H12C, PTGS2, DCUN1D3, ITPRIP, JUNB, SDC4, ERRFI1, SRF, MYADM, MMP12, MAFF, RCAN1, F3, IL6, LDLR,

KRT34, EDN2, GADD45A, KRT17, TUFT1, MN1, DUSP4, KLF6, REL, ABL2, CITED2, MAFK, RND3, KLF2, TRIB1, and PHLDB2 (having an expression fluctuation of 5 times or more in all experiments);

RASD1, SOWAHC, DUSP8, OTUD1, ARL5B, ETV3, ZFP36, NAV2, ITGB8, SERPINE1, NOCT, ZBTB10, BMP2, TRAF1, EPHA2, IER2, TNS4, ELMSAN1, ADAMTS5, TSC22D2, ZNF281, BCL10, RNF217, BTG2, ELL2, KIAA1217, GPCPD1, NAB2, MCL1, TIPARP, EPGN, RIMKLB, IER5, C8orf4, ADM, KRT16, NFKBID, ZNF331, SERTAD1, PSD4, and DAPP1 (having an expression fluctuation of 5 times or more in any experiment); and WEE1, TBX3, PMAIP1, ARID5B, BACH1, ZFP36L2, VGLL3, GATA6, AKAP2, PLAUR, TICAM1, JAG1, SLC7A11, FOXC2, HBEGF, GPRC5A, KCNJ12, STARD4, YOD1, RHOB, IRS2, SLC30A7, C19orf71, PPP1R15B, USP36, BHLHE40, LIFR, STK38L, LOC100129550, RUNX1, CEBPD, KLF7, KLF5, LATS2, HECA, PPP1R3B, GADD45B, BIRC3, NT5DC3, ATXN7, ZNF644, FOSL2, PER2, MAP3K14, NABP1, FGF2, NFKBIA, JUND, RC3H1, RUSC2, DUSP16, ELF3, NEDD9, FAM86B3P, CREM, IQCJ-SCHIP1, HK2, ZNF548, ZNF217, PER1, AHR, SLC2A13, PDP1, HRH1, PFKFB3, TPPP, JPH2, CPEB4, MB21D2, HLA-H, SLC38A2, FRMD4B, PTPRH, SSC5D, PLEKHO2, EGLN1, FOXC1, PDE4D, CPEB3, ZSWIM4, TGFBR1, PRG2, CCDC68, IER3, FBLIM1, RASSF8, USP2, PPTC7, CDC42EP2, ZFAND5, SGK1, TNFRSF8, LYPD3, CITED4, MYH9, SIK1, SGMS2, ZC3H12A, DUSP1, IRF2BPL, ZFP36L1, EPAS1, TMEM160, NCEH1, KLF9, TMEM158, NAB1, RNF19A, KCNK1, PRDM1, IRF2BP2, CHD1, MXD1, KIAA0355, ELL, PIGA, CNN2, ABHD13, MESDC1, SCML1, TGFBR3, DDAH1, ANKRD33B, MAP3K8, MAP2K3, SOCS6, MPZL3, UGCG, AEN, CDKN1A, C9orf72, CHD2, RNF19B, VCL, MFSD2A, RELT, HELZ2, ZNF529, ADAP1, RP2, FBXO46, ETS2, ANKRD1, NFKBIE, SH3RF1, SFMBT2, AEBP2, ZYX, HES4, CBX4, GLI2, SNRK, MTCL1, MITF, ARHGAP28, ELAVL2, PMP22, SOCS3, MALAT1, WDR37, SLC2A3, COQ10B, CCNL1, PXDC1, SLC26A2, PIM1, FAM60A, OLR1, STX11, ZBTB21, SPRED2, CTTNBP2NL, CCNT1, ZNF324, UBALD1, LIMA1, ACTG1, SLC19A2, PRRG1, TLE4, ICAM1, IFFO2, PLEKHG3, ARHGAP23, GAB2, NYAP2, DKK1, NT5E, DENND3, USP53, CD83, MC1R, PANX1, SLC20A1, KLF4, TNFRSF10A, SIRT1, DNAJB4, STEAP4, PHLDA3, FAT4, C1QTNF1, AP1AR, KRT80, ZC3HAV1, SAV1, ACKR3, TP53I11, CMIP, RGS2, CDKN2AIP, Adrb2, TSC22D1, TM4SF1, FBXO33, CSRP1, BMPR1B, RELB, NTN4, ATP2B1, CDC42SE1, ALDH1B1, TRMT44, ROR1, VPS37B, TRAF4, PPP2R3A, HSPA2, DAAM1, LINC00657, CASZ1, DAW1, ALPK2, GRAMD3, RAB20, MAMDC2, SAMD4A, RASAL2, WWC2, RAP1GAP2, DNAJC6, PPP1R3C, TPM4, KIAA0825, WDR1, NFKB2, FSTL3, ARHGAP32, NFIL3, ZNF267, HMGCS1, FHL2, TPM1, KLHL29, CRB1, SLC25A16, MFAP5, FHL1, MMP24, RAB32, 1L32, and ARHGDIB (having an expression fluctuation of 2 to 5 times in all experiments).

These genes can also be used as "genes whose expressions are induced" in the methods described in the present description.

[Consideration]

It was demonstrated that a gene group whose expression is induced by the activation of a specific protein can be identified by the aforementioned procedures. Using such a gene group, the reporter system involving the connection of a plurality of factors described in the present description can be constructed.

HeLa cells were used in Examples A and B. However, in the case of using cells generating different expression regulation by the activation of a protein, it is possible to identify a gene group whose expression is induced and to construct an assay system by applying the procedures of the present invention.

In fact, as described in Example E later, a similar reporter assay system was successfully established using HEK293T cells by applying the procedures of the present example.

Example D1: Cell Array

Following the procedures described in the aforementioned Example A and B, there are provided a plurality of cells each overexpressing a plurality of different receptors. In an array having a plurality of wells, individual cells are maintained in each well. A test compound is applied onto the array, so that a comprehensive investigation of the action of the test compound on the plurality of receptors can be simply carried out.

GPCRs can be used as receptors. Using the cells described in Examples A and B, the action of the test compound on all of Gs-coupled GPCRs, Gq-coupled GPCRs, Gi-coupled GPCRs and G12/13-coupled GPCRs can be simultaneously investigated with cells having the same configuration for portions other than the receptor.

Example D2: Construct

Using the sequences of the transcriptional regulatory regions of first to Nth genes whose expressions are induced by the activation of a certain membrane protein, first to Nth constructs each comprising the sequences of the transcriptional regulatory regions of the first to Nth genes are provided. Each construct comprises a sequence encoding a specific factor in a state in which the coding sequence is operably linked to the transcriptional regulatory region. Each factor promotes the activation of other factors. Each construct may be present on a series of nucleic acid molecules, or may also be present on different nucleic acid molecules.

The first to Nth constructs are provided in a kit for modifying cells to those used in the screening of a compound. The kit may include a construct for overexpressing a membrane protein. The kit may include a construct comprising a reporter gene configured so that the expression thereof is triggered by any of the factors.

Example D3: Analysis

Using the array of Example D1 including cells corresponding to all human GPCRs, the activity of a test compound on all of the human GPCRs (excluding odorant receptors) is investigated. From the reaction of each well on the array, the types of GPCRs on which the test compound exhibits its activity can be examined. Thereby, the types of human GPCRs on which the test compound has an off-target activity, or the types of human GPCRs on which the test compound does not have such an off-target activity, can be confirmed. Thereby, for example, a risk of suspending a clinical trial due to unexpected side effects that are generated after initiation of the clinical trial can be reduced. Moreover, also regarding compounds known to have a certain activity, the activity of the compound on all human GPCRs is evaluated, so that a novel activity of the compound can be identified.

Example D4: High-Throughput Screening by Single Cell Assay

Using a microchannel disk or another single cell assay system, a single cell is cultured in each chamber. A transfection reagent that comprises a large number of different receptors and has a moderately low concentration is prepared, and this transfection reagent is then applied at once to the cells in a large number of chambers. By doing so, the subsets of a receptor group comprised in the reagent can be transfected into individual cells (assuming that the reagent comprises 100 types of receptor plasmids, it is assumed that several receptor plasmids thereof can be transfected into each cell). Since the concentration of the receptor plasmid in the reagent is low, the receptor to be transfected into each cell is determined stochastically. At last, a single compound or a mixture of multiple compounds is applied at once to cells in a plurality of chambers. Also, an operation to wash and apply another compound may be repeated. By performing single-cell PCR on the cells in the chamber exhibiting reactivity, receptor candidates responding to the compound can be efficiently narrowed down.

Example D5: Searching for Compounds that Give Stress to Cells

It is anticipated that the knock-in reporter cells, NCP19 cells, described in the present description, cannot only detect signals triggered when various cell membrane receptors are stimulated by their corresponding ligands, but can also monitor a stress response when the cells themselves receive stress. Accordingly, the cell membrane receptors and the like are not exogenously transfected into the NCP19 cells, but a test compound is allowed to act on the NCP19 cells themselves, so that it can become an assay system capable of examining whether the compound induces a stress response to the cells.

Example D6: Searching for Oncogenes (or Oncogenic Mutants)

As shown in Examples A4 and A5, NCP19 cells that are knock-in reporter cells described in the present description can detect not only GPCRs but also intracellular signals (proliferation signals) generated when a receptor tyrosine kinase is activated by its ligand. It is anticipated from this fact that if a receptor tyrosine kinase mutant that is in a constitutively active state as a result of genetic mutation (such a receptor tyrosine kinase mutant functions as an oncogene in cells in many cases) is transiently and exogenously transfected in NCP19, reporter activity in the NCP19 cells shows a high value in a ligand stimulation independent manner. Therefore, if various cancer gene candidate mutants are transiently introduced into NCP19 cells, and reporter activity provoked by each of those mutants is examined, it becomes possible to verify a candidate mutant molecule having a stronger cell proliferating activity by one step.

Example D7: Bitter Taste Receptors

Following the procedures described in Examples A and B, a plurality of cells each overexpressing a plurality of bitter taste receptors are provided. In an array having a plurality of wells, individual cells are maintained in each well. A test compound is applied onto the array, so that a comprehensive investigation of the action of the test compound on bitter taste receptors can be simply carried out.

Example D8: Orphan Receptors

Following the procedures described in Examples A and B, cells overexpressing receptors whose ligands are unknown are provided. In an array having a plurality of wells, cells are maintained in each well. A plurality of test compounds are applied onto the array, so that a comprehensive screening for a compound that activates an orphan receptor can be simply carried out.

Example E: Construction of Assay System Using Different Cells

[Overview]

The present example is intended to demonstrate that the assay system of the present invention can be constructed using a cell line other than HeLa cells, and that a test compound can be screened using the present assay system.

[Materials and Methods]

(Identification of Expression Fluctuating Gene)

In HEK293T cells, the experiments are performed using GPCRs (GPR55 or LPAR6) that specifically activate the G protein G12/13 and substances that have already been known to function as a ligand of the GPCRs.

Condition 1 HEK293T cells (wild type)
Condition 2 HEK293T cells (wild type)+mock+10 μM ligand: stimulation for 1 hour
Condition 3 HEK293T cells (wild type)+GPCR+vehicle: stimulation for 1 hour
Condition 4 HEK293T cells (wild type)+GPCR+10 μM ligand: stimulation for 1 hour Following the conditions described in Example C, total RNA samples were recovered, and were then subjected to RNA seq analysis using a next-generation sequencer. Genes whose expression levels were significantly increased only under Condition 4 were listed up.

The listed genes were set to be a gene group of interest. The gene group is shown in the following Table 6.

TABLE 6

| gene_id | FPKM | fold induction |
|---------|------|----------------|
| CTGF    | 0.53 | 17.3           |
| CYR61   | 3.37 | 19             |
| DUSP5   | 0.89 | 10.5           |
| EGR1    | 2.81 | 51.7           |
| EGR2    | 0.25 | 15.3           |
| EGR3    | 0.19 | 55.9           |
| FOS     | 1.31 | 40.7           |
| FOSB    | 0.98 | 22.9           |
| NR4A3   | 0.4  | 10.6           |

Furthermore, other than the aforementioned genes, expression fluctuation was observed in the following genes:
NR4A2, LOC100506747, NR4A1, EPPK1, JUN, AMOTL2, FLNA, ARC, IER2, and JUNB (having an expression fluctuation of 5 times or more, at least, in any experiment); and
CNN2, DUSP1, MAFF, GPR3, TPM1, PTGS2, ATF3, GOS2, TRIB1, SNAI2, PDLIM7, NFKBIZ, TIMP3, FHL2, SPRY2, FOSL2, FERMT2, VCL, NUPR1, TPM4, GRASP, NKX2-5, TUFT1, ID1, FOSL1, MYADM, ACTB, LPP, KLF7, KLF6, ADAMTS1, BTG2, ACTG1, CSRNP1, WDR1, SRF, GEM, ZYX, NR2F1, LOC101928358, ITPRIP, FUT1, COL3A1, LIMA1, SLC8A1, JAG1, SLC6A9, PMAIP1, SLC2A10, PCK2, ZFP36L1, MAFB, CBX4, FZD10, ZBTB10, JDP2, ZNF214, RHOB, ID2, RND3, IRF2BPL, BMP2, SOX4, JUND, SLC1A4, PNRC1, and SYBU (having an expression fluctuation of 2 times or more, at least, in any experiment).

(Construction of Indicator Cells)

From the listed genes, FOS was selected as gene #1 and FOSB was selected as gene #2.

According to the procedures described in Example A3, TMGV and TM3C were knocked-in into the 3'-UTR of the gene loci of FOS and FOSB of HEK293T cells.

(Confirmation of Assay Performance)

A GPCR expression plasmid and a UAS-reporter gene plasmid were introduced into the above-described cells, and the cells were then stimulated by the GPCR ligands. As GPCRs, the receptors, GPR55 (G12/13-coupled GPCR), LPAR6 (G12/13-coupled GPCR), Adrb2 (Gs-coupled GPCR), HRH1 (Gq-coupled GPCR), and OPRM1 (Gi/o-coupled GPCR) and SSTR2 (Gi/o-coupled GPCR), were used. Moreover, using the above-described cells, activation of receptor tyrosine kinases (Flt3 and EGFR) was also measured.

[Results]

Signals (luminescent intensity and magnification of change from signals when the ligand had the lowest concentration) obtained from each assay system as a result of addition of various concentrations of ligands are shown in FIG. 15 to FIG. 18. As in the case of the indicator cells produced with HeLa cells, also in indicator cells produced with HEK293T cells, an increase in the signals along with an increase in the ligand concentration was observed in each of the tested receptors.

[Consideration]

From the results of the present example, it was demonstrated that the indicator cells of the present invention can be produced by the method of Example A3, regardless of the type of a cell line used.

Example F: Construction of Assay System Using Different Factors

In cells, a first factor and a second factor are knocked-in into the gene loci of gene #1 and gene #2 whose expressions are induced by the activation of the G protein G12/13.

For example, a transcription factor whose transcriptional activity is turned on by being phosphorylated can be used as a first factor, and a phosphorylation enzyme that phosphorylates the first factor can be used as a second factor.

Alternatively, an artificial inactive-type transcription factor can be used as a first factor, and a protease can be used as a second factor. A partial structure is removed from the artificial inactive-type transcription factor by the protease, and nuclear localization signals existing in the transcription factor are thereby exposed onto the surface, so that the inactive-type transcription factor can be converted to an active-type transcription factor capable of translocating into the nucleus. Otherwise, a partial structure is removed from the artificial inactive-type transcription factor by the protease, and a DNA-binding domain or a transcription activation domain existing in the transcription factor thereby becomes operable, so that the inactive-type transcription factor can be converted to an active-type transcription factor.

(Notes)

As described above, the present invention has been exemplified using the preferred embodiments of the present invention. However, the above description and examples are provided for illustrative purposes only, and are not provided for the purpose of limiting the present invention. Therefore, it is understood that the present invention is not limited to the embodiments or examples specifically described herein, and that the scope of the present invention should be construed only by the claims. Patents, patent applications and publications cited herein should be incorporated by reference in their entireties, as with the content itself that is specifically described herein.

INDUSTRIAL APPLICABILITY

The assay system of the present invention can be utilized in the screening of a compound having physiological activity. The present invention cannot only provide a sensitive assay system for G12/13-coupled GPCRs with improved sensitivity and S/N (one or more orders of magnitude), but can also monitor "Gs-coupled GPCRs," "Gq-coupled GPCRs," and "Gi-coupled GPCRs" under a single assay format. In addition, the present assay system has versatility with which it can be applied to receptor groups and channel groups other than GPCRs. According to the present invention, in the use of a compound having physiological activity in pharmaceutical products and the like, the present assay system can be utilized not only in on-target screening of a compound having physiological activity, but also in off-target screening that predicts in an early stage (before clinical trials) side effects caused by a test compound that activates an unexpected receptor.

Sequence Listing Free Text

SEQ ID NO: 1: HRV protease 3C recognition cleavage sequence
SEQ ID NO: 2: Linker sequence in TMGV
SEQ ID NO: 3: GS linker sequence
SEQ ID NO: 4: Human G12 amino acid sequence
SEQ ID NO: 5: Human Gs amino acid sequence
SEQ ID NO: 6: G12/s chimera amino acid sequence
SEQ ID NO: 7: human Gi1 amino acid sequence
SEQ ID NO: 8: G12/i1 chimeric amino acid sequence

The invention claimed is:

1. A combination of constructs for investigating the action of a test compound on a protein responsible for signal transduction,
wherein the combination of constructs comprises n sequential constructs for a sequential enzyme reaction cascade and one reporter gene construct,
wherein
the n constructs for a sequential enzyme reaction cascade comprises one nucleotide sequence encoding a substrate operably linked to the transcriptional regulatory region of a gene (gene 1) and n−1 nucleotide sequences, wherein the each one of the n−1 nucleotide sequences encodes a different enzyme operably linked to the transcriptional regulatory region of a different gene out of n genes other than gene 1, respectively,
the expressions of n genes, whose transcriptional regulatory regions are used in n sequential constructs for a sequential enzyme reaction cascade, are induced by activation of the protein,
the reporter gene construct is configured to activate the reporter gene by the final product of the sequential enzyme reaction cascade,
n is an integer of 3 or more, and
the combination includes:
(1) a first construct in which the transcriptional regulatory region of a first gene (gene 1) is linked to a nucleotide sequence encoding a substrate(S) for an enzyme reaction;
(2) a second construct in which the transcriptional regulatory region of a second gene (gene 2) is linked to a nucleotide sequence encoding an enzyme (E1) for an enzyme reaction, wherein a product P1 is generated as a result of the enzyme reaction between S and E1
(3) n−2 sequential construct(s): each construct encodes an enzyme, which generates a product by catalyzing the previous product generated by the previous enzyme reaction mediated by the previous enzyme encoded in the previous construct, is operably linked to the transcriptional regulatory regions of a gene out of n genes other than previously used genes, and
(4) a reporter gene construct that is configured so that a reporter gene is activated by a final product of a sequential enzyme reaction cascade, wherein the expressions of n genes, whose transcriptional regulatory regions are used in n constructs for a sequential enzyme reaction cascade, are induced by stimulation of the protein by the test compound.

2. A cell comprising the combination of constructs according to claim 1.

3. The combination of constructs according to claim 1, wherein n=3.

4. The cell according to claim 2, wherein n=3.

5. The cell according to claim 4, wherein the cell is a HeLa cell.

* * * * *

SEQUENCE LISTING

<160> NUMBER OF SEQ ID NOS: 8

<210> SEQ ID NO 1
<211> LENGTH: 8
<212> TYPE: PRT
<213> ORGANISM: Artificial
<220> FEATURE:
<223> OTHER INFORMATION: HRV3C recognition sequence

```
<400> SEQUENCE: 1

Leu Glu Val Leu Phe Gln Gly Pro
1               5

<210> SEQ ID NO 2
<211> LENGTH: 16
<212> TYPE: PRT
<213> ORGANISM: Artificial
<220> FEATURE:
<223> OTHER INFORMATION: TMGV(Transmembrane-Gal4VP64) linker sequence

<400> SEQUENCE: 2

Gly Ser Ser Ser Leu Glu Val Leu Phe Gln Gly Pro Gly Ser Ser Ser
1               5                   10                  15

<210> SEQ ID NO 3
<211> LENGTH: 15
<212> TYPE: PRT
<213> ORGANISM: Artificial
<220> FEATURE:
<223> OTHER INFORMATION: GS linker sequence

<400> SEQUENCE: 3

Gly Gly Gly Gly Ser Gly Gly Gly Gly Ser Gly Gly Gly Gly Ser
1               5                   10                  15

<210> SEQ ID NO 4
<211> LENGTH: 381
<212> TYPE: PRT
<213> ORGANISM: Homo sapiens

<400> SEQUENCE: 4

Met Ser Gly Val Val Arg Thr Leu Ser Arg Cys Leu Leu Pro Ala Glu
1               5                   10                  15

Ala Gly Gly Ala Arg Glu Arg Arg Ala Gly Ser Gly Ala Arg Asp Ala
                20                  25                  30

Glu Arg Glu Ala Arg Arg Arg Ser Arg Asp Ile Asp Ala Leu Leu Ala
            35                  40                  45

Arg Glu Arg Arg Ala Val Arg Arg Leu Val Lys Ile Leu Leu Leu Gly
        50                  55                  60

Ala Gly Glu Ser Gly Lys Ser Thr Phe Leu Lys Gln Met Arg Ile Ile
65                  70                  75                  80

His Gly Arg Glu Phe Asp Gln Lys Ala Leu Leu Glu Phe Arg Asp Thr
                85                  90                  95

Ile Phe Asp Asn Ile Leu Lys Gly Ser Arg Val Leu Val Asp Ala Arg
            100                 105                 110

Asp Lys Leu Gly Ile Pro Trp Gln Tyr Ser Glu Asn Glu Lys His Gly
        115                 120                 125

Met Phe Leu Met Ala Phe Glu Asn Lys Ala Gly Leu Pro Val Glu Pro
    130                 135                 140

Ala Thr Phe Gln Leu Tyr Val Pro Ala Leu Ser Ala Leu Trp Arg Asp
145                 150                 155                 160

Ser Gly Ile Arg Glu Ala Phe Ser Arg Ser Glu Phe Gln Leu Gly
                165                 170                 175

Glu Ser Val Lys Tyr Phe Leu Asp Asn Leu Asp Arg Ile Gly Gln Leu
            180                 185                 190

Asn Tyr Phe Pro Ser Lys Gln Asp Ile Leu Leu Ala Arg Lys Ala Thr
        195                 200                 205

Lys Gly Ile Val Glu His Asp Phe Val Ile Lys Lys Ile Pro Phe Lys
```

```
            210                 215                 220
Met Val Asp Val Gly Gly Gln Arg Ser Gln Arg Gln Lys Trp Phe Gln
225                 230                 235                 240

Cys Phe Asp Gly Ile Thr Ser Ile Leu Phe Met Val Ser Ser Ser Glu
            245                 250                 255

Tyr Asp Gln Val Leu Met Glu Asp Arg Thr Asn Arg Leu Val Glu
                260                 265                 270

Ser Met Asn Ile Phe Glu Thr Ile Val Asn Asn Lys Leu Phe Phe Asn
        275                 280                 285

Val Ser Ile Ile Leu Phe Leu Asn Lys Met Asp Leu Leu Val Glu Lys
    290                 295                 300

Val Lys Thr Val Ser Ile Lys Lys His Phe Pro Asp Phe Arg Gly Asp
305                 310                 315                 320

Pro His Arg Leu Glu Asp Val Gln Arg Tyr Leu Val Gln Cys Phe Asp
                325                 330                 335

Arg Lys Arg Arg Asn Arg Ser Lys Pro Leu Phe His His Phe Thr Thr
                340                 345                 350

Ala Ile Asp Thr Glu Asn Val Arg Phe Val Phe His Ala Val Lys Asp
            355                 360                 365

Thr Ile Leu Gln Glu Asn Leu Lys Asp Ile Met Leu Gln
    370                 375                 380

<210> SEQ ID NO 5
<211> LENGTH: 394
<212> TYPE: PRT
<213> ORGANISM: Homo sapiens

<400> SEQUENCE: 5

Met Gly Cys Leu Gly Asn Ser Lys Thr Glu Asp Gln Arg Asn Glu Glu
1               5                   10                  15

Lys Ala Gln Arg Glu Ala Asn Lys Lys Ile Glu Lys Gln Leu Gln Lys
            20                  25                  30

Asp Lys Gln Val Tyr Arg Ala Thr His Arg Leu Leu Leu Leu Gly Ala
        35                  40                  45

Gly Glu Ser Gly Lys Ser Thr Ile Val Lys Gln Met Arg Ile Leu His
    50                  55                  60

Val Asn Gly Phe Asn Gly Glu Gly Gly Glu Glu Asp Pro Gln Ala Ala
65                  70                  75                  80

Arg Ser Asn Ser Asp Gly Glu Lys Ala Thr Lys Val Gln Asp Ile Lys
                85                  90                  95

Asn Asn Leu Lys Glu Ala Ile Glu Thr Ile Val Ala Ala Met Ser Asn
            100                 105                 110

Leu Val Pro Pro Val Glu Leu Ala Asn Pro Glu Asn Gln Phe Arg Val
        115                 120                 125

Asp Tyr Ile Leu Ser Val Met Asn Val Pro Asp Phe Asp Phe Pro Pro
    130                 135                 140

Glu Phe Tyr Glu His Ala Lys Ala Leu Trp Glu Asp Glu Gly Val Arg
145                 150                 155                 160

Ala Cys Tyr Glu Arg Ser Asn Glu Tyr Gln Leu Ile Asp Cys Ala Gln
                165                 170                 175

Tyr Phe Leu Asp Lys Ile Asp Val Ile Lys Gln Ala Asp Tyr Val Pro
            180                 185                 190

Ser Asp Gln Asp Leu Leu Arg Cys Arg Val Leu Thr Ser Gly Ile Phe
        195                 200                 205
```

```
Glu Thr Lys Phe Gln Val Asp Lys Val Asn Phe His Met Phe Asp Val
    210                 215                 220
Gly Gly Gln Arg Asp Glu Arg Arg Lys Trp Ile Gln Cys Phe Asn Asp
225                 230                 235                 240
Val Thr Ala Ile Ile Phe Val Val Ala Ser Ser Ser Tyr Asn Met Val
                245                 250                 255
Ile Arg Glu Asp Asn Gln Thr Asn Arg Leu Gln Glu Ala Leu Asn Leu
            260                 265                 270
Phe Lys Ser Ile Trp Asn Asn Arg Trp Leu Arg Thr Ile Ser Val Ile
        275                 280                 285
Leu Phe Leu Asn Lys Gln Asp Leu Leu Ala Glu Lys Val Leu Ala Gly
    290                 295                 300
Lys Ser Lys Ile Glu Asp Tyr Phe Pro Glu Phe Ala Arg Tyr Thr Thr
305                 310                 315                 320
Pro Glu Asp Ala Thr Pro Glu Pro Gly Glu Asp Pro Arg Val Thr Arg
                325                 330                 335
Ala Lys Tyr Phe Ile Arg Asp Glu Phe Leu Arg Ile Ser Thr Ala Ser
            340                 345                 350
Gly Asp Gly Arg His Tyr Cys Tyr Pro His Phe Thr Cys Ala Val Asp
        355                 360                 365
Thr Glu Asn Ile Arg Arg Val Phe Asn Asp Cys Arg Asp Ile Ile Gln
    370                 375                 380
Arg Met His Leu Arg Gln Tyr Glu Leu Leu
385                 390

<210> SEQ ID NO 6
<211> LENGTH: 381
<212> TYPE: PRT
<213> ORGANISM: Artificial
<220> FEATURE:
<223> OTHER INFORMATION: G12/s chimera amino acid sequence

<400> SEQUENCE: 6

Met Ser Gly Val Val Arg Thr Leu Ser Arg Cys Leu Leu Pro Ala Glu
1               5                   10                  15
Ala Gly Gly Ala Arg Glu Arg Arg Ala Gly Ser Gly Ala Arg Asp Ala
                20                  25                  30
Glu Arg Glu Ala Arg Arg Ser Arg Asp Ile Asp Ala Leu Leu Ala
            35                  40                  45
Arg Glu Arg Arg Ala Val Arg Arg Leu Val Lys Ile Leu Leu Leu Gly
    50                  55                  60
Ala Gly Glu Ser Gly Lys Ser Thr Phe Leu Lys Gln Met Arg Ile Ile
65                  70                  75                  80
His Gly Arg Glu Phe Asp Gln Lys Ala Leu Leu Glu Phe Arg Asp Thr
                85                  90                  95
Ile Phe Asp Asn Ile Leu Lys Gly Ser Arg Val Leu Val Asp Ala Arg
            100                 105                 110
Asp Lys Leu Gly Ile Pro Trp Gln Tyr Ser Glu Asn Glu Lys His Gly
        115                 120                 125
Met Phe Leu Met Ala Phe Glu Asn Lys Ala Gly Leu Pro Val Glu Pro
    130                 135                 140
Ala Thr Phe Gln Leu Tyr Val Pro Ala Leu Ser Ala Leu Trp Arg Asp
145                 150                 155                 160
Ser Gly Ile Arg Glu Ala Phe Ser Arg Arg Ser Glu Phe Gln Leu Gly
                165                 170                 175
```

```
Glu Ser Val Lys Tyr Phe Leu Asp Asn Leu Asp Arg Ile Gly Gln Leu
            180                 185                 190

Asn Tyr Phe Pro Ser Lys Gln Asp Ile Leu Leu Ala Arg Lys Ala Thr
            195                 200                 205

Lys Gly Ile Val Glu His Asp Phe Val Ile Lys Lys Ile Pro Phe Lys
            210                 215                 220

Met Val Asp Val Gly Gly Gln Arg Ser Gln Arg Gln Lys Trp Phe Gln
225                 230                 235                 240

Cys Phe Asp Gly Ile Thr Ser Ile Leu Phe Met Val Ser Ser Ser Glu
            245                 250                 255

Tyr Asp Gln Val Leu Met Glu Asp Arg Arg Thr Asn Arg Leu Val Glu
            260                 265                 270

Ser Met Asn Ile Phe Glu Thr Ile Val Asn Asn Lys Leu Phe Phe Asn
            275                 280                 285

Val Ser Ile Ile Leu Phe Leu Asn Lys Met Asp Leu Leu Val Glu Lys
            290                 295                 300

Val Lys Thr Val Ser Ile Lys Lys His Phe Pro Asp Phe Arg Gly Asp
305                 310                 315                 320

Pro His Arg Leu Glu Asp Val Gln Arg Tyr Leu Val Gln Cys Phe Asp
            325                 330                 335

Arg Lys Arg Arg Asn Arg Ser Lys Pro Leu Phe His His Phe Thr Thr
            340                 345                 350

Ala Ile Asp Thr Glu Asn Val Arg Phe Val Phe His Ala Val Lys Asp
            355                 360                 365

Thr Ile Leu Gln Glu Asn Leu Arg Gln Tyr Glu Leu Leu
            370                 375                 380

<210> SEQ ID NO 7
<211> LENGTH: 354
<212> TYPE: PRT
<213> ORGANISM: Homo sapiens

<400> SEQUENCE: 7

Met Gly Cys Thr Leu Ser Ala Glu Asp Lys Ala Ala Val Glu Arg Ser
1               5                   10                  15

Lys Met Ile Asp Arg Asn Leu Arg Glu Asp Gly Glu Lys Ala Ala Arg
            20                  25                  30

Glu Val Lys Leu Leu Leu Leu Gly Ala Gly Glu Ser Gly Lys Ser Thr
            35                  40                  45

Ile Val Lys Gln Met Lys Ile Ile His Glu Ala Gly Tyr Ser Glu Glu
        50                  55                  60

Glu Cys Lys Gln Tyr Lys Ala Val Val Tyr Ser Asn Thr Ile Gln Ser
65                  70                  75                  80

Ile Ile Ala Ile Ile Arg Ala Met Gly Arg Leu Lys Ile Asp Phe Gly
            85                  90                  95

Asp Ser Ala Arg Ala Asp Asp Ala Arg Gln Leu Phe Val Leu Ala Gly
            100                 105                 110

Ala Ala Glu Glu Gly Phe Met Thr Ala Glu Leu Ala Gly Val Ile Lys
            115                 120                 125

Arg Leu Trp Lys Asp Ser Gly Val Gln Ala Cys Phe Asn Arg Ser Arg
            130                 135                 140

Glu Tyr Gln Leu Asn Asp Ser Ala Ala Tyr Tyr Leu Asn Asp Leu Asp
145                 150                 155                 160

Arg Ile Ala Gln Pro Asn Tyr Ile Pro Thr Gln Gln Asp Val Leu Arg
            165                 170                 175
```

```
Thr Arg Val Lys Thr Thr Gly Ile Val Glu Thr His Phe Thr Phe Lys
            180                 185                 190

Asp Leu His Phe Lys Met Phe Asp Val Gly Gly Gln Arg Ser Glu Arg
            195                 200                 205

Lys Lys Trp Ile His Cys Phe Glu Gly Val Thr Ala Ile Ile Phe Cys
        210                 215                 220

Val Ala Leu Ser Asp Tyr Asp Leu Val Leu Ala Glu Asp Glu Glu Met
225                 230                 235                 240

Asn Arg Met His Glu Ser Met Lys Leu Phe Asp Ser Ile Cys Asn Asn
                245                 250                 255

Lys Trp Phe Thr Asp Thr Ser Ile Ile Leu Phe Leu Asn Lys Lys Asp
            260                 265                 270

Leu Phe Glu Glu Lys Ile Lys Lys Ser Pro Leu Thr Ile Cys Tyr Pro
            275                 280                 285

Glu Tyr Ala Gly Ser Asn Thr Tyr Glu Glu Ala Ala Ala Tyr Ile Gln
            290                 295                 300

Cys Gln Phe Glu Asp Leu Asn Lys Arg Lys Asp Thr Lys Glu Ile Tyr
305                 310                 315                 320

Thr His Phe Thr Cys Ala Thr Asp Thr Lys Asn Val Gln Phe Val Phe
                325                 330                 335

Asp Ala Val Thr Asp Val Ile Ile Lys Asn Asn Leu Lys Asp Cys Gly
            340                 345                 350

Leu Phe

<210> SEQ ID NO 8
<211> LENGTH: 381
<212> TYPE: PRT
<213> ORGANISM: Artificial
<220> FEATURE:
<223> OTHER INFORMATION: G12/i1 chimera amino acid sequence

<400> SEQUENCE: 8

Met Ser Gly Val Val Arg Thr Leu Ser Arg Cys Leu Leu Pro Ala Glu
1               5                   10                  15

Ala Gly Gly Ala Arg Glu Arg Arg Ala Gly Ser Gly Ala Arg Asp Ala
            20                  25                  30

Glu Arg Glu Ala Arg Arg Ser Arg Asp Ile Asp Ala Leu Leu Ala
        35                  40                  45

Arg Glu Arg Arg Ala Val Arg Arg Leu Val Lys Ile Leu Leu Leu Gly
    50                  55                  60

Ala Gly Glu Ser Gly Lys Ser Thr Phe Leu Lys Gln Met Arg Ile Ile
65                  70                  75                  80

His Gly Arg Glu Phe Asp Gln Lys Ala Leu Leu Glu Phe Arg Asp Thr
                85                  90                  95

Ile Phe Asp Asn Ile Leu Lys Gly Ser Arg Val Leu Val Asp Ala Arg
            100                 105                 110

Asp Lys Leu Gly Ile Pro Trp Gln Tyr Ser Glu Asn Glu Lys His Gly
        115                 120                 125

Met Phe Leu Met Ala Phe Glu Asn Lys Ala Gly Leu Pro Val Glu Pro
    130                 135                 140

Ala Thr Phe Gln Leu Tyr Val Pro Ala Leu Ser Ala Leu Trp Arg Asp
145                 150                 155                 160

Ser Gly Ile Arg Glu Ala Phe Ser Arg Arg Ser Glu Phe Gln Leu Gly
                165                 170                 175
```

-continued

```
Glu Ser Val Lys Tyr Phe Leu Asp Asn Leu Asp Arg Ile Gly Gln Leu
            180                 185                 190

Asn Tyr Phe Pro Ser Lys Gln Asp Ile Leu Leu Ala Arg Lys Ala Thr
        195                 200                 205

Lys Gly Ile Val Glu His Asp Phe Val Ile Lys Lys Ile Pro Phe Lys
        210                 215                 220

Met Val Asp Val Gly Gly Gln Arg Ser Gln Arg Gln Lys Trp Phe Gln
225                 230                 235                 240

Cys Phe Asp Gly Ile Thr Ser Ile Leu Phe Met Val Ser Ser Ser Glu
                245                 250                 255

Tyr Asp Gln Val Leu Met Glu Asp Arg Arg Thr Asn Arg Leu Val Glu
            260                 265                 270

Ser Met Asn Ile Phe Glu Thr Ile Val Asn Asn Lys Leu Phe Phe Asn
        275                 280                 285

Val Ser Ile Ile Leu Phe Leu Asn Lys Met Asp Leu Leu Val Glu Lys
    290                 295                 300

Val Lys Thr Val Ser Ile Lys Lys His Phe Pro Asp Phe Arg Gly Asp
305                 310                 315                 320

Pro His Arg Leu Glu Asp Val Gln Arg Tyr Leu Val Gln Cys Phe Asp
                325                 330                 335

Arg Lys Arg Arg Asn Arg Ser Lys Pro Leu Phe His His Phe Thr Thr
            340                 345                 350

Ala Ile Asp Thr Glu Asn Val Arg Phe Val Phe His Ala Val Lys Asp
            355                 360                 365

Thr Ile Leu Gln Glu Asn Leu Lys Asp Cys Gly Leu Phe
    370                 375                 380
```